US011858972B2

(12) United States Patent
Abad Méndez et al.

(10) Patent No.: US 11,858,972 B2
(45) Date of Patent: Jan. 2, 2024

(54) MICROPEPTIDES AND USES THEREOF

(71) Applicant: FUNDACIÓ PRIVADA INSTITUT D'INVESTIGACIÓ ONCOLÒGICA DE VALL HEBRON, Barcelona (ES)

(72) Inventors: Maria Abad Méndez, Barcelona (ES); Olga Boix Sánchez, Barcelona (ES); Emanuela Greco, Barcelona (ES); Iñaki Merino Valverde, Barcelona (ES)

(73) Assignee: Fundació Privada Institut d'Investigació Oncològica de Vall Hebron, Barcelona (ES)

( * ) Notice: Subject to any disclaimer, the term of this patent is extended or adjusted under 35 U.S.C. 154(b) by 233 days.

(21) Appl. No.: 16/980,178

(22) PCT Filed: Mar. 15, 2019

(86) PCT No.: PCT/EP2019/056531
§ 371 (c)(1),
(2) Date: Sep. 11, 2020

(87) PCT Pub. No.: WO2019/175376
PCT Pub. Date: Sep. 19, 2019

(65) Prior Publication Data
US 2021/0017242 A1 Jan. 21, 2021

(30) Foreign Application Priority Data
Mar. 15, 2018 (EP) .................................... 18382173

(51) Int. Cl.
*C07K 14/47* (2006.01)
*C12N 15/63* (2006.01)

(52) U.S. Cl.
CPC ............... *C07K 14/47* (2013.01); *C12N 15/63* (2013.01)

(58) Field of Classification Search
None
See application file for complete search history.

(56) References Cited

U.S. PATENT DOCUMENTS

| 4,945,050 A | 7/1990 | Sanford et al. |
| 5,036,006 A | 7/1991 | Sanford et al. |
| 5,100,792 A | 3/1992 | Sanford et al. |
| 5,262,165 A | 11/1993 | Govil et al. |
| 5,459,127 A | 10/1995 | Felgner et al. |
| 5,580,859 A | 12/1996 | Felgner et al. |
| 5,589,466 A | 12/1996 | Felgner et al. |
| 5,846,947 A | 12/1998 | Behr et al. |
| 5,856,435 A | 1/1999 | Bazile et al. |
| 5,945,400 A | 8/1999 | Scherman et al. |
| 5,948,433 A | 9/1999 | Burton et al. |
| 6,010,715 A | 1/2000 | Wick et al. |
| 6,071,531 A | 6/2000 | Jona et al. |
| 6,107,286 A | 8/2000 | Byk et al. |
| 2015/0121569 A1 | 4/2015 | Combier et al. |

FOREIGN PATENT DOCUMENTS

| WO | 95018863 A1 | 7/1995 |
| WO | 9521931 A1 | 8/1995 |
| WO | 96017823 A1 | 6/1996 |
| WO | 96025508 A1 | 8/1996 |
| WO | 2010041237 A2 | 4/2010 |
| WO | 2015063431 A1 | 5/2015 |

OTHER PUBLICATIONS

PDF of UniProt A0A1B0GVN0 citation. Downloaded Jun. 2, 2022. (Year: 2022).*
Setrerrahmane et al., "Cancer-related micropeptides encoded by ncRNAs: Promising drug targets and prognostic biomarkers", Cancer Letters 547 (pp. 1-12 )215723 (Year: 2022).*
Wang et al., "ncRNA-Endoded Peptides or Proteins and Cancer", Molecular Therapy vol. 27, No. 10, pp. 1718-1725 (Year: 2019).*
International Search Report & Written Opinion for PCT/EP2019/056531, dated Jun. 18, 2019.
Douglas M. Anderson et al., A Micropeptide Encoded by a Putative Long Noncoding RNA Regulates Muscle Performance, CELL, Jan. 29, 2015, pp. 595-606, vol. 160, No. 4.
Adam M. Schmitt et al., "Long Noncoding RNAs in Cancer Pathways", Cancer Cell, Apr. 11, 2016, pp. 452-463, vol. 29, No. 4.
Markus Kretz et al., "Control of somatic tissue differentiation by the long non-coding RNA TINCR", Nature, Jan. 1, 2013, pp. 231-235, vol. 493, No. 7431.
Zhi-Jun Zhu et al, "TINCR facilitates non-small cell lung cancer progression through BRAF-activated MAPK pathway", Biochemical and Biophysical Research Communications, Mar. 1, 2018, pp. 971-977, vol. 497, No. 4.
Feng Tian et al, "TINCR expression is associated with unfavorable prognosis in patients with hepatocellular carcinoma", Bioscience Reports, May 25, 2017, vol. 37, No. 4.
T-P Xu et al, "SPI-induced upregulation of the long noncoding RNA TINCR regulates cell proliferation and apoptosis by affecting KLF2 mRNA stability in gastric cancer", Oncogene, Mar. 2, 2015, pp. 5648-5661, vol. 34, No. 45.
Database UniProt [Online], Feb. 28, 2018 (Feb. 28, 2018), "TINCR ubiquitin domain-containing", XP002784458, Database accession No. A0A1B0GVN0.
Database UniProt [Online], Nov. 22, 2017 (Nov. 22, 2017), "Small integral membrane protein 10-like protein 2A", XP002784459, Database accession No. P0DMW4.
Jie Guo et al: "Long Noncoding RNA LINC0086 Functions as a Tumor Suppressor in Nasopharyngeal Carcinoma by Targeting miR-214", Oncology Research, Aug. 7, 2017, pp. 1189-1197, vol. 25, No. 7.

(Continued)

*Primary Examiner* — Anand U Desai
(74) *Attorney, Agent, or Firm* — Piloff Passino & Cosenza LLP; Sean A. Passino; Rachel K. Piloff

(57) ABSTRACT

The present invention relates to new peptidic compounds, more specifically to micropeptides derived from lncRNAs implicated in cancer and cellular plasticity. It also relates to the use of the said micropeptides in the treatment of proliferative diseases, more specifically in the treatment of cancer.

7 Claims, 30 Drawing Sheets

Specification includes a Sequence Listing.

(56) References Cited

OTHER PUBLICATIONS

Yang Guo et al: "Long non-coding RNA ZEB2-AS1 promotes proliferation and inhibits apoptosis in human lung cancer cells", Oncology Letters, Feb. 1, 2018, pp. 5,220-5,226, vol. 15.
Jonathan B. Ball et al., "Conformational Constraints: Nonpeptide β-Turn Mimics," Journal of Molecular Recognition, Apr. 1990, pp. 55-64, vol. 3, No. 2.
Barry A. Morgan et al., "Approaches to the Discovery of Non-Peptide Ligands for Peptide Receptors and Peptidases," Annual Reports in Medicinal Chemistry, Jan. 1989, pp. 243-252, vol. 24.
Roger M. Freidinger, "Non-peptide ligands for peptide receptors," TiPS, Jul. 1989, pp. 270-274, vol. 10.
Amos B. Smith, III et al., "Pyrrolinone-Based HIV Protease Inhibitors. Design, Synthesis, and Antiviral Activity: Evidence for Improved Transport," Journal of the American Chemical Society, Nov. 1995, pp. 11, 113- 11, 123, vol. 117, No. 45.
Amos B. Smith, III et al., "De Novo Design, Synthesis, and X-ray Crystal Structures of Pyrrolinone-Based beta-Strand Peptidomimetics," Journal of the American Chemical Society, May 1994, pp. 9,947-9,962, vol. 116, No. 22.
Ralph Hirschmann et al., "De Novo Design and Synthesis of Somatostatin Non-Peptide Peptidomimetics Utilizing beta-D-Glucose as a Novel Scaffolding," Journal of the American Chemical Society, Jan. 1993, pp. 12,550-12,568, vol. 115, No. 26.
Guy L. James et al., "Benzodiazepine Peptidomimetics: Potent Inhibitors of Ras Farnesylation in Animal Cells," Science, Jun. 25, 1993, pp. 1,937-1,942, vol. 260.
Samuel Karlin et al., "Methods for assessing the statistical significance of molecular sequence features by using general scoring schemes," Proc. Natl. Acad. Sci. USA, Mar. 1990, pp. 2,264-2,268, vol. 87.
Samuel Karlin et al., "Applications and statistics for multiple high-scoring segments in molecular sequences," Proc. Natl. Acad. Sci. USA, Jun. 1993, pp. 5,873-5,877, vol. 90.
Stephen F. Altschul et al., "Gapped BLAST and PSI-BLAST: a new generation of protein database search programs," Nucleic Acids Research, Jul. 1997, pp. 3,389-3,402, vol. 25, No. 1.
Stephen F. Altschul et al., "Local Alignment Statistics," Methods in Enzymology, Jan. 1996, vol. 266.
Saul B. Needleman et al., "A General Method Applicable to the Search for Similarities in the Amino Acid Sequence of Two Proteins," J. Mol. Biol., Jan. 1970, pp. 443-453, vol. 48.
James M. Wilson et al., "Hepatocyte-directed Gene Transfer in Vivo Leads to Transient Improvement of Hypercholesterolemia in Low Density Lipoprotein Receptor-deficient Rabbits," The Journal of Biological Chemistry, Jan. 15, 1992, pp. 963-967, vol. 267, No. 2.
George Y. Wu et al., "Receptor-mediated Gene Delivery and Expression in Vivo," The Journal of Biological Chemistry, Oct. 15, 1988, pp. 14,621-14,624, vol. 263, No. 29.
R. Sanders Williams et al., "Introduction of foreign genes into tissues of living mice by DNA-coated microprojectiles," Proc. Nati. Acad. Sci. USA, Apr. 1991, pp. 2,726-2,730, vol. 88.
P.L. Felgner et al., "Cationic liposome-mediated transfection," Nature, Jan. 26, 1989, pp. 387-388, vol. 337.
Dan Michalovitz et al., "p53 Mutations: Gains or Losses?," Journal of Cellular Biochemistry, Jan. 1991, pp. 22-29, vol. 45.
Bert Vogelstein et al., "p53 Function and Dysfunction," Cell, Aug. 21, 1992, pp. 523-526, vol. 70.
Lawrence A. Donehower et al., "The tumor suppressor p53," Biochimica et Biophysica Acta, Aug. 1993, pp. 181-205, vol. 1,155.
Arnold J. Levine, "p53, the Cellular Gatekeeper for Growth and Division," Cell, Feb. 7, 1997, pp. 323-331, vol. 88.
Christophe Beroud et al., "p53 gene mutation: software and database," Nucleic Acids Research, Jan. 1998, pp. 200-204, vol. 26, No. 1.
P. Hainaut et al., "IARC Database of p53 gene mutations in human tumors and cell lines: updated compilation, revised formats and new visualisation tools," Nucleic Acids Research, Jan. 1998, pp. 205-213, vol. 26, No. 1.
Neal F. Cariello et al., "Databases and software for the analysis of mutations in the human p53 gene, human hprt gene and both the lacI and lacZ gene in transgenic rodents," Nucleic Acids Research, Jan. 1998, pp. 198-199, vol. 26, No. 1.
Thomas A Wynn et al., "Mechanisms of fibrosis: therapeutic translation for fibrotic disease," Nature Medicine, Jul. 2012, pp. 1,028-1,040, vol. 18.
Yuejuan Li et al., "Severe lung fibrosis requires an invasive fibroblast phenotype regulated by hyaluronan and CD44," The Journal of Experimental Medicine, Jul. 2011, pp. 1,459-1,471, vol. 208, No. 7.
Li-Wang Yang et al., "CD44 deficiency in mice protects the heart against angiotensin II-induced cardiac fibrosis," Shock, Mar. 2019, DOI : 10.1097/SHK.0000000000001132.
Mark Hochstrasser, "Origin and Function of Ubiquitin-like Protein Conjugation," Nature, Mar. 26, 2009, 458(7237): 422.
Rosa F. Hwang et al., "Cancer-Associated Stromal Fibroblasts Promote Pancreatic Tumor Progression," Cancer Research, Feb. 1, 2008, pp. 918-926, vol. 68, No. 3.

\* cited by examiner

A

```
Homo_sapiens          (SEQ ID NO: 2)  MVRRKSMKPRSVGEKKVEAKKQLPEQTVQRPQECREAGPLFLQSRRETNDPETRATYLCGEG
Pongo_abelii          (SEQ ID NO: 12) MVRRKSMKPRSVGEKKVEAKKQLPEQTVQRPQECREAGPLFLQSRRETNDPETRATYLCGEG
microcebus_           (SEQ ID NO: 13) MVRRKSMKPRSVGEKKVEAKKQLPEQTVQKPQECREAGPLFLRSRERRDPETRATYLCGEG
Propithecus_coquereli (SEQ ID NO: 14) MVRRKSMKPRSVGEKKVEAKKQLPEQTVQRPQECREAGPLFLRSRERRDPETRATYLCGEG
                                     ******************************:******:***:******************
```

B

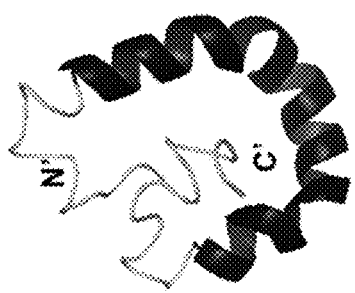

SEQ ID NO: 2

FIG. 2

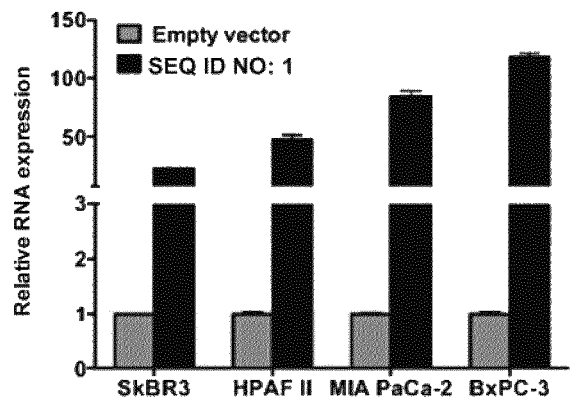
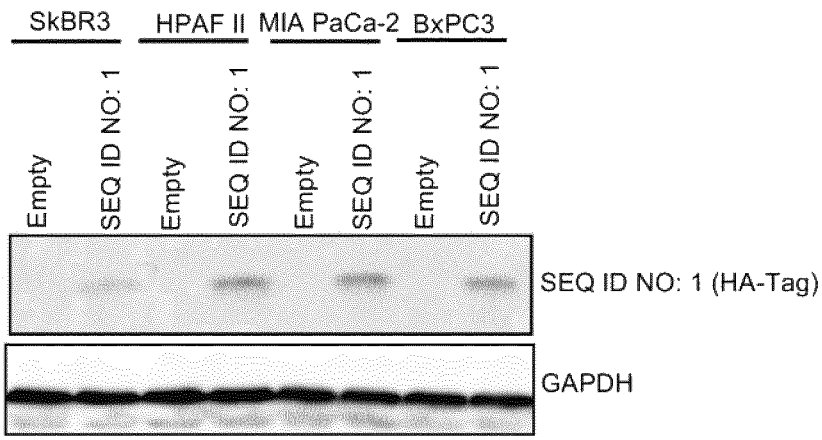
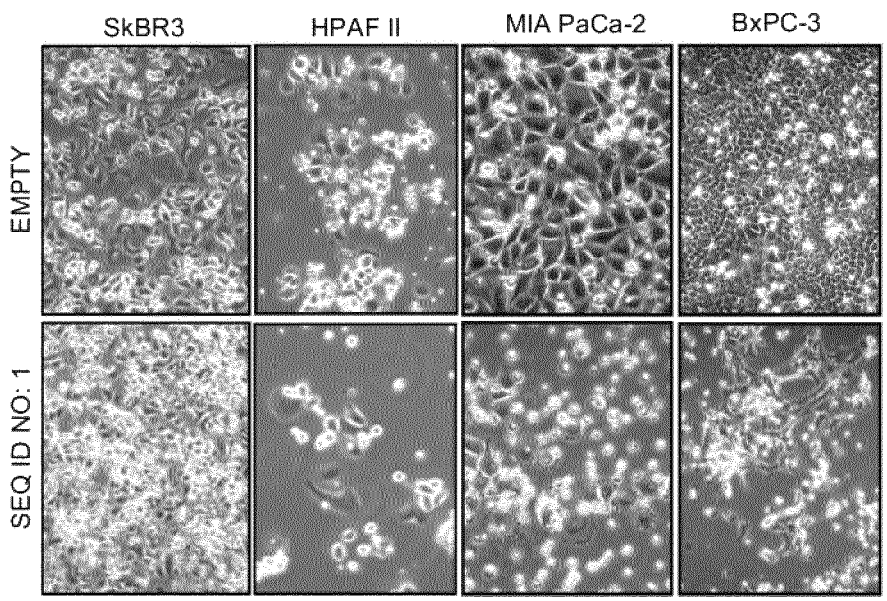
FIG. 6

D
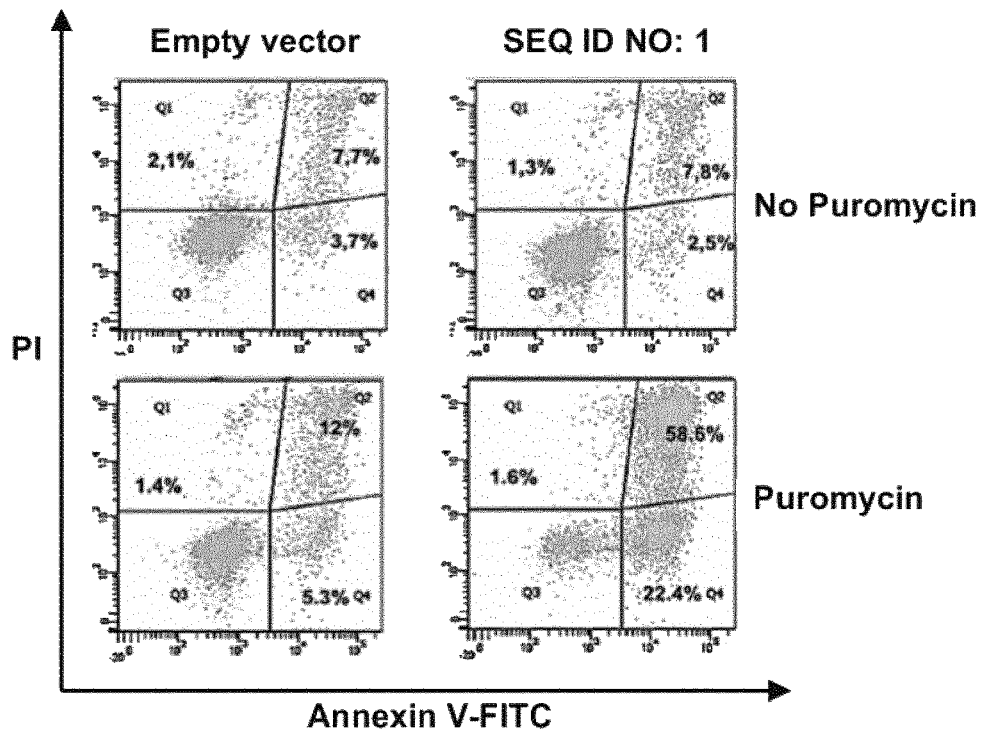
E
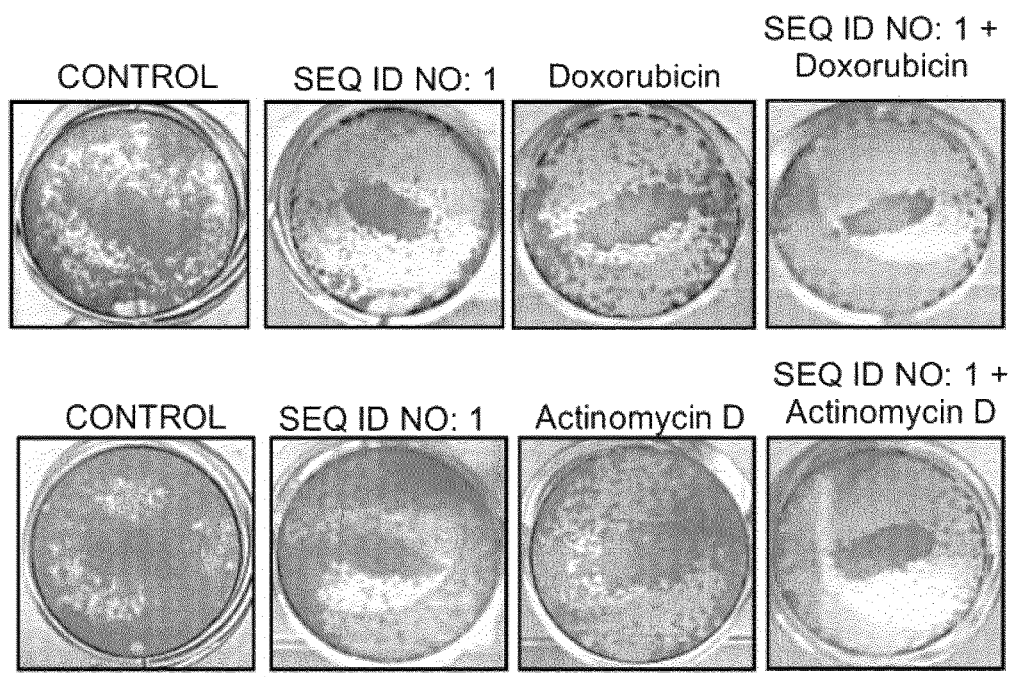
FIG. 6 (Cont.)

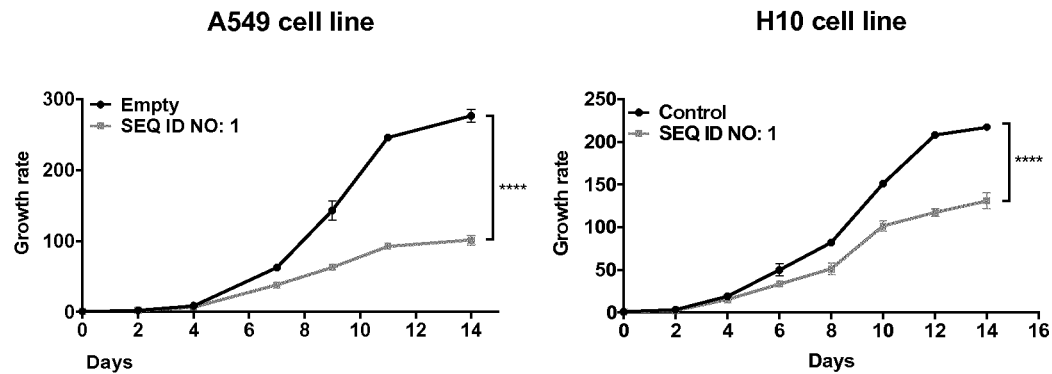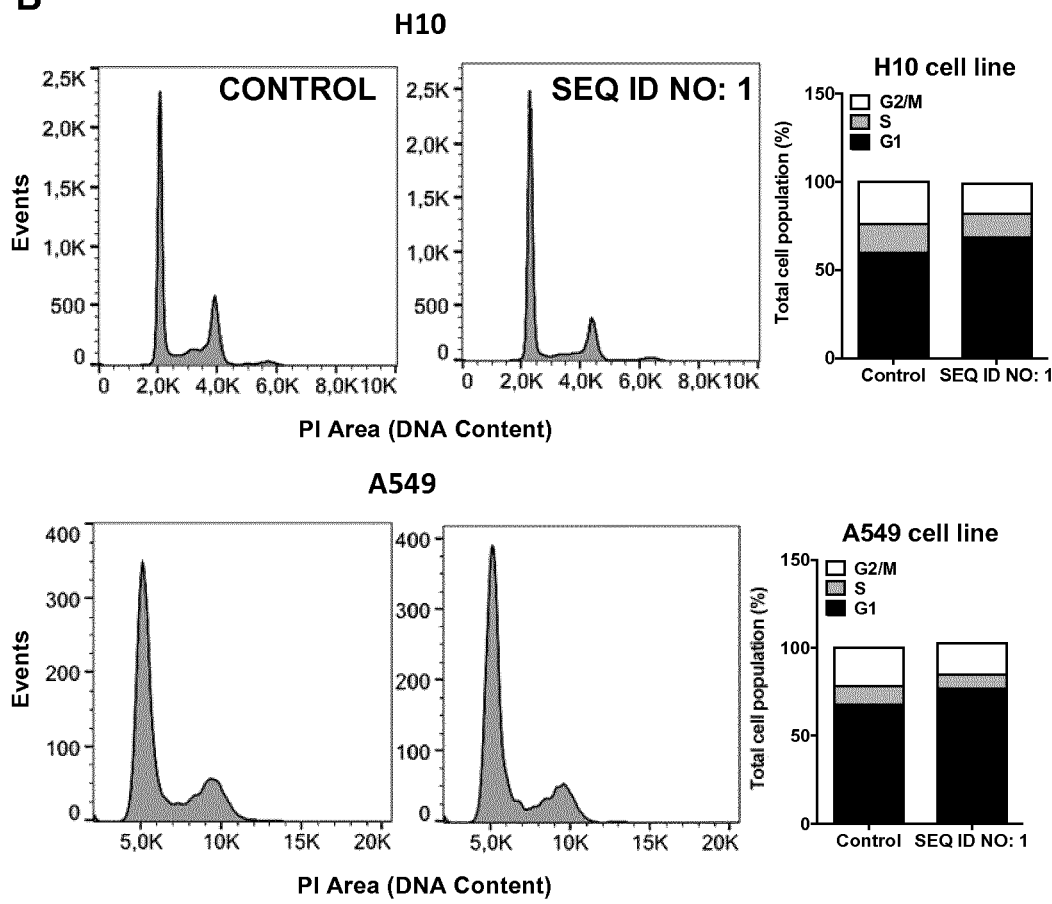
FIG. 8

A
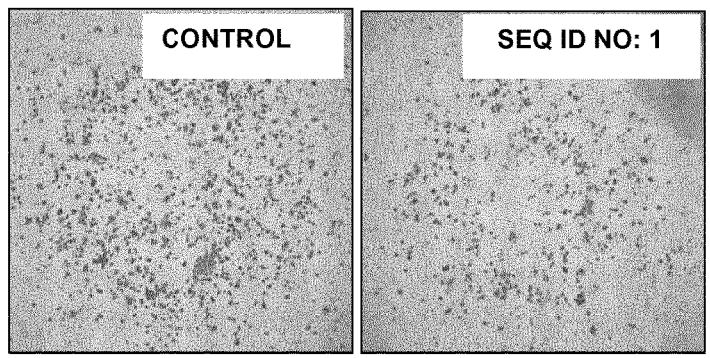
B
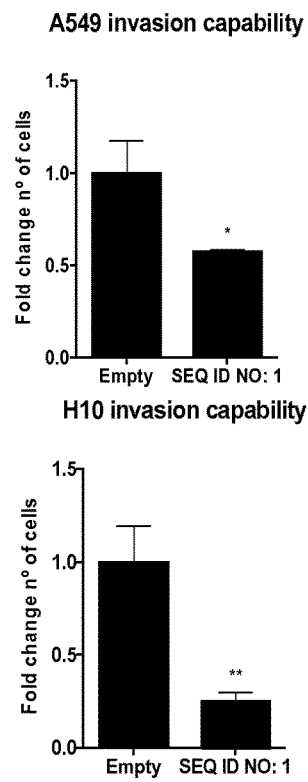
C
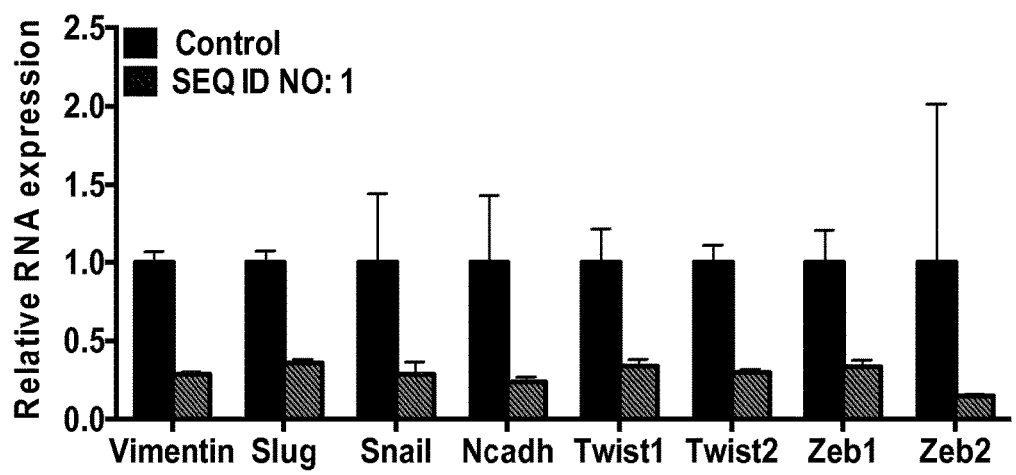
FIG. 9

A
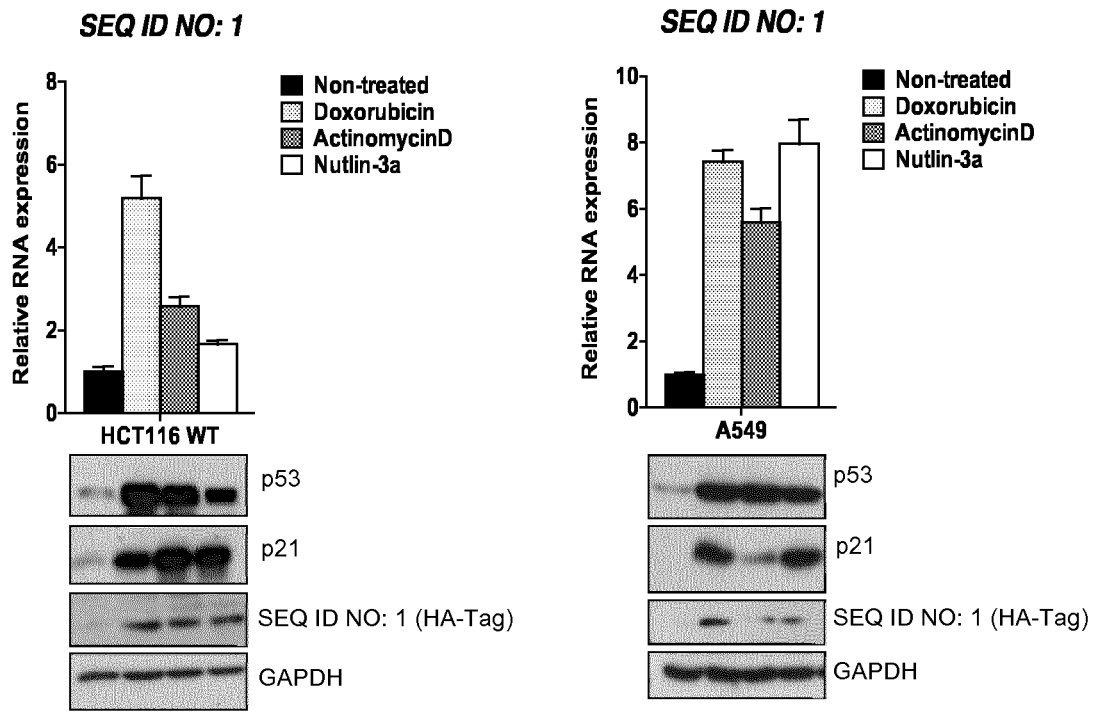
B
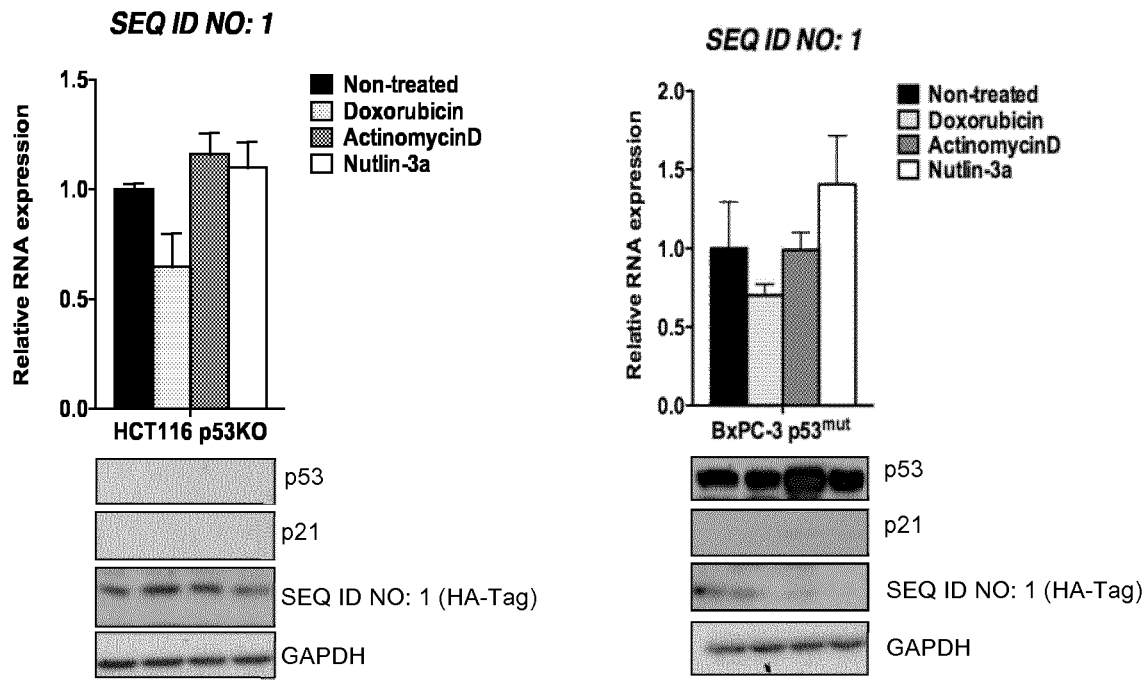
FIG. 10

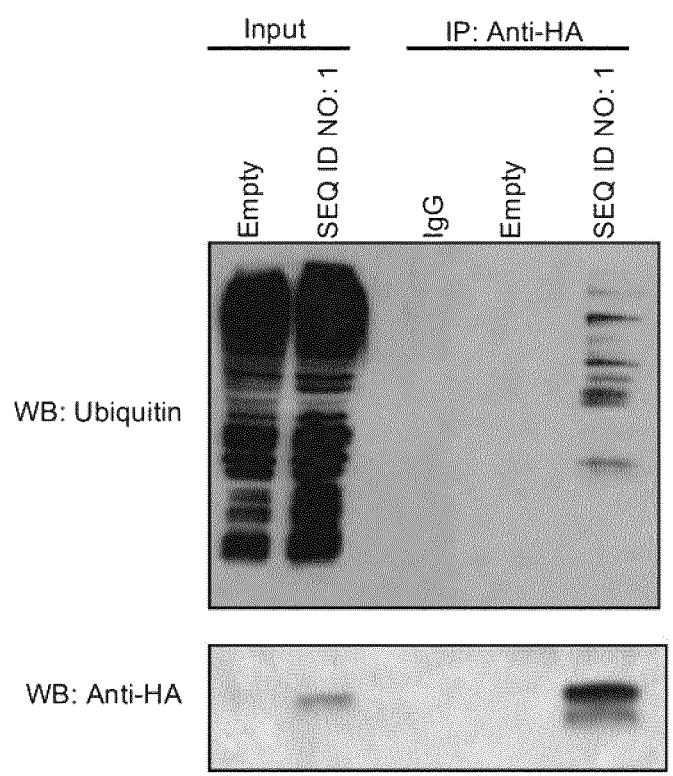
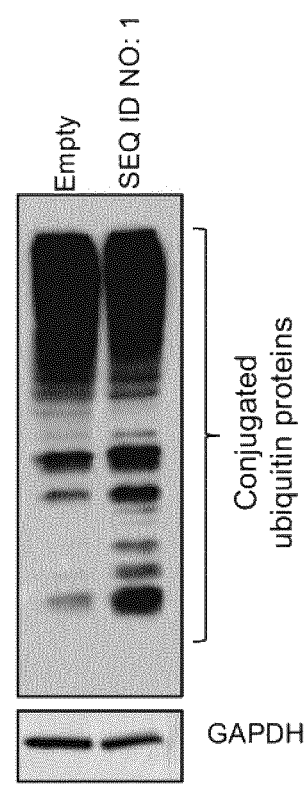
FIG. 11

A
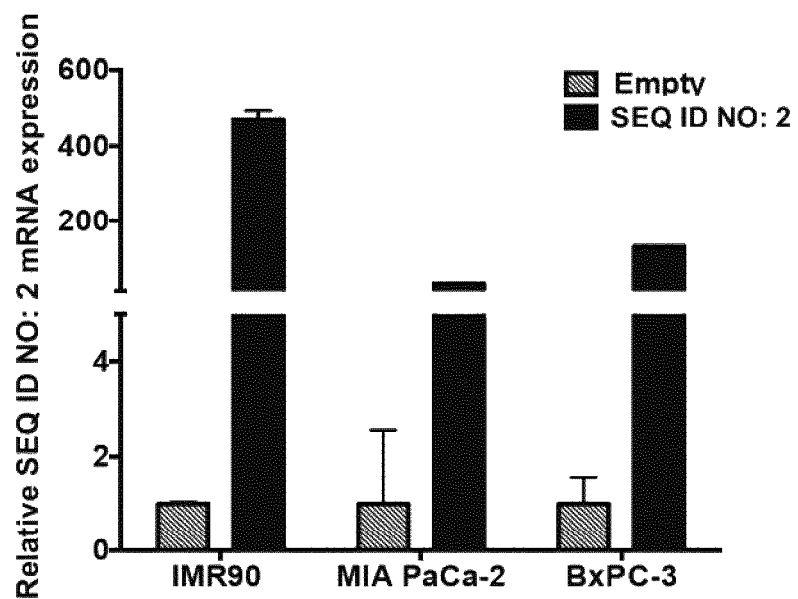
B
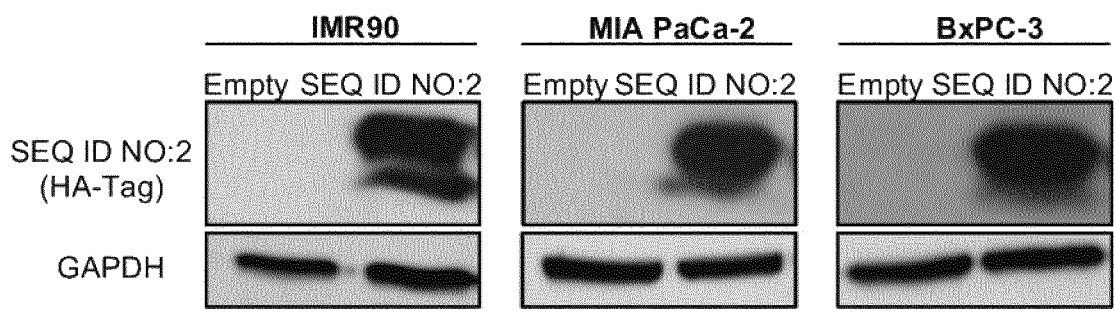
FIG. 12

Empty | SEQ ID NO: 2
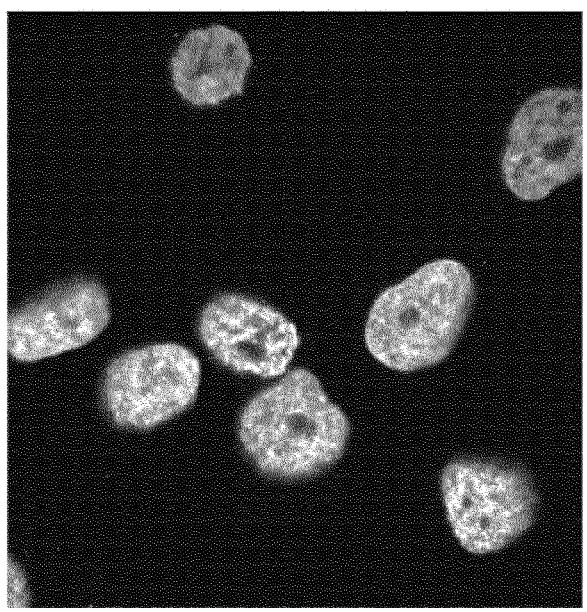 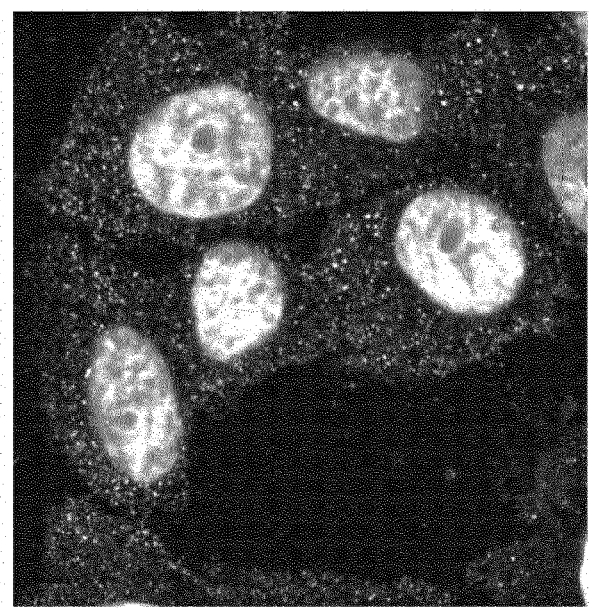
FIG. 14

A
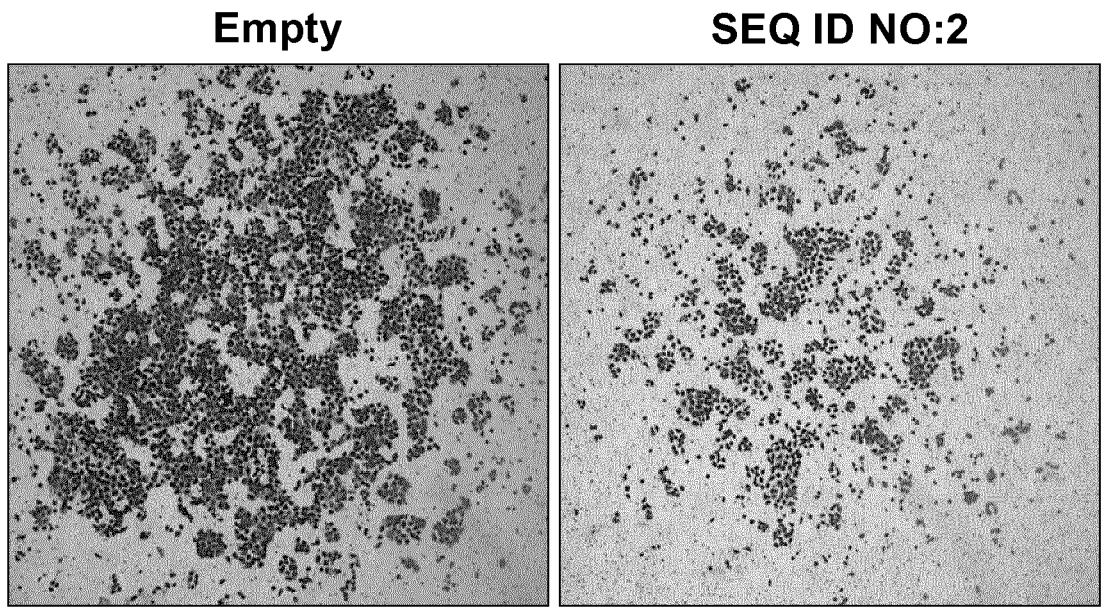
B
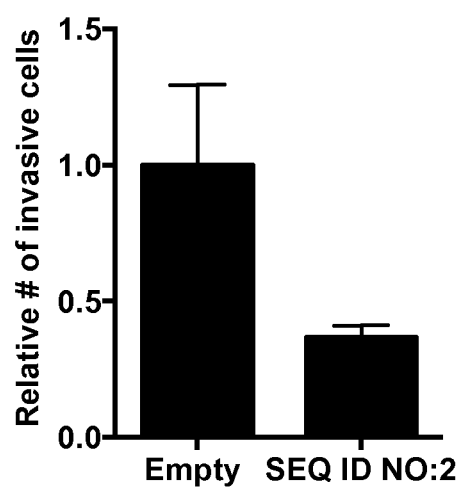
FIG. 18

A
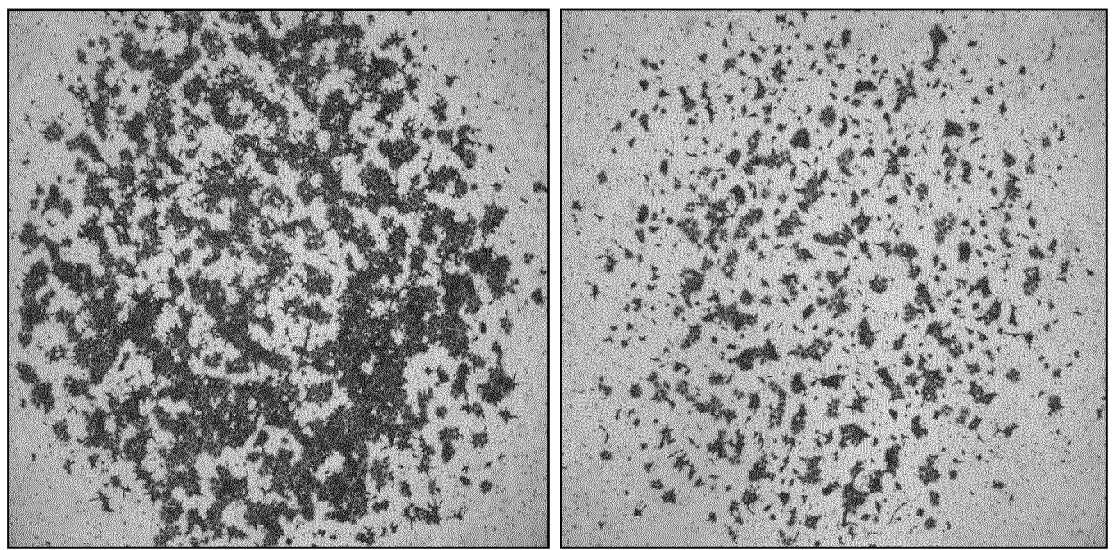
B
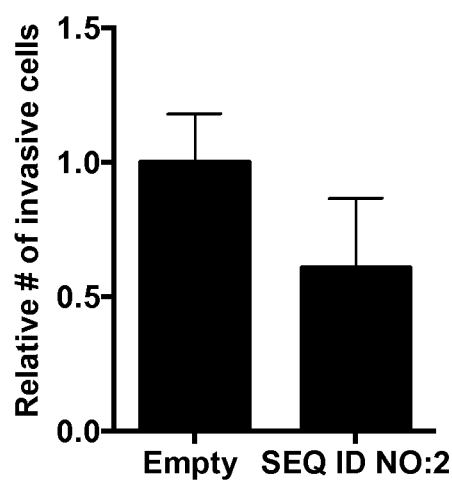
FIG. 19

A
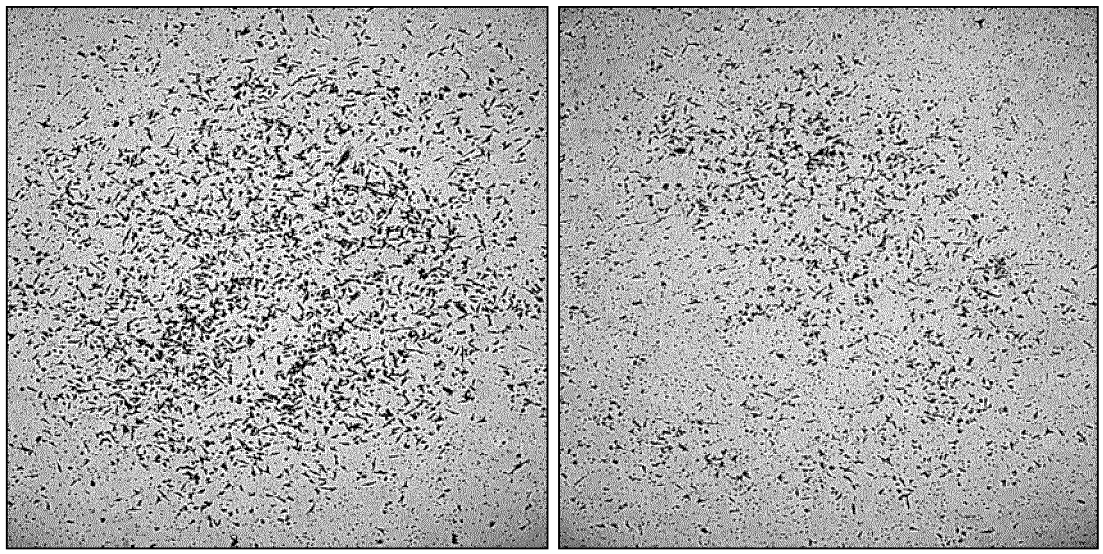
B
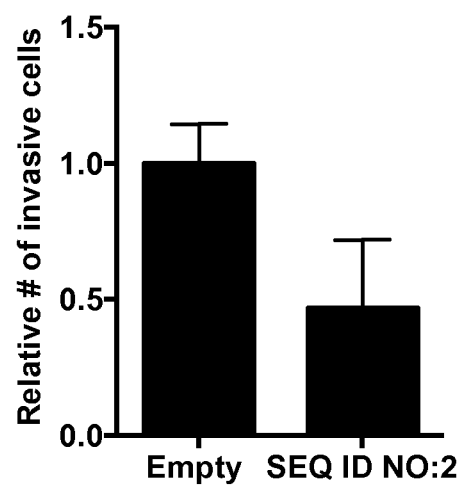
FIG. 22

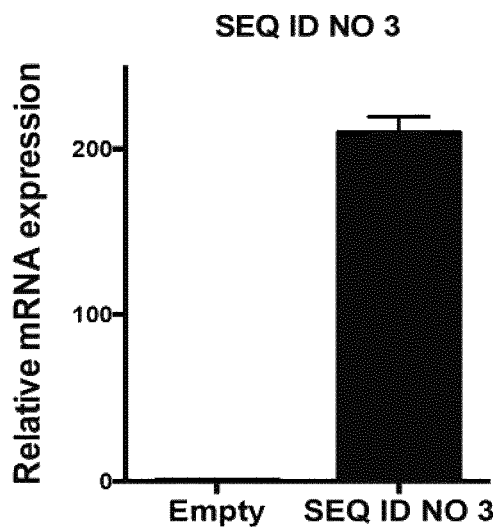
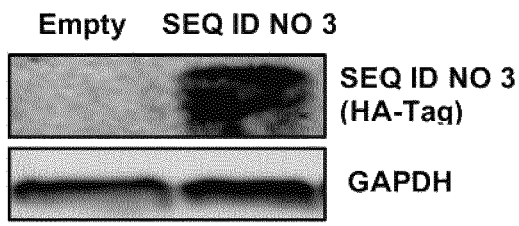
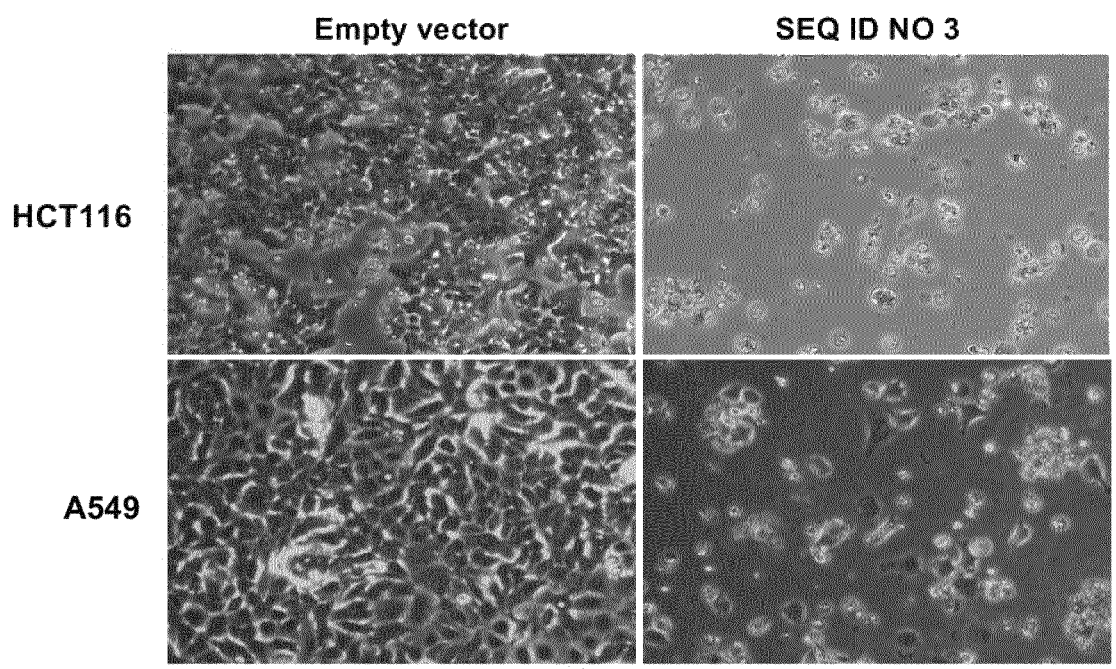
FIG. 23

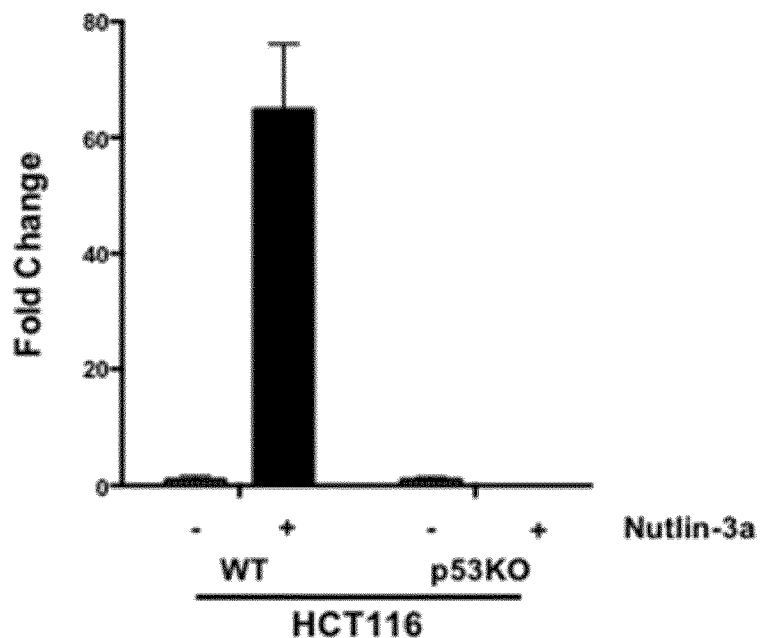
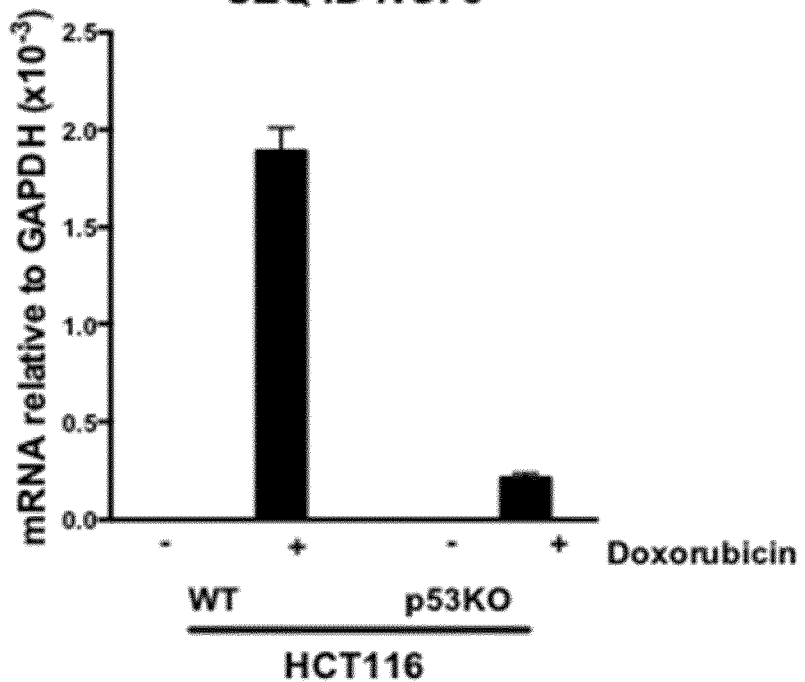
FIG. 25

SEQUENCE LISTING

<160> NUMBER OF SEQ ID NOS: 22

<210> SEQ ID NO 1
<211> LENGTH: 87
<212> TYPE: PRT
<213> ORGANISM: Homo sapiens

<400> SEQUENCE: 1

```
Met Glu Gly Leu Arg Arg Gly Leu Ser Arg Trp Lys Arg Tyr His Ile
1               5                   10                  15

Lys Val His Leu Ala Asp Glu Ala Leu Leu Leu Pro Leu Thr Val Arg
                20                  25                  30

Pro Arg Asp Thr Leu Ser Asp Leu Arg Ala Gln Leu Val Gly Gln Gly
            35                  40                  45

Val Ser Ser Trp Lys Arg Ala Phe Tyr Tyr Asn Ala Arg Arg Leu Asp
        50                  55                  60

Asp His Gln Thr Val Arg Asp Ala Arg Leu Gln Asp Gly Ser Val Leu
65                  70                  75                  80

Leu Leu Val Ser Asp Pro Arg
                85
```

<210> SEQ ID NO 2
<211> LENGTH: 64
<212> TYPE: PRT
<213> ORGANISM: Homo sapiens

<400> SEQUENCE: 2

```
Met Val Arg Arg Lys Ser Met Lys Lys Pro Arg Ser Val Gly Glu Lys
1               5                   10                  15

Lys Val Glu Ala Lys Lys Gln Leu Pro Glu Gln Thr Val Gln Lys Pro
                20                  25                  30

Arg Gln Glu Cys Arg Glu Ala Gly Pro Leu Phe Leu Gln Ser Arg Arg
            35                  40                  45

Glu Thr Arg Asp Pro Glu Thr Arg Ala Thr Tyr Leu Cys Gly Glu Gly
        50                  55                  60
```

<210> SEQ ID NO 3
<211> LENGTH: 78
<212> TYPE: PRT
<213> ORGANISM: Homo sapiens

<400> SEQUENCE: 3

Met Ala Ser Ala Ala Leu Ser Ala Ala Ala Ala Ala Ala Ala Ala Leu
1               5                   10                  15

Ser Gly Leu Ala Val Arg Leu Ser Arg Ser Ala Ala Ala Arg Gly Ser
                20                  25                  30

Tyr Gly Ala Phe Cys Lys Gly Leu Thr Arg Thr Leu Leu Thr Phe Phe
            35                  40                  45

Asp Leu Ala Trp Arg Leu Arg Met Asn Phe Pro Tyr Phe Tyr Ile Val
        50                  55                  60

Ala Ser Val Met Leu Asn Val Arg Leu Gln Val Arg Ile Glu
65                  70                  75

<210> SEQ ID NO 4
<211> LENGTH: 87
<212> TYPE: PRT
<213> ORGANISM: Heterocephalus glaber

<400> SEQUENCE: 4

Met Glu Gly Leu Arg Arg Gly Leu Arg Arg Trp Lys Arg Phe His Ile
1               5                   10                  15

Lys Val His Leu Ala Asp Glu Ala Leu Leu Pro Leu Thr Val Arg
                20                  25                  30

Pro Gly Asp Thr Leu Ser Asp Val Arg Ala Gln Leu Val Gly Arg Gly
            35                  40                  45

Val Gly Ser Trp Arg Arg Thr Phe Tyr Tyr Asn Ala Arg Ala Leu Arg
        50                  55                  60

Asp Ser Gln Thr Val Arg Glu Ala Arg Leu Gln Asp Gly Ala Val Leu
65                  70                  75                  80

Leu Leu Leu His Asp Pro Arg
                85

<210> SEQ ID NO 5
<211> LENGTH: 87
<212> TYPE: PRT
<213> ORGANISM: Gorilla gorilla gorilla

<400> SEQUENCE: 5

Met Glu Gly Leu Arg Arg Gly Leu Ser Arg Trp Lys Arg Tyr His Ile
1               5                   10                  15

Lys Val His Leu Ala Asp Glu Ala Leu Leu Pro Leu Thr Val Arg
                20                  25                  30

Pro Arg Asp Thr Leu Ser Asp Leu Arg Val Gln Leu Val Gly Gln Gly
            35                  40                  45

Val Ser Ser Trp Lys Arg Ala Phe Tyr Tyr Asn Ala Arg Arg Leu Asp
        50                  55                  60

Asp His Gln Thr Val Arg Asp Ala Arg Leu Gln Asp Gly Ser Val Leu
65                  70                  75                  80

Leu Leu Val Ser Asp Pro Arg
                85

<210> SEQ ID NO 6
<211> LENGTH: 87
<212> TYPE: PRT
<213> ORGANISM: Cebus capucinus imitator

<400> SEQUENCE: 6

Met Glu Gly Leu Arg Arg Gly Leu Ser Arg Trp Lys Arg Tyr His Ile
1               5                   10                  15

```
Lys Val His Leu Ala Asp Glu Ala Leu Leu Pro Leu Thr Val Arg
            20                  25                  30

Pro Arg Asp Thr Leu Ser Asp Leu Arg Ala Gln Leu Val Gly Gln Gly
        35                  40                  45

Val Ser Ser Trp Lys Arg Ala Phe Tyr Tyr Asn Ala Arg Arg Leu Asp
 50                  55                  60

Asp His Gln Thr Val Arg Asp Ala Arg Leu Gln Asp Gly Ser Val Leu
 65                  70                  75                  80

Leu Leu Val Ser Asp Pro Arg
                85

<210> SEQ ID NO 7
<211> LENGTH: 86
<212> TYPE: PRT
<213> ORGANISM: Pan troglodytes

<400> SEQUENCE: 7

Met Glu Gly Leu Arg Arg Gly Leu Ser Arg Trp Lys Arg Tyr His Ile
 1               5                  10                  15

Lys Val His Leu Ala Asp Glu Ala Leu Leu Pro Leu Thr Val Arg
            20                  25                  30

Pro Arg Asp Thr Leu Ser Asp Leu Arg Ala Gln Leu Val Gly Gln Gly
        35                  40                  45

Val Ser Ser Trp Lys Arg Ala Phe Tyr Tyr Asn Ala Arg Arg Leu Asp
 50                  55                  60

Asp His Gln Thr Val Arg Asp Ala Arg Leu Gln Asp Gly Ser Val Leu
 65                  70                  75                  80

Leu Leu Val Ser Asp Pro
                85

<210> SEQ ID NO 8
<211> LENGTH: 86
<212> TYPE: PRT
<213> ORGANISM: Macaca nemestrina

<400> SEQUENCE: 8

Met Glu Gly Leu Arg Arg Gly Leu Ser Arg Trp Lys Arg Tyr His Ile
 1               5                  10                  15

Lys Val His Leu Ala Asp Glu Ala Leu Leu Pro Leu Thr Val Arg
            20                  25                  30

Pro Arg Asp Thr Leu Ser Asp Leu Arg Ala Gln Leu Val Gly Gln Gly
        35                  40                  45

Val Ser Ser Trp Lys Arg Ala Phe Tyr Tyr Asn Ala Arg Arg Leu Asp
 50                  55                  60

Asp His Gln Thr Val Arg Asp Ala Arg Leu Gln Asp Gly Ser Val Leu
 65                  70                  75                  80

Leu Leu Val Ser Asp Pro
                85

<210> SEQ ID NO 9
<211> LENGTH: 87
<212> TYPE: PRT
<213> ORGANISM: Ictidomys tridecemlineatus

<400> SEQUENCE: 9

Met Glu Gly Leu Arg Arg Gly Leu Trp Arg Trp Lys Arg Tyr His Ile
 1               5                  10                  15
```

```
Lys Val His Leu Ala Asp Glu Ala Leu Leu Pro Leu Thr Val Arg
            20                  25                  30

Pro Arg Asp Thr Leu Ser Asp Leu Arg Ala Gln Leu Val Gly Gln Gly
        35                  40                  45

Val Ser Ser Trp Lys Arg Thr Phe Tyr Tyr Asn Ala Arg Pro Leu Arg
    50                  55                  60

Asp His Gln Thr Val Arg Glu Ala Arg Leu Gln Asp Gly Ala Val Leu
65                  70                  75                  80

Leu Leu Val Ser Asp Pro Arg
                85
```

<210> SEQ ID NO 10
<211> LENGTH: 87
<212> TYPE: PRT
<213> ORGANISM: Mus musculus

<400> SEQUENCE: 10

```
Met Glu Glu Leu Arg Arg Gly Leu Ser Arg Trp Lys Arg Tyr His Ile
1               5                   10                  15

Lys Val His Leu Ala Asp Glu Ala Leu Leu Leu Pro Leu Thr Val Arg
            20                  25                  30

Pro Arg Asp Thr Leu Ser Asp Leu Arg Ala Gln Leu Val Gly Gln Gly
        35                  40                  45

Val Ser Ser Trp Arg Arg Thr Phe Tyr Tyr Asn Ser Arg Pro Leu Pro
    50                  55                  60

Asp His Gln Thr Val Arg Glu Ala Arg Leu Gln Asp Gly Ser Val Leu
65                  70                  75                  80

Leu Leu Leu Ser Asp Thr Arg
                85
```

<210> SEQ ID NO 11
<211> LENGTH: 87
<212> TYPE: PRT
<213> ORGANISM: Cricetulus griseus

<400> SEQUENCE: 11

```
Met Glu Gly Leu Arg Arg Gly Leu Ser Arg Trp Lys Arg Tyr His Ile
1               5                   10                  15

Lys Val His Leu Ala Asp Glu Ala Leu Leu Leu Pro Leu Thr Val Arg
            20                  25                  30

Pro Arg Asp Thr Leu Ser Asp Leu Arg Ala Gln Leu Val Gly Gln Gly
        35                  40                  45

Val Ser Ser Trp Arg Arg Thr Phe Tyr Tyr Asn Ala Arg Pro Leu Pro
    50                  55                  60

Asp His Gln Thr Val Arg Glu Ala Arg Leu Gln Asp Gly Ser Val Leu
65                  70                  75                  80

Leu Leu Leu Ser Asp Pro Arg
                85
```

<210> SEQ ID NO 12
<211> LENGTH: 64
<212> TYPE: PRT
<213> ORGANISM: Pongo abelii

<400> SEQUENCE: 12

```
Met Val Arg Arg Lys Ser Met Lys Lys Pro Arg Ser Val Gly Glu Lys
1               5                   10                  15

Lys Val Glu Ala Lys Lys Gln Leu Pro Glu Gln Thr Val Gln Lys Pro
```

```
                20                  25                  30

Arg Gln Glu Cys Arg Glu Ala Gly Pro Leu Phe Leu Gln Ser Arg Arg
            35                  40                  45

Glu Thr Arg Asp Pro Glu Thr Arg Ala Thr Tyr Leu Cys Gly Glu Gly
        50                  55                  60

<210> SEQ ID NO 13
<211> LENGTH: 64
<212> TYPE: PRT
<213> ORGANISM: Microcebus murinus

<400> SEQUENCE: 13

Met Val Arg Arg Lys Ser Met Lys Lys Pro Arg Ser Val Gly Glu Lys
1               5                   10                  15

Lys Val Glu Ala Lys Lys Gln Leu Pro Glu Gln Thr Val Gln Lys Pro
            20                  25                  30

Arg Gln Glu Cys Arg Glu Ala Gly Pro Leu Phe Leu Arg Ser Arg Arg
            35                  40                  45

Glu Arg Arg Asp Pro Glu Thr Arg Ala Thr Tyr Leu Cys Gly Glu Gly
        50                  55                  60

<210> SEQ ID NO 14
<211> LENGTH: 64
<212> TYPE: PRT
<213> ORGANISM: Propithecus coquereli

<400> SEQUENCE: 14

Met Val Arg Arg Lys Ser Met Lys Lys Pro Arg Ser Val Gly Glu Lys
1               5                   10                  15

Lys Val Glu Ala Lys Lys Gln Leu Pro Glu Gln Thr Val Gln Lys Pro
            20                  25                  30

Arg Gln Glu Cys Arg Glu Ala Gly Pro Leu Phe Leu Gln Ser Arg Arg
            35                  40                  45

Glu Thr Arg Asp Pro Glu Thr Arg Ala Thr Tyr Leu Cys Gly Glu Gly
        50                  55                  60

<210> SEQ ID NO 15
<211> LENGTH: 77
<212> TYPE: PRT
<213> ORGANISM: Dasypus novemcinctus

<400> SEQUENCE: 15

Met Ala Ala Ser Ala Ala Leu Ser Ala Ala Ala Ala Ala Ala Leu Ser
1               5                   10                  15

Gly Leu Val Val Arg Leu Ser Arg Ser Ala Ala Val Arg Gly Ser Tyr
            20                  25                  30

Gly Ala Phe Cys Lys Gly Leu Thr Arg Thr Leu Leu Thr Phe Phe Asp
            35                  40                  45

Leu Ala Trp Arg Leu Arg Met Asn Phe Pro Tyr Phe Tyr Val Val Ala
        50                  55                  60

Ser Val Met Leu Asn Val Arg Leu Gln Val Arg Ile Glu
65                  70                  75

<210> SEQ ID NO 16
<211> LENGTH: 78
<212> TYPE: PRT
<213> ORGANISM: Mus musculus

<400> SEQUENCE: 16
```

Met Ala Val Thr Ala Ala Leu Ser Ala Ala Ala Ala Ala Ala Ala Leu
1               5                   10                  15

Ser Gly Leu Ala Val Arg Leu Ser Arg Trp Ala Ala Thr Arg Ser Ser
            20                  25                  30

Tyr Gly Ala Phe Cys Lys Gly Leu Thr Arg Thr Leu Leu Thr Phe Phe
            35                  40                  45

Asp Leu Ala Trp Arg Leu Arg Val Asn Phe Pro Tyr Phe Tyr Met Val
            50                  55                  60

Ala Ser Val Met Leu Asn Val Arg Leu Gln Val Arg Ile Glu
65                  70                  75

<210> SEQ ID NO 17
<211> LENGTH: 78
<212> TYPE: PRT
<213> ORGANISM: Sus scrofa

<400> SEQUENCE: 17

Met Ala Ala Ser Ser Ala Leu Ser Ala Ala Ala Ala Ala Ala Ala Leu
1               5                   10                  15

Ser Gly Leu Ala Val Arg Leu Ser Arg Ser Ala Ala Ala Arg Gly Ser
            20                  25                  30

Tyr Ser Ala Phe Cys Lys Gly Leu Thr Arg Thr Leu Leu Thr Phe Phe
            35                  40                  45

Asp Leu Ala Trp Arg Leu Arg Met Asn Phe Pro Tyr Val Tyr Val Leu
            50                  55                  60

Ala Ser Val Met Leu Asn Val Arg Leu Gln Val Arg Ile Glu
65                  70                  75

<210> SEQ ID NO 18
<211> LENGTH: 78
<212> TYPE: PRT
<213> ORGANISM: Oryctolagus cuniculus

<400> SEQUENCE: 18

Met Ala Ala Ser Ala Ala Leu Ser Ala Ala Ala Ala Ala Ala Ala Leu
1               5                   10                  15

Ser Gly Leu Ala Val Arg Leu Ser Arg Ser Ala Ala Ala Arg Gly Ser
            20                  25                  30

Tyr Ser Ala Phe Cys Lys Gly Leu Thr Arg Thr Leu Leu Thr Phe Phe
            35                  40                  45

Asp Leu Ala Trp Arg Leu Arg Met Asn Phe Pro Tyr Phe Tyr Ile Val
            50                  55                  60

Ala Ser Val Met Leu Asn Val Arg Leu Gln Val Arg Ile Glu
65                  70                  75

<210> SEQ ID NO 19
<211> LENGTH: 78
<212> TYPE: PRT
<213> ORGANISM: Pan troglodytes

<400> SEQUENCE: 19

Met Ala Ala Ser Ala Ala Leu Ser Ala Ala Ala Ala Ala Ala Ala Leu
1               5                   10                  15

Ser Gly Leu Ala Val Arg Leu Ser Arg Ser Ala Ala Ala Arg Gly Ser
            20                  25                  30

Tyr Gly Ala Phe Cys Lys Gly Leu Thr Arg Thr Leu Leu Thr Phe Phe
            35                  40                  45

Asp Leu Ala Trp Arg Leu Arg Met Asn Phe Pro Tyr Phe Tyr Ile Val

```
                50                  55                  60
Ala Ser Val Met Leu Asn Val Arg Leu Gln Val Arg Ile Glu
65                  70                  75
```

<210> SEQ ID NO 20
<211> LENGTH: 78
<212> TYPE: PRT
<213> ORGANISM: Microcebus murinus

<400> SEQUENCE: 20

```
Met Ala Ala Ser Ala Ala Leu Ser Ala Ala Ala Ala Ala Leu
1               5                   10                  15

Ser Gly Leu Ala Val Arg Leu Ser Arg Ser Ala Ala Arg Ser Ser
                20                  25                  30

Tyr Gly Ala Phe Cys Lys Gly Leu Thr Arg Thr Leu Leu Thr Phe Phe
            35                  40                  45

Asp Leu Ala Trp Arg Leu Arg Met Asn Phe Pro Tyr Phe Tyr Ile Val
        50                  55                  60

Ala Ser Val Met Leu Asn Val Arg Leu Gln Val Arg Ile Glu
65                  70                  75
```

<210> SEQ ID NO 21
<211> LENGTH: 69
<212> TYPE: PRT
<213> ORGANISM: Cavia porcellus

<400> SEQUENCE: 21

```
Met Pro Ala Ala Ala Ala Leu Ser Gly Leu Ala Val Arg Leu Ser Arg
1               5                   10                  15

Ser Ala Ala Val Arg Gly Ser Tyr Gly Ala Phe Cys Lys Gly Leu Thr
                20                  25                  30

Arg Thr Leu Leu Thr Phe Phe Asp Leu Ala Trp Arg Leu Arg Ser Asn
            35                  40                  45

Phe Pro Tyr Phe Tyr Val Val Ala Ser Val Met Leu Asn Val Arg Leu
        50                  55                  60

Gln Val Arg Ile Glu
65
```

<210> SEQ ID NO 22
<211> LENGTH: 15
<212> TYPE: PRT
<213> ORGANISM: Artificial Sequence
<220> FEATURE:
<223> OTHER INFORMATION: flexible linker

<400> SEQUENCE: 22

```
Gly Gly Gly Gly Ser Gly Gly Gly Ser Gly Gly Gly Gly Ser
1               5                   10                  15
```

MICROPEPTIDES AND USES THEREOF

FIELD OF THE INVENTION

The present invention is comprised within the field of biomedicine. It specifically relates to micropeptides and the use thereof in the treatment of cancer.

BACKGROUND OF INVENTION

Cancer is one of the leading causes of morbidity and mortality worldwide. It is now responsible for almost one in six deaths globally and the number of new cases is expected to rise by about 70% over the next 2 decades.

Cancer is a group of diseases characterized by uncontrolled cell division (or by an increase of survival or apoptosis resistance) and by the ability of said cells to invade other neighboring tissues (invasion) and spread to other areas of the body where the cells are not normally located (metastasis). Depending on whether or not they can spread by invasion and metastasis, tumours are classified as being either benign or malignant: Benign tumours are tumours that cannot spread by invasion or metastasis, i.e., they only grow locally; whereas malignant tumours are tumours that are capable of spreading by invasion and metastasis.

There are several types of cancers that can be classified by the type of cell in which it originates and by the location of the cell, i.e., carcinomas, which arise from the cells that cover external and internal body surface, e.g. skin, digestive tract or gland; leukaemia, which starts in blood-forming tissue such as the bone marrow, and causes large numbers of abnormal blood cells to be produced and enter into the bloodstream; lymphoma, which is a cancer originating in lymph nodes and tissues of the body's immune system; melanoma, which arises in melanocytes; sarcoma, which begins in the connective tissue of bone or muscle; and teratoma, which begins within germ cells.

Many drugs are now available to be used in the treatment of cancer. However, in many cases the cancer fails to respond to the anti-cancer therapy or its growth and/or metastasis is only slowed. Even when a tumor initially responds to an anti-cancer therapy by decreasing in size or going into remission, the tumor often develops resistance to the drug. For these reasons, there is a need for new anti-cancer agents and drugs which can be used to treat cancers for which there is still no treatment available and for multi-drug resistance cancers.

SUMMARY OF THE INVENTION

The authors of the invention have found that the three long non-coding RNAs (LncRNAs) Linc00086, TINCR and ZEB2AS1 contain regions coding for micropeptides and that said micropeptides have tumor suppressor activities. Hence, the invention relates to the provision of micropeptides with the capacity to act as anti-cancer drugs. Although LncRNAs are known as heterogeneous group of transcripts of over 200 bp that are expressed in tissue- and species-specific manner, most of them remain functionally uncharacterized.

Thus, in a first aspect the invention relates to a micropeptide comprising the amino acid sequence selected from the group consisting of SEQ ID NO: 1, 2 and 3 or a functionally equivalent variant thereof.

In a second aspect the invention relates to an antibody which is capable of specifically binding to the micropeptides of the invention.

In a third aspect the invention relates to a polynucleotide encoding the micropeptide of the invention, with the proviso that said polynucleotide is not a polynucleotide consisting of or comprising the sequence having the NCBI accession number NM_203306.2 corresponding to the version of 10 Sep. 2017, a polynucleotide consisting of or comprising the sequence having the NCBI accession number NR_027064 corresponding to the version of 29 Aug. 2017 and a polynucleotide consisting of or comprising the sequence having the NCBI accession number NR_040248 corresponding to the version of 23 Apr. 2017.

In a fourth aspect, the invention relates to an expression vector comprising the polynucleotide encoding the micropeptide of the invention.

In a fifth aspect, the invention also relates to a host cell comprising the polynucleotide encoding the micropeptide of the invention or the expression vector comprising the polynucleotide encoding the micropeptide of the invention.

In a sixth aspect the invention relates to a composition comprising the micropeptide, the polynucleotide, the expression vector, or the host cell of the invention.

In a seventh aspect the invention also relates to a pharmaceutical composition comprising the composition of the invention and a pharmaceutically acceptable carrier.

In an eighth aspect the invention relates to the micropeptide, the polynucleotide, the expression vector, the host cell, the composition or the pharmaceutical composition of the invention for use in medicine.

In a further aspect, the invention relates to the micropeptide, the polynucleotide, the expression vector, the host cell, the composition or the pharmaceutical composition of the invention for use in the treatment of cancer.

Finally, in another aspect, the invention relates to the micropeptide of SEQ ID NO:2, the polynucleotide encoding said micropeptide, the expression vector, the host cell, the composition or the pharmaceutical composition of the invention for use in the treatment of fibrosis.

DESCRIPTION OF THE FIGURES

FIG. 2. In silico analysis of the micropeptide of SEQ ID NO: 2 micropeptide. (A) Amino acid sequence alignment of SEQ ID NO: 2 micropeptide orthologues. (B) Three-dimensional structure prediction of SEQ ID NO: 2 micropeptide, (iTasser software).

FIG. 6. Micropeptide of sequence SEQ ID NO: 1 expression induces cell death upon cellularstress. SkBR-3, HPAF II, MIA PaCa-2 and BxPC-3 cells were infected with empty or SEQ ID NO: 1-HA retroviruses, and selected by puromycin. Micropeptide of sequence SEQ ID NO: 1 expression was analyzed by qPCR (A) and by Western blot (B). (C) Phase contrast images of the indicated cells 3 days after selection with puromycin. (D) Annexin-V/PI staining of BxPC-3 infected cells with and without puromycin treatment, analyzed by Flow Cytometry. (E) BXPC-3 cells were infected with an inducible lentivirus encoding SEQ ID NO: 1-HA, and selected with Neomycin. Micropeptide of sequence SEQ ID NO: 1 expression was induced by doxycycline, and cells were treated with Doxorubicin or Actinomycin D. (E) Cell viability of the indicated cells measured by crystal violet staining.

FIG. 8. SEQ ID NO: 1 overexpression reduces cell proliferation. A549 and H10 cells were transduced with an inducible lentivirus coding HA-SEQ ID NO: 1. SEQ ID NO: 1 expression was induced by doxycycline treatment for 14 days. (A) Growth curve of transduced cells over 14 days of SEQ ID NO:1 expression. (B) Cell cycle analysis by flow cytometry. Left, histogram plots. Right, quantification of the number of cells in every cell cycle phase. Graphs show the mean±SD, using at least 3 technical replicates. **** P<0.0001, two-tailed t-test.

FIG. 9. SEQ ID NO: 1 overexpression impairs invasiveness and reduces mesenchymal traits in A549 and H10 cell lines. Invasion of indicated cells was analyzed in matrigel-coated inserts. (A) The undersides of membrane inserts containing invaded cells were fixed and stained with crystal violet and photographed 24 h after plating. (B) Number of invasive cells was calculated using ImageJ software. Bars plots show relative number of cells invading the chamber. (C) Analysis of several mesenchymal genes by qPCR. mRNA expression is shown relative to the control. * P<0.05, **P<0.01 two-tailed t-test.

FIG. 11. Micropeptide of sequence SEQ ID NO: 1 expression changes cell ubiquitylation pattern. (A) Co-Immunoprecipitation using Anti-HA and Western Blot experiments indicate the presence of ubiquitylated proteins in the pull down of SEQ ID NO: 1 expressing cells. (B) Analysis of ubiquitylated protein levels by Western Blot in SEQ ID NO: 1 or empty vector BxPC-3 infected cells after proteasome blocking treatment with MG132.

FIG. 12. (A) Micropeptide of SEQ ID NO:2 mRNA expression in IMR90, MIA PaCa-2 and BxPC-3 cell lines infected with the micropeptide of SEQ ID NO: 2 or empty vector, analyzed by qPCR. Values are relative to cells expressing the empty vector as a control. Bars correspond to average±SD. (B) Western Blot against HA-tag in IMR90, MIA PaCa-2 and BxPC-3 cells infected with the micropeptide of SEQ ID NO: 2 or empty vector.

FIG. 14. The micropeptide of SEQ ID NO: 2 subcellular localization in BxPC-3 cell line. Immunostaining showing the micropeptide of SEQ ID NO: 2 cytoplasmatic localization, using a custom made anti-SEQ ID NO:2 antibody. Nuclei are counterstained with DAPI.

FIG. 18. Expression of the micropeptide of SEQ ID NO: 2 impairs cell invasion in pancreatic cancer cells. (A) Invasion of BxPC-3 cells transduced with micropeptide of SEQ ID NO: 2 or empty vector across matrigel-covered inserts. Representative pictures of invading cells 24 hours after seeding. (B) Relative number of invading cells. Bars represent the average of two independent experiments±SD (n=2), as relative to invading cells in the empty vector conditions. * p<0.05, using Student's t-test.

FIG. 19. Expression of the micropeptide of SEQ ID NO: 2 reduces pro-tumoral activity of mCAFs cells. (A) Invasion of WT PDAC pancreatic cancer cells across matrigel-covered inserts where mCAFs expessing the micropeptide of SEQ ID NO: 2 or empty vector were seeded in the bottom compartment of the Boyden chambers. Representative pictures of invading cells 24 hours after seeding. (B) Relative number of invading cells.±SD (n=3 technical replicates), as relative to invading cells in the empty vector conditions.

FIG. 22. Expression of the micropeptide of SEQ ID NO: 2 reduces cell invasion of breast cancer cells. (A) Invasion of MDA-MB-231 breast cancer cells transduced with micropeptide of SEQ ID NO: 2 or empty vector across matrigel-covered inserts. Representative pictures of invading cells 24 hours after seeding. (B) Relative number of invading cells±SD (n=3 technical replicates), as relative to invading cells in the empty vector conditions. * p<0.05, using Student's t-test.

FIG. 23. Overexpression of the micropeptide of SEQ ID NO: 3 in cancer cell lines. (A) Analysis of SEQ ID NO: 3 overexpression by qPCR in A459 cells. (B) Detection of SEQ ID NO: 3 micropeptide expression in A459 cells by Western blot. (C) Phase contrast images of the indicated cell lines after SEQ ID NO: 3 overexpression.

FIG. 25. SEQ ID NO: 3 is transcriptionally upregulated upon genotoxic stress by p53. (A) HCT116 and HCT116 p53KO cells were treated with MDM2 inhibitor Nutlin3a (10 μM) during 48 h. SEQ ID NO: 3 transcriptional levels were tested by RT-qPCR. mRNA levels are normalized to untreated control (B) HCT116 and HCT116 p53KO cells were treated with genotoxic agent Doxorubicin (1 μM) during 24 h. SEQ ID NO: 3 mRNA levels were tested by RT-qPCR. mRNA levels are presented relative to GAPDH reference gene. Bars represent average of n=3 technical replicates±SD.

DETAILED DESCRIPTION OF THE INVENTION

Figure 1:
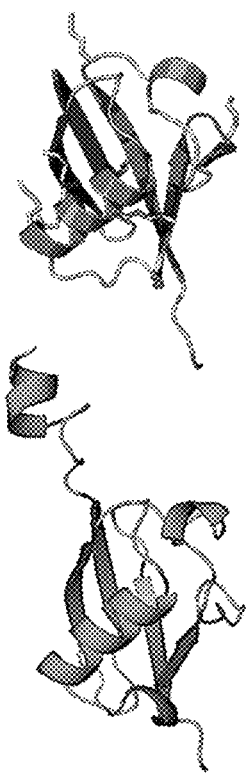
FIG. 1. In silico analysis of the micropeptide of SEQ ID NO: 1 micropeptide. (A) Amino acid sequence conservation of SEQ ID NO: 1 micropeptide across mammals (primates and rodents). (B) Three-dimensional structure prediction of SEQ ID NO: 1 micropeptide, (iTasser software) and comparison to Ubiquitin structure.

The present invention relates to the provision of new compounds for the treatment of cancer.

The Micropeptides of SEQ ID NO: 1, 2 and 3

In a first aspect the invention relates to a micropeptide comprising the amino acid sequence selected from the group consisting of SEQ ID NO: 1, 2 and 3 or a functionally equivalent variant thereof.

The term "micropeptide", as used herein, is used to refer to peptides having from 4 to 100 amino acids, preferably from 20 to 90 amino acids. They can be of natural or synthetic origin. In nature, they are coded by an open reading frame contained in a lncRNA, in a RNA molecule annotated as non-protein coding, or in a RNA molecule annotated as "intergenic region".

The term "open reading frame" corresponds to a nucleotide sequence in a DNA or RNA molecule that may potentially encode a peptide or a protein. Said open reading frame begins with a start codon (the start codon generally encoding a methionine), followed by a series of codons (each codon encoding an amino acid), and ends with a stop codon (the stop codon not being translated). The term "long non-coding RNA" or "lncRNA" as used herein includes a transcript longer than 200 nucleotides and annotated as non-coding.

The terms "polypeptide" and "peptide" are used interchangeably herein to refer to polymers of amino acids of any length. The polymer can be linear or branched, it can comprise modified amino acids, and it can be interrupted by non-amino acids.

The term "amino acid" refers to naturally occurring and synthetic amino acids, as well as amino acid analogs and amino acid mimetics that function in a manner similar to the naturally occurring amino acids. Furthermore, the term "amino acid" includes both D- and L-amino acids (stereoisomers).

The term "natural amino acids" or "naturally occurring amino acid" comprises the 20 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine.

As used herein the term "non-natural amino acid" or "synthetic amino acid" refers to a carboxylic acid, or a derivative thereof, substituted at position "a" with an amine group and being structurally related to a natural amino acid. Illustrative non-limiting examples of modified or uncommon amino acids include 2-aminoadipic acid, 3-aminoadipic acid, beta-alanine, 2-aminobutyric acid, 4-aminobutyric acid, 6-aminocaproic acid, 2-aminoheptanoic acid, 2-aminoisobutyric acid, 3-aminoisobutyric acid, 2-aminopimelic acid, 2,4-diaminobutyric acid, desmosine, 2,2'-diaminopimelic acid, 2,3-diaminopropionic acid, N-ethylglycine, N-ethylasparagine, hydroxy lysine, alio hydroxy lysine, 3-hydroxyproline, 4-hydroxyproline, isodesmosine, alloisoleucine, N-methylglycine, N-methyliso leucine, 6-N-methyl-lysine, N-methylvaline, norvaline, norleucine, ornithine, etc Tables 1 and 2 below list naturally occurring amino acids (Table 1) and nonconventional or modified amino acids (Table 2) which can be used within the present invention.

TABLE 1

|  | Three-Letter Abbreviation | One-letter Symbol |
|---|---|---|
| alanine | Ala | A |
| Arginine | Arg | R |
| Asparagine | Asn | N |

TABLE 1-continued

|  | Three-Letter Abbreviation | One-letter Symbol |
|---|---|---|
| Aspartic acid | Asp | D |
| Cysteine | Cys | C |
| Glutamine | Gln | Q |
| Glutamic Acid | Glu | E |
| glycine | Gly | G |
| Histidine | His | H |
| isoleucine | Iie | I |
| leucine | Leu | L |
| Lysine | Lys | K |
| Methionine | Met | M |
| phenylalanine | Phe | F |
| Proline | Pro | P |
| Serine | Ser | S |
| Threonine | Thr | T |
| tryptophan | Trp | W |
| tyrosine | Tyr | Y |
| Valine | Val | V |
| Any amino acid as above | Xaa | X |

TABLE 2

| Non-conventional amino acid | Code | Non-conventional amino acid | Code |
|---|---|---|---|
| α-aminobutyric acid | Abu | L-N-methylalanine | Nmala |
| α-amino-α-methylbutyrate | Mgabu | L-N-methylarginine | Nmarg |
| aminocyclopropane-carboxylate | Cpro | L-N-methylasparagine | Nmasn |
|  |  | L-N-methylaspartic acid | Nmasp |
| aminoisobutyric acid | Aib | L-N-methylcysteine | Nmcys |
| aminonorbornyl-carboxylate | Norb | L-N-methylglutamine | Nmgin |
|  |  | L-N-methylglutamic acid | Nmglu |
| cyclohexylalanine | Chexa | L-N-methylhistidine | Nmhis |
| cyclopentylalanine | Cpen | L-N-methylisolleucine | Nmile |
| D-alanine | Dal | L-N-methylleucine | Nmleu |
| D-arginine | Darg | L-N-methyllysine | Nmlys |
| D-aspartic acid | Dasp | L-N-methylmethionine | Nmmet |
| D-cysteine | Dcys | L-N-methylnorleucine | Nmnle |
| D-glutamine | Dgln | L-N-methylnorvaline | Nmnva |
| D-glutamic acid | Dglu | L-N-methylornithine | Nmorn |
| D-histidine | Dhis | L-N-methylphenylalanine | Nmphe |
| D-isoleucine | Dile | L-N-methylproline | Nmpro |
| D-leucine | Dleu | L-N-methylserine | Nmser |
| D-lysine | Dlys | L-N-methylthreonine | Nmthr |
| D-methionine | Dmet | L-N-methyltryptophan | Nmtrp |
| D-ornithine | Dorn | L-N-methyltyrosine | Nmtyr |
| D-phenylalanine | Dphe | L-N-methylvaline | Nmval |
| D-proline | Dpro | L-N-methylethylglycine | Nmetg |
| D-serine | Dser | L-N-methyl-t-butylglycine | Nmtbug |
| D-threonine | Dthr | L-norleucine | Nle |
| D-tryptophan | Dtrp | L-norvaline | Nva |
| D-tyrosine | Dtyr | α-methyl-aminoisobutyrate | Maib |
| D-valine | Dval | α-methyl-Y-aminobutyrate | Mgabu |
| D-α-methylalanine | Dmala | α ethylcyclohexylalanine | Mchexa |
| D-α-methylarginine | Dmarg | α-methylcyclopentylalanine | Mcpen |
| D-α-methylasparagine | Dmasn | α-methyl-α-napthylalanine | Manap |
| D-α-methylaspartate | Dmasp | α-methylpenicillamine | Mpen |
| D-α-methylcysteine | Dmcys | N-(4-aminobutyl)glycine | Nglu |
| D-α-methylglutamine | Dmgln | N-(2-aminoethyl)glycine | Naeg |
| D-α-methylhistidine | Dmhis | N-(3-aminopropyl)glycine | Norn |
| D-α-methylisoleucine | Dmile | N-amino-α-methylbutyrate | Nmaabu |
| D-α-methylleucine | Dmleu | α-napthylalanine | Anap |
| D-α-methyllysine | Dmlys | N-benzylglycine | Nphe |
| D-α-methylmethionine | Dmmet | N-(2-carbamylethyl)glycine | Ngln |
| D-α-methylornithine | Dmorn | N-(carbamylmethyl)glycine | Nasn |
| D-α-methylphenylalanine | Dmphe | N-(2-carboxyethyl)glycine | Nglu |
| D-α-methylproline | Dmpro | N-(carboxymethyl)glycine | Nasp |
| D-α-methylserine | Dmser | N-cyclobutylglycine | Ncbut |
| D-α-methylthreonine | Dmthr | N-cycloheptylglycine | Nchep |
| D-α-methyltryptophan | Dmtrp | N-cyclohexylglycine | Nchex |
| D-α-methyltyrosine | Dmty | N-cyclodecylglycine | Ncdec |
| D-α-methylvaline | Dmval | N-cyclododeclglycine | Ncdod |
| D-α-methylalnine | Dnmala | N-cyclooctylglycine | Ncoct |
| D-α-methylarginine | Dnmarg | N-cyclopropylglycine | Ncpro |
| D-α-methylasparagine | Dnmasn | N-cycloundecylglycine | Ncund |
| D-α-methylasparatate | Dnmasp | N-(2,2-diphenylethyl)glycine | Nbhm |
| D-α-methylcysteine | Dnmcys | N-(3,3-diphenylpropyl)glycine | Nbhe |
| D-N-methylleucine | Dnmleu | N-(3-indolylyethyl) glycine | Nhtrp |
| D-N-methyllysine | Dnmlys | N-methyl-Y-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nile | D-N-methylserine | Dnmser |

TABLE 2-continued

| Non-conventional amino acid | Code | Non-conventional amino acid | Code |
|---|---|---|---|
| N-(2-methylpropyl)glycine | Nleu | D-N-methylthreonine | Dnmthr |
| D-N-methyltryptophan | Dnmtrp | N-(1-methylethyl)glycine | Nva |
| D-N-methyltyrosine | Dnmtyr | N-methyla-napthylalanine | Nmanap |
| D-N-methylvaline | Dnmval | N-methylpenicillamine | Nmpen |
| Y-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α thylglutamine | Mgln | L-α-methylglutamate | Mglu |
| L-α-methylhistidine | Mhis | L-α-methylhomo phenylalanine | Mhphe |
| L-α-methylisoleucine | Mile | N-(2-methylthioethyl)glycine | Nmet |
| D-N-methylglutamine | Dnmgln | N-(3-guanidinopropyl)glycine | Narg |
| D-N-methylglutamate | Dnmglu | N-(1-hydroxyethyl)glycine | Nthr |
| D-N-methylhistidine | Dnmhis | N-(hydroxyethyl)glycine | Nser |
| D-N-methylisoleucine | Dnmile | N-(imidazolylethyl)glycine | Nhis |
| D-N-methylleucine | Dnmleu | N-(3-indolylyethyl)glycine | Nhtrp |
| D-N-methyllysine | Dnmlys | N-methyl-Y-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nval |
| D-N-methyltyrosine | Dnmtyr | N-methyla-napthylalanine | Nmanap |
| D-N-methylvaline | Dnmval | N-methylpenicillamine | Nmpen |
| Y-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α ethylhistidine | Mhis | L-α-methylhomophenylalanine | Mhphe |
| L-α thylisoleucine | Mile | N-(2-methylthioethyl)glycine | Nmet |
| L-α-methylleucine | Mleu | L-α-methyllysine | Mlys |
| L-α-methylmethionine | Mmet | L-α-methylnorleucine | Mnle |
| L-α-methylnorvaline | Mnva | L-α-methylornithine | Morn |
| L-α-methylphenylalanine | Mphe | L-α-methylproline | Mpro |
| L-α-methylserine | mser | L-α-methylthreonine | Mthr |
| L-α ethylvaline | Mtrp | L-α-methyltyrosine | Mtyr |
| L-α-methylleucine | Mval Nnbhm | L-N-methylhomophenylalanine | Nmhphe |
| N-(N-(2,2-diphenylethyl) carbamylmethyl-glycine | Nnbhm | N-(N-(3,3-diphenylpropyl) carbamylmethyl(1)glycine | Nnbhe |
| 1-carboxy-1-(2,2-diphenyl ethylamino)cyclopropane | Nmbc | | |

"Functionally equivalent variant" is understood to mean all those micropeptides derived from the sequences SEQ ID NO: 1, 2 or 3, by modification, substitution, insertion and/or deletion of one or more amino acids, whenever the function is substantially maintained.

Preferably, "variants" of sequences SEQ ID NO:1, 2 or 3 are (i) micropeptides in which one or more amino acid residues are substituted by a conserved or non-conserved amino acid residue (preferably a preserved amino acid residue) and such substituted amino acid may be coded or not by the genetic code, (ii) micropeptides in which there is one or more modified amino acid residues, for example, residues modified by substituent bonding, (iii) micropeptides resulting from alternative processing of a similar mRNA, (iv) micropeptide fragments and/or (v) micropeptides resulting from the fusion of sequences SEQ ID NO: 1, 2 or 3 or of the variants defined above in (i) to (iii) with another polypeptide, such as a secretory leader sequence, a sequence being used for purification (for example, His tag), for detection (for example, Sv5 epitope tag) or for delivery to a specific target cell. The fragments include polypeptides generated through proteolytic cut (including multisite proteolysis) of an original sequence. The functionally equivalent variant may be the result of a post-translationally or chemically modification. Such variants will be apparent to those skilled in the art.

The variants of sequences SEQ ID NO: 1, 2 or 3 may be both natural and artificial. The expression "natural variant" relates to all those variants of human SEQ ID NO: 1, 2 or 3 which appear naturally in other species, i.e. the orthologues of SEQ ID NO: 1. 2 or 3.

A functionally equivalent variant of sequences SEQ ID NO: 1, 2 or 3 can be an amino acid sequence derived from sequences SEQ ID NO: 1, 2 or 3 comprising the addition, substitution or modification of one or more amino acid residues. By way of illustration, functionally equivalent variants of the sequences SEQ ID NO: 1, 2 or 3 include sequences comprising the addition of 1 amino acid, 2 amino acids, 3 amino acids, 4 amino acids, 5 amino acids, 10 amino acids, 15 amino acids, 20 amino acids, 25 amino acids, 30 amino acids, 35 amino acids, 40 amino acids, 45 amino acids, 50 amino acids, 60 amino acids, 70 amino acids, 80 amino acids, 90 amino acids, 100 amino acids, 150 amino acids, 200 amino acids, at least 500 amino acids, at least 1000 amino acids or more at the amino terminus of the sequence SEQ ID NO: 1, 2 or 3, and/or comprising the addition of 1 amino acid, 2 amino acids, 3 amino acids, 4 amino acids, 5 amino acids, amino acids, 1 1 amino acids, 12 amino acids, 13 amino acids, 14 amino acids, 15 amino acids, 20 amino acids, 25 amino acids, 30 amino acids, 35 amino acids, 40 amino acids, 45 amino acids, 50 amino acids, 60 amino acids, 70 amino acids, 80 amino acids, 90 amino acids, 100 amino acids, 150 amino acids, 200 amino acids, at least 500 amino acids, at least 1000 amino acids or more at the carboxy terminus of the sequences SEQ ID NO: 1, 2 or 3, and maintaining at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or at least 100% of the activity of the sequences SEQ ID NO: 1, 2 or 3.

The term "conservative substitution" or "conserved amino acid residue" as used herein, refers to the replacement of an amino acid present in the native sequence in the peptide with a naturally or non-naturally occurring amino acid or a peptidomimetics having similar steric properties. Where the side-chain of the native amino acid to be replaced is either polar or hydrophobic, the conservative substitution should be with a naturally occurring amino acid, a non-naturally occurring amino acid or with a peptidomimetic moiety which is also polar or hydrophobic (in addition to having the same steric properties as the side-chain of the replaced amino acid).

As naturally occurring amino acids are typically grouped according to their properties, conservative substitutions by naturally occurring amino acids can be easily determined bearing in mind the fact that in accordance with the invention replacement of charged amino acids by sterically similar non-charged amino acids are considered as conservative substitutions.

For producing conservative substitutions by non-naturally occurring amino acids it is also possible to use amino acid analogs (synthetic amino acids) well known in the art.

When affecting conservative substitutions the substituting amino acid should have the same or a similar functional group in the side chain as the original amino acid.

The phrase "non-conservative substitutions" or "non-conserved amino acid residue" as used herein refers to replacement of the amino acid as present in the parent sequence by another naturally or non-naturally occurring amino acid, having different electrochemical and/or steric properties. Thus, the side chain of the substituting amino acid can be significantly larger (or smaller) than the side chain of the native amino acid being substituted and/or can have functional groups with significantly different electronic properties than the amino acid being substituted. Examples of non-conservative substitutions of this type include the substitution of phenylalanine or cycohexylmethyl glycine for alanine, isoleucine for glycine, or —NH—CH[(—CH2)5-COOH]—CO— for aspartic acid. Those non-conservative substitutions which fall under the scope of the present invention are those which still constitute a peptide having anti-proliferative properties.

The peptides of the present invention may also comprise non-amino acid moieties, such as for example, hydrophobic moieties (various linear, branched, cyclic, polycyclic or heterocyclic hydrocarbons and hydrocarbon derivatives) attached to the peptides; various protecting groups, especially where the compound is linear, which are attached to the compound's terminals to decrease degradation. Suitable protecting functional groups are described in Green and Wuts, "Protecting Groups in Organic Synthesis", John Wiley and Sons, Chapters 5 and 7, 1991.

Chemical (non-amino acid) groups present in the compound may be included in order to improve various physiological properties such; decreased degradation or clearance; decreased repulsion by various cellular pumps, improve immunogenic activities, improve various modes of administration (such as attachment of various sequences which allow penetration through various barriers, through the gut, etc.); increased specificity, increased affinity, increased stability, bioavailability, solubility, decreased toxicity and the like.

The variants of the invention can encompass native peptides (either degradation products, synthetically synthesized peptides or recombinant peptides), analogs, derivatives, salts, retro-inverso isomers, mimics, mimetics, or peptidomimetics (typically, synthetically synthesized peptides), as well as peptoids and semipeptoids. "Analog", "derivative" and "mimetic" include molecules which mimic the chemical structure of a peptidic structure and retain the functional properties of the peptidic structure. Approaches to designing peptide analogs, derivatives and mimetics are known in the art. For example, see Farmer, P. S. in Dmg Design (E. J. Ariens, ed.) Academic Press, New York, 1980, vol. 10, pp. 119-143; Ball, J. B. and Alewood, P. F. (1990) J. Mol. Recognition 3:55. Morgan, B. A. and Gainor, J. A. (1989) Ann. Rep. Med. Chem. 24:243; and Freidinger, R. M. (1989) Trends Pharmacol. Sci. 10:270. See also Sawyer, T. K. (1995) Peptidomimetic Design and Chemical Approaches to Peptide Metabolism in Taylor, M. D. and Amidon, G. L. (eds.) Peptide-Based Drug Design: Controlling Transport and Metabolism, Chapter 17; Smith, A. B. 3rd, et al. (1995) J. Am. Chem. Soc. 117: 11113-11123; Smith, A. B. 3rd, et al. (1994) J. Am. Chem. Soc. 116:9947-9962; and Hirschman, R., et al. (1993) J. Am. Chem. Soc. 115: 12550-12568.

A "derivative" (e.g., a peptide or amino acid) includes forms in which one or more reaction groups on the compound have been derivatized with a substituent group. Examples of peptide derivatives include peptides in which an amino acid side chain, the peptide backbone, or the amino- or carboxy-terminus has been derivatized (e.g., peptidic compounds with methylated amide linkages). An "analog" of a compound X includes compounds which retain chemical structures necessary for functional activity, yet which also contains certain chemical structures which differ. An example of an analog of a naturally-occurring peptide is a peptide which includes one or more non-naturally-occurring amino acids.

A "mimetic" of a compound includes compounds in which chemical structures of the compound necessary for functional activity have been replaced with other chemical structures which mimic the conformation of the compound. Examples of peptidomimetics include peptidic compounds in which the peptide backbone is substituted with one or more benzodiazepine molecules (see e.g., James, G. L. et al. (1993) Science 260: 1937-1942) or oligomers that mimics peptide secondary structure through use of amide bond isosteres and/or modification of the native peptide backbone, including chain extension or heteroatom incorporation; examples of which include azapeptides, oligocarbamates, oligoureas, beta-peptides, gamma-peptides, oligo (phenylene ethynylene)s, vinylogous sulfonopeptides, poly-N-substituted glycines (peptoids) and the like. Methods for preparing peptidomimetic compounds are well known in the art and are specified, for example, in Quantitative Drug Design, C. A. Ramsden Gd., Chapter 17.2, F. Choplin Pergamon Press (1992).

In addition to the above, the micropeptides of the present invention may also include one or more modified amino acids or one or more non-amino acid monomers (e.g. fatty acids, complex carbohydrates etc).

The present teachings further contemplate cyclic peptides or cyclic structures within the peptides. Methods of cyclization are well known in the art, see for instance in WO2010/041237.

The micropeptides of the present invention can be biochemically synthesized such as by using standard solid phase techniques. These methods include exclusive solid phase synthesis, partial solid phase synthesis methods, fragment condensation, classical solution synthesis. Solid phase polypeptide synthesis procedures are well known in the art and further described by John Morrow Stewart and Janis Dillaha Young, Solid Phase Polypeptide Syntheses (2nd Ed., Pierce Chemical Company, 1984).

Synthetic peptides can be purified by preparative high performance liquid chromatography (Creighton T. (1983) Proteins, structures and molecular principles. WH Freeman and Co. NY) and the composition of which can be confirmed via amino acid sequencing.

Recombinant techniques may also be used to generate the micropeptides of the present invention. To produce a peptide of the present invention using recombinant technology, a polynucleotide encoding the micropeptide of the present invention is ligated into a nucleic acid expression vector, which comprises the polynucleotide sequence under the transcriptional control of a cis-regulatory sequence (e.g., promoter sequence) suitable for directing constitutive, tissue specific or inducible transcription of the monomers of the present invention in the host cells.

In addition to being synthesizable in host cells, the peptides of the present invention can also be synthesized using in vitro expression systems. These methods are well known in the art and the components of the system are commercially available.

The activity or function of the sequences SEQ ID NO: 1, 2 or 3 and their functionally equivalent variants can be determined, by assaying the anti-proliferative activity of the peptides by a method shown in the examples of the present application.

Functional equivalent variants of sequences SEQ ID NO: 1, 2 or 3 also include amino acid sequences with a sequence identity of at least 70%, at least 75%, at least 80%, at least 85%, at least 90%, at least 91%, at least 92%, at least 93%, at least 94%, at least 95%, at least 96%, at least 97%, at least 98%, or at least 99% with the sequences SEQ ID NO: 1, 2 or 3.

In a particular embodiment the functionally equivalent variant of the micropeptide of the invention has a sequence which shows at least 80% identity with the sequence of SEQ ID NO:1, 2 or 3. The terms "identity", "identical" or "percent identity" in the context of two or more amino acid or nucleotide sequences, refer to two or more sequences or subsequences that are the same or have a specified percentage of amino acid residues that are the same, when compared and aligned (introducing gaps, if necessary) for maximum correspondence, not considering any conservative amino acid substitutions as part of the sequence identity. The percent identity can be measured using sequence comparison software or algorithms or by visual inspection. Various algorithms and software are known in the art that can be used to obtain alignments of amino acid or nucleotide sequences. One such non-limiting example of a sequence alignment algorithm is the algorithm described in Karlin et al., 1990, Proc. Natl. Acad. Sci., 87:2264-8, as modified in Karlin et al., 1993, Proc. Natl. Acad. Sci., 90:5873-7, and incorporated into the N BLAST and XBLAST programs (Altschul et al., 1997, Nucleic Acids Res., 25:3389-402). In certain embodiments, Gapped BLAST can be used as described in Altschul et al., 1997, Nucleic Acids Res. 25:3389-402. BLAST-2, WU-BLAST-2 (Altschul et al., 1996, Methods in Enzymology, 266:460-80), ALIGN, ALIGN-2 (Genentech, South San Francisco, California) or Megalign (DNASTAR) are additional publicly available software programs that can be used to align sequences. In certain embodiments, the percent identity between two nucleotide sequences is determined using the GAP program in GCG software (e.g., using a NWSgapdna.CMP matrix and a gap weight of 40, 50, 60, 70, or 90 and a length weight of 1, 2, 3, 4, 5, or 6). In certain alternative embodiments, the GAP program in the GCG software package, which incorporates the algorithm of Needleman and Wunsch (J. Mol. Biol. 48:444-53 (1970)) can be used to determine the percent identity between two amino acid sequences (e.g., using either a Blossum 62 matrix or a PAM250 matrix, and a gap weight of 16, 14, 12, 10, 8, 6, or 4 and a length weight of 1, 2, 3, 4, 5). Alternatively, in certain embodiments, the percent identity between nucleotide or amino acid sequences is determined using the algorithm of Myers and Miller (CABIOS, 4:1 1-7 (1989)). For example, the percent identity can be determined using the ALIGN program (version 2.0) and using a PAM120 with residue table, a gap length penalty of 12 and a gap penalty of 4. Appropriate parameters for maximal alignment by particular alignment software can be determined by one skilled in the art. In certain embodiments, the default parameters of the alignment software are used. In certain embodiments, the percentage identity "X" of a first amino acid sequence to a second amino acid sequence is calculated as $100 \times (Y/Z)$, where Y is the number of amino acid residues scored as identical matches in the alignment of the first and second sequences (as aligned by visual inspection or a particular sequence alignment program) and Z is the total number of residues in the second sequence. If the second sequence is longer than the first sequence, then the global alignment taken the entirety of both sequences into consideration is used, therefore all letters and null in each sequence must be aligned. In this case, the same formula as above can be used but using as Z value the length of the region wherein the first and second sequence overlaps, said region having a length which is substantially the same as the length of the first sequence.

As a non-limiting example, whether any particular polynucleotide or polypeptide has a certain percentage sequence identity (e.g., is at least 80% identical, at least 85% identical, at least 90% identical, and in some embodiments, at least 95%, 96%, 97%, 98%, or 99% identical) to a reference sequence can, in certain embodiments, be determined using the Bestfit program (Wisconsin Sequence Analysis Package, Version 8 for Unix, Genetics Computer Group, University Research Park, 575 Science Drive, Madison, WI 5371 1). Bestfit uses the local homology algorithm of Smith and Waterman, Advances in Applied Mathematics 2:482-9 (1981), to find the best segment of homology between two sequences. When using Bestfit or any other sequence alignment program to determine whether a particular sequence is, for instance, 95% identical to a reference sequence according to the present invention, the parameters are set such that the percentage of identity is calculated over the full length of the reference amino acid sequence and that gaps in homology of up to 5% of the total number of nucleotides in the reference sequence are allowed.

In some embodiments, two amino acid sequences are substantially identical, meaning they have at least 70%, at least 75%, at least 80%, at least 85%, at least 90%, and in some embodiments at least 95%, 96%, 97%, 98%, 99% amino acid residue identity, when compared and aligned for maximum correspondence, as measured using a sequence comparison algorithm or by visual inspection. Identity can exist over a region of the sequences that is at least about 10, about 20, about 40-60 residues in length or any integral value therebetween, and can be over a longer region than 60-80 residues, for example, at least about 90-100 residues, and in some embodiments, the sequences are substantially identical over the full length of the sequences being compared.

Antibodies Against the Micropeptides of the Invention

In another aspect the invention relates to an antibody which is capable of specifically binding to the micropeptides of the invention.

As used herein, the term "antibody" relates to a monomeric or multimeric protein which comprises at least one polypeptide having the capacity for binding to a determined antigen, or epitope within the antigen, and comprising all or part of the light or heavy The term antibody also includes any type of known antibody, such as, for example, polyclonal antibodies, monoclonal antibodies and genetically engineered antibodies, such as chimeric antibodies, humanized antibodies, primatized antibodies, human antibodies and bispecific antibodies (including diabodies), multispecific antibodies (e.g. bispecific antibodies), and antibody fragments so long as they exhibit the desired biological activity.

The invention also comprises the use of fragments of the different types of antibodies mentioned above which substantially preserve the anti-angiogenic activity of the antibody. The term "antibody fragment" includes antibody fragments such as Fab, F(ab')2, Fab', single chain Fv fragments (scFv), diabodies and nanobodies.

The phrase "specifically binds" when referring to antibodies and antigen binding fragments thereof means that the antibody binds to the micropeptides of the invention or variants thereof with no or insignificant binding to other human proteins. The term however does not exclude the fact that antibodies of the invention may also be cross-reactive with other forms of the micropeptides of the invention. Typically, the antibody binds with an association constant (Kd) of at least about $1\times10^{-6}$ M or $10^{-7}$ M, or about $10^{-8}$ M to $10^{-9}$ M, or about $10^{-10}$ M to $10^{-11}$ M or higher, and binds to the predetermined antigen with an affinity that is at least two-fold greater than its affinity for binding to a non-specific antigen (e.g., BSA, casein) other than the predetermined antigen or a closely-related antigen. The phrases "an antibody recognizing an antigen" and "an antibody specific for an antigen" are used interchangeably herein with the term "an antibody which binds specifically to an antigen".

The phrase "specifically bind(s)" or "bind(s) specifically" when referring to a peptide refers to a peptide molecule which has intermediate or high binding affinity, exclusively or predominately, to a target molecule. The phrase "specifically binds to" refers to a binding reaction that is determinative of the presence of a target protein in the presence of a heterogeneous population of proteins and other biologics. Thus, under designated assay conditions, the specified binding moieties bind preferentially to a particular target protein and do not bind in a significant amount to other components present in a test sample. Specific binding to a target protein under such conditions may require a binding moiety that is selected for its specificity for a particular target antigen. A variety of assay formats may be used to select ligands that are specifically reactive with a particular protein. For example, solid-phase ELISA immunoassays, immunoprecipitation, Biacore, and Western blot are used to identify peptides that specifically react with the micropeptides of the invention or their variants thereof. Typically a specific or selective reaction will be at least twice background signal or noise and more typically more than times background.

Polynucleotides Encoding the Micropeptides of the Invention, and Vectors and Host Cells Containing Said Polynucleotides In a third aspect the invention relates to a polynucleotide encoding the micropeptide of the invention, with the proviso that said polynucleotide is not a polynucleotide consisting of the sequence having the NCBI accession number NM_203306.2 corresponding to the version of 10 Sep. 2017, NR_027064 corresponding to the version of 29 Aug. 2017 and NR_040248 corresponding to the version of 23 Apr. 2017.

As used herein, the term "polynucleotide" refers to a polymer composed of a multiplicity of nucleotide units (deoxyribonucleotides or ribonucleotides, or related structural variants or synthetic analogues thereof) linked via phosphodiester bonds (or related structural variants on synthetic analogues thereof). The term polynucleotide includes double or single stranded genomic and cDNA, RNA, any synthetic and genetically manipulated polynucleotide, and both sense and anti-sense polynucleotide (although only sense stands are being disclosed in the present invention). This includes single- and double-stranded molecules, i.e., DNA-DNA, DNA-RNA and RNA-RNA hybrids.

The polynucleotide of the invention can be found isolated as such or forming part of vectors allowing the propagation of said polynucleotides in suitable host cells. Therefore, in another aspect, the invention relates to a vector, hereinafter vector of the invention, encoding the polynucleotide of the invention as described above.

Vectors suitable for the insertion of said polynucleotide are vectors derived from expression vectors in prokaryotes such as pUC18, pUC19, Bluescript and the derivatives thereof, mpl8, mp19, pBR322, pMB9, CoIEI, pCRI, RP4, phages and "shuttle" vectors such as pSA3 and pAT28; expression vectors in yeasts such as vectors of the type of 2 micron plasmids, integration plasmids, YEP vectors, centromere plasmids and the like; expression vectors in insect cells such as vectors of the pAC series and of the pVL; expression vectors in plants such as pIBI, pEarleyGate, pAVA, pCAMBIA, pGSA, pGWB, pMDC, pMY, pORE series and the like; and expression vectors in eukaryotic cells, including baculovirus suitable for transfecting insect cells using any commercially available baculovirus system. The vectors for eukaryotic cells include preferably viral vectors (adenoviruses, viruses associated to adenoviruses such as retroviruses and, particularly, lentiviruses) as well as non-viral vectors such as pSilencer 4.1-CMV (Ambion), pcDNA3, pcDNA3.1/hyg, pHMCV/Zeo, pCR3.1, pEFI/His, pIND/GS, pRc/HCMV2, pSV40/Zeo2, pTRACER-HCMV, pUB6/V5-His, pVAXI, pZeoSV2, pCl, pSVL and PKSV-10, pBPV-1, pML2d and pTDTI.

The vectors may also comprise a reporter or marker gene which allows identifying those cells that have incorporated the vector after having been put in contact with it.

Useful reporter genes in the context of the present invention include lacZ, luciferase, thymidine kinase, GFP and on the like. Useful marker genes in the context of this invention include, for example, the neomycin resistance gene, conferring resistance to the aminoglycoside G418; the hygromycin phosphotransferase gene, conferring resistance to hygromycin; the ODC gene, conferring resistance to the inhibitor of the ornithine decarboxylase (2-(difluoromethyl)-DL-ornithine (DFMO); the dihydrofolatereductase gene, conferring resistance to methotrexate; the puromycin-N-acetyl transferase gene, conferring resistance to puromycin; the ble gene, conferring resistance to zeocin; the adenosine deaminase gene, conferring resistance to 9-beta-D-xylofuranose adenine; the cytosine deaminase gene, allowing the cells to grow in the presence of N-(phosphonacetyl)-L-aspartate; thymidine kinase, allowing the cells to grow in the presence of aminopterin; the xanthine-guanine phosphoribosyltransferase gene, allowing the cells to grow in the presence of xanthine and the absence of guanine; the trpB gene of *E. coli*, allowing the cells to grow in the presence of indol instead of tryptophan; the hisD gene of *E. coli*, allowing the cells to use histidinol instead of histidine. The selection gene is incorporated into a plasmid that can additionally include a promoter suitable for the expression of said gene in eukaryotic cells (for example, the CMV or SV40 promoters), an optimized translation initiation site (for example, a site following the so-called Kozak's rules or an IRES), a polyadenylation site such as, for example, the SV40 polyadenylation or phosphoglycerate kinase site, introns such as, for example, the beta-globulin gene intron. Alternatively, it is possible to use a combination of both the reporter gene and the marker gene simultaneously in the same vector.

On the other hand, as the skilled person in the art knows, the choice of the vector will depend on the host cell in which it will subsequently be introduced. By way of example, the vector in which said polynucleotide is introduced can also be a yeast artificial chromosome (YAC), a bacterial artificial chromosome (BAC) or a PI-derived artificial chromosome (PAC). The characteristics of the YAC, BAC and PAC are known by the person skilled in the art. Detailed information on said types of vectors has been provided, for example, by Giraldo and Montoliu (Giraldo, P. & Montoliu L., 2001 Size matters: use of YACs, BACs and PACs in transgenic animals, Transgenic Research 10(2): 83-110). The vector of the invention can be obtained by conventional methods known by persons skilled in the art (Sambrook J. et al., 2000 "Molecular cloning, a Laboratory Manual", 3rd ed., Cold Spring Harbor Laboratory Press, N.Y. Vol 1-3).

The polynucleotide of the invention can be introduced into the host cell in vivo as naked DNA plasmids, but also using vectors by methods known in the art, including but not limited to transfection, electroporation (e.g. transcutaneous electroporation), microinjection, transduction, cell fusion, DEAE dextran, calcium phosphate precipitation, use of a gene gun, or use of a DNA vector transporter. See J M Wilson, et al., J. Biol. Chem. 1992; 267:963-967, Wu C and Wu G, Biol. Chem. 1988; 263: 14621-14624, and Williams R, et al., Proc. Natl. Acad. Sci. USA 1991; 88:2726-2730. Methods for formulating and administering naked DNA to mammalian muscle tissue are also known. See Feigner P, et al., U.S. Pat. Nos. 5,580,859, and 5,589,466. Other molecules are also useful for facilitating transfection of a nucleic acid in vivo, such as cationic oligopeptides, peptides derived from DNA binding proteins, or cationic polymers. See Bazile D, et al., WO 1995021931, and BykG, et al., WO 1996025508.

Another well-known method that can be used to introduce polynucleotides into host cells is particle bombardment (aka biolistic transformation). Biolistic transformation is commonly accomplished in one of several ways. One common method involves propelling inert or biologically active particles at cells. See Sanford J, et al., U.S. Pat. Nos. 4,945,050, 5,036,006, and 5,100,792.

Alternatively, the vector can be introduced in vivo by lipofection. The use of cationic lipids can promote encapsulation of negatively charged nucleic acids, and also promote fusion with negatively charged cell membranes. See Feigner P, Ringold G, Nature, 1989; 337:387-388. Particularly useful lipid compounds and compositions for transfer of nucleic acids have been described. See Feigner P, et al., U.S. Pat. No. 5,459,127, Behr J, et al., WO1995018863, and Byk G, WO1996017823.

Thus, in another aspect, the invention relates to a host cell, hereinafter cell of the invention, comprising the polynucleotide of the invention or a vector of the invention. The cells can be obtained by conventional methods known by persons skilled in the art (see e.g. Sambrook et al., cited ad supra).

The term "host cell", as used herein, refers to a cell into which a nucleic acid of the invention, such as a polynucleotide or a vector according to the invention, has been introduced and is capable of expressing the micropeptides of the invention. The terms "host cell" and "recombinant host cell" are used interchangeably herein. It should be understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein. The term includes any cultivatable cell that can be modified by the introduction of heterologous DNA. Preferably, a host cell is one in which the polynucleotide of the invention can be stably expressed, post-translationally modified, localized to the appropriate subcellular compartment, and made to engage the appropriate transcription machinery. The choice of an appropriate host cell will also be influenced by the choice of detection signal. For example, reporter constructs, as described above, can provide a selectable or screenable trait upon activation or inhibition of gene transcription in response to a transcriptional regulatory protein; in order to achieve optimal selection or screening, the host cell phenotype will be considered. A host cell of the present invention includes prokaryotic and eukaryotic cells. Prokaryotes include gram negative or gram positive organisms, for example, *E. coli* or Bacilli. It is to be understood that prokaryotic cells will be used, preferably, for the propagation of the transcription control sequence comprising polynucleotides or the vector of the present invention. Suitable prokaryotic host cells for transformation include, for example, *E. coli, Bacillus subtilis, Salmonella typhimurium*, and various other species within the genera *Pseudomonas, Streptomyces*, and *Staphylococcus*. Eukaryotic cells include, but are not limited to, yeast cells, plant cells, fungal cells, insect cells (e.g., baculovirus), mammalian cells, and the cells of parasitic organisms, e.g., trypanosomes. As used herein, yeast includes not only yeast in a strict taxonomic sense, i.e., unicellular organisms, but also yeast-like multicellular fungi of filamentous fungi. Exemplary species include *Kluyverei lactis, Schizosaccharomyces pombe*, and *Ustilaqo maydis*, with *Saccharomyces cerevisiae* being preferred. Other yeasts which can be used in practicing the present invention are *Neurospora crassa, Aspergillus niger, Aspergillus nidulans, Pichia pastoris, Candida tropicalis*, and *Hansenula polymorpha*. Mammalian host cell culture systems include established cell lines such as COS cells, L cells, 3T3 cells, Chinese hamster ovary (CHO) cells, embryonic stem cells, with BHK, HeK or HeLa cells being preferred. Eukaryotic cells are, preferably, used to for recombinant gene expression by applying the transcription control sequence or the expression vector of the present invention.

Compositions and Pharmaceutical Compositions Comprising the Micropeptides, Polynucleotides, Vectors and Host Cells of the Invention In a further aspect the invention relates to a composition comprising the micropeptide according of the invention, or the polynucleotide, the expression vector or the host cell of the invention.

The term "composition", as used herein, relates to a material composition that comprises the above-mentioned components, as well as any product resulting, directly or indirectly, from the combination of the different components in any quantity thereof. Those skilled in the art will observe that the composition may be formulated as a single formulation or may be presented as separate formulations of each of the components, which may be combined for joint use as a combined preparation. The composition may be a kit-of-parts wherein each of the components is individually formulated and packaged.

In another aspect the invention also relates to a pharmaceutical composition comprising the composition of the invention and a pharmaceutically acceptable carrier.

The term "pharmaceutical composition", as used herein, refers to a composition comprising a therapeutically effective amount of the agents according to the present invention and at least one pharmaceutically acceptable excipient. Pharmaceutical compositions according to the invention can be prepared, for instance, as injectables such as liquid solutions, suspensions, and emulsions.

The term "therapeutically effective amount", as used herein in relation to the micropeptides, the polynucleotides, the vectors or the cells of the invention comprised by the pharmaceutical composition of the invention, relates to the sufficient amount of the micropeptides, the polynucleotides, the vectors or the cells according to the present invention to provide the desired effect, i.e. to achieve an appreciable prevention, cure, delay, reduction of severity or amelioration of one or more symptoms derived from a disease, and will generally be determined by, among other causes, the characteristics of the agent itself and the therapeutic effect to be achieved. It will also depend on the subject to be treated, the severity of the disease suffered by said subject, the chosen dosage form, etc. For this reason, the doses mentioned in this invention must be considered only as guides for the person skilled in the art, who must adjust the doses depending on the aforementioned variables. In an embodiment, the effective amount produces the amelioration of one or more symptoms of the disease that is being treated.

Even though individual needs vary, determination of optimal ranges for effective amounts of the compound of the invention belongs to the common experience of those experts in the art. In general, the dosage needed to provide an effective amount of such compound, which can be adjusted by one expert in the art will vary depending on age, health, fitness, sex, diet, weight, degree of alteration of the receptor, frequency of treatment and the nature and extent of impairment or illness, medical condition of the patient, route of administration, pharmacological considerations such as activity, efficacy, pharmacokinetic and toxicology profile of the particular compound used, if using a system drug delivery, and if the compound is administered as part of a combination of drugs.

Those skilled in the art are familiar with the principles and procedures discussed in widely known and available sources as Remington's Pharmaceutical Science (17th Ed., Mack Publishing Co., Easton, Pa., 1985) and Goodman and Gilman's The terms "pharmaceutically acceptable excipient" or "pharmaceutically acceptable carrier", refer to any compound or combination of compounds that is essentially non-toxic to the subject at the dosage and concentration employed, and is compatible with the other components of a pharmaceutical composition. Thus, an excipient is an inactive substance formulated alongside the active ingredient of a pharmaceutical composition, for the purpose of bulking-up compositions that contain said active ingredients. Bulking up allows convenient and accurate dispensation of a drug substance when producing a dosage form. Excipients also can serve various therapeutic-enhancing purposes, such as facilitating compound (drug) absorption or solubility, or other pharmacokinetic considerations. Excipients can also be useful in the manufacturing process, to aid in the handling of the active substance concerned such as by facilitating powder flowability or non-stick properties, in addition to aiding in vitro stability such as prevention of denaturation over the expected shelf life. The selection of appropriate excipients depends upon the route of administration and the dosage form, as well as the active ingredient and other factors. An excipient can be a non-toxic solid, semisolid or liquid filler, diluent, encapsulating material or formulation auxiliary of any conventional type. Illustrative, non-limitative, examples of excipients or carriers include water, salt (saline) solutions, alcohol, dextrose, vegetable oils, polyethylene glycols, gelatin, lactose, amylose, magnesium stearate, talc, surfactants, silicic acid, viscous paraffin, perfume oil, monoglycerides and diglycerides of fatty acids, fatty acid esters petroetrals, hydroxymethyl cellulose, polyvinylpyrrolidone and the like.

In a particular embodiment, the pharmaceutical composition containing the compound for use in the present invention is a pharmaceutical composition for parenteral administration. Thus, said pharmaceutical composition suitable for parenteral injection, include physiologically acceptable sterile aqueous or non-aqueous solutions, dispersions, suspensions or emulsions, or may comprise sterile powders for reconstitution into sterile injectable solutions or dispersions. Examples of suitable aqueous or non-aqueous excipients or carriers, diluents, solvents or vehicles include water, ethanol, polyols (propylene glycol, polyethylene glycol, glycerol, and the like), suitable mixtures thereof, triglycerides, including vegetable oils such as olive oil, or injectable organic esters such as ethyl oleate. In a particular embodiment, the pharmaceutical composition containing the compound for use in the present invention is a pharmaceutical composition for intravenous, intramuscular or subcutaneous administration. Typically, pharmaceutical compositions for intravenous, intramuscular or subcutaneous administration are solutions in sterile isotonic aqueous buffer. If necessary, the pharmaceutical composition including the compound for use according to the invention also includes a local anesthetic to ameliorate any pain at the site of the injection. Generally, the ingredients are supplied either separately or mixed together in unit dosage form, for example, as a dry lyophilized powder or water free concentrate in a hermetically sealed container such as an ampule or sachette indicating the quantity of active ingredient. Where the pharmaceutical composition is to be administered by infusion, it can be dispensed with an infusion bottle containing sterile pharmaceutical grade water or saline. Where the pharmaceutical composition is administered by injection, an ampule of sterile water for injection or saline can be provided so that the ingredients may be mixed prior to administration.

In another particular embodiment, the pharmaceutical composition containing the compound for use in the present invention is a pharmaceutical composition for oral administration.

Solid dosage forms for oral administration include conventional capsules, sustained release capsules, conventional tablets, sustained-release tablets, chewable tablets, sublingual tablets, effervescent tablets, pills, suspensions, powders, granules and gels. In the solid dosage forms, the active ingredient (i.e., the compound selected from the group consisting of a) a peptide of SEQ ID NO:1, 2 or 3; b) a functionally equivalent variant of the peptide according to a); c) a polynucleotide encoding a) or b); d) a vector comprising a polynucleotide according to c); e) a cell capable of secreting into the medium a peptide according to a) or b); and f) a nanoparticle comprising the peptide according to a) or b)) is admixed with at least one suitable excipient or carrier, such as sodium citrate or dicalcium phosphate or (a) fillers or extenders, such as for example, starches, lactose, sucrose, mannitol, or silicic acid; (b) binders, such as for example, carboxymethylcellulose, alginates, gelatin, polyvinylpyrrolidone, sucrose, or acacia; (c) humectants, such as for example, glycerol; (d) disintegrating agents, such as for example, agar-agar, calcium carbonate, potato or tapioca starch, alginic acid, certain complex silicates, or sodium carbonate; (e) solution retarding agents, such as for example, paraffin; (f) absorption accelerators, such as for example, quaternary ammonium compounds; (g) wetting agents, such as for example, cetyl alcohol or glycerol monostearate; (h) adsorbents, such as for example, kaolin or bentonite; and/or (i) lubricants, as for example, talc, calcium stearate, magnesium stearate, solid polyethylene glycols, sodium lauryl sulfate, or mixtures thereof. In the case of capsules and tablets, the dosage forms may also comprise buffering agents.

Solid formulations of a similar type may also be used as fillers in soft or hard filled gelatin capsules using excipients such as lactose or milk sugar, as well as high molecular weight polyethylene glycols, and the like. Solid dosage forms such as coated tablets, capsules and granules can be prepared with coatings or shells, such as enteric coatings and others known in the art. They may also contain opacifying agents, and can be formulated such that they release the active ingredient or ingredients in a delayed manner. Examples of embedding formulations that can be used are polymeric substances and waxes. The active ingredients can also be in micro-encapsulated form, if appropriate, with one or more of the aforementioned excipients.

Liquid dosage forms for oral administration include pharmaceutically acceptable emulsions, solutions, suspensions, syrups and elixirs containing suitable excipients or carriers used in the art. In addition to the active ingredient (i.e., the compound selected from the group consisting of a) a peptide of SEQ ID NO:1, 2 or 3; b) a functionally equivalent variant of the peptide according to a); c) a polynucleotide encoding a) or b); d) a vector comprising a polynucleotide according to c); e) a cell capable of secreting into the medium a peptide according to a) or b) and f) a nanoparticle comprising the peptide according to a) or b)) the liquid dosage form may contain one or more excipients or carriers commonly used in the art, such as water or other solvents, solubilizing agents and emulsifiers, such as for example, ethyl alcohol, isopropyl alcohol, ethyl carbonate, ethyl acetate, benzyl alcohol, benzyl benzoate, propylene glycol, 1,3-butylene glycol, dimethylformamide, oils, particular cottonseed oil, groundnut oil, corn germ oil, olive oil, castor oil, sesame seed oil, Miglyol®, glycerol, tetrahydrofurfuryl alcohol, polyethylene glycols, fatty acid esters of sorbitan, or mixtures of these substances, and the like. In addition to said inert diluents, the formulation can also include adjuvants, such as wetting agents, emulsifying and suspending agents, sweetening agents, flavoring agents and perfuming agents. Suspensions, in addition to the active ingredient or ingredients, may contain suspending agents, as for example, ethoxylated isostearyl alcohols, polyoxyethylene sorbitol or sorbitan esters, microcrystalline cellulose, aluminum metahydroxide, bentonite, agar-agar, or tragacanth, or mixtures of these substances, and the like.

In another particular embodiment, the pharmaceutical composition containing the compound for use in the present invention is a pharmaceutical composition for topical administration. For topical administration, said pharmaceutical composition can be formulated as a cream, gel, lotion, liquid, pomade, spray solution, dispersion, solid bar, emulsion, microemulsion and the like which may be formulated according to conventional methods that use suitable excipients, such as, for example, emulsifiers, surfactants, thickening agents, coloring agents and combinations of two or more thereof.

The pharmaceutical composition comprising a compound for use according to the invention may be also administered in the form of transdermal patches or iontophoresis devices. Thus, in a specific embodiment, a compound for use according to the invention is administered as a transdermal patch, for example, in the form of sustained-release transdermal patch. Suitable transdermal patches are described in more detail in, for example, U.S. Pat. Nos. 5,262,165, 5,948,433, 6,010,715 and 6,071,531.

Several drug delivery systems are known and can be used to administer the compounds for use according to the invention, including, for example, encapsulation in liposomes, microbubbles, emulsions, microparticles, microcapsules or by means of other nanotechnology systems such as for example polymer therapeutics and the like. The required dosage can be administered as a single unit or in a sustained release form.

Sustainable-release forms and appropriate materials and methods for their preparation are described in the art. In a particular embodiment, the orally administrable form of a pharmaceutical composition comprising a compound for use according to the invention is in a sustained release form that further comprises at least one coating or matrix. The coating or sustained release matrix include, without limitation, natural polymers, semisynthetic or synthetic water-insoluble, modified, waxes, fats, fatty alcohols, fatty acids, natural semisynthetic or synthetic plasticizers, or a combination of two or more of them. Enteric coatings may be applied using conventional processes known to experts in the art.

In a particular embodiment, when the compound for use according to the invention comprises a nucleic acid, the pharmaceutical composition may be formulated as a composition intended for use in gene therapy; by way of illustration, not limitation, that pharmaceutical composition may contain a viral or non-viral vector, which comprises the suitable polynucleotide or gene construction. By way of illustration and not limitation, said vectors, may be viral, for example, based on retrovirus, adenovirus, etc., or nonviral such as ADN-liposome, ADN-polymer, ADN-polymer-liposome complexes, etc. (see "Nonviral Vectors for Gene Therapy", edited by Huang, Hung and Wagner, Academic Press (1999)). Said vectors, which contain the corresponding polynucleotide or gene construction, may be administered directly to a subject by conventional methods. Alternatively, said vectors may be used to transform, or transfect or infect cells, for example, mammal cells, including human, ex vivo, which subsequently will be implanted into a human body or an animal to obtain the desired therapeutic effect. For administration to a human body or an animal, said cells will be formulated in a suitable medium that will have no adverse influence on cell viability.

In a further aspect the invention relates to the micropeptide, the polynucleotide, the expression vector, the host cell, the composition or the pharmaceutical composition of the invention for use in medicine.

Therapeutic Uses in Cancer of the Micropeptides, Polynucleotides and Vectors of the Invention As it is shown in the examples of the present application, the authors of the invention have found out that the micropeptides of the invention are able to act as tumor suppressor agents, being therefore interesting tools for treatment of cancer.

Thus, in another aspect, the invention relates to the micropeptide, the polynucleotide, the expression vector, the host cell, the composition or the pharmaceutical composition of the invention for use in the treatment of cancer.

The term "treatment", as used herein, comprises any type of therapy, which aims at terminating, preventing, ameliorating and/or reducing the susceptibility to a clinical condition as described herein, e.g. cancer. Thus, "treatment," "treating," and the like, as used herein, refer to obtaining a desired pharmacologic and/or physiologic effect, covering any treatment of a pathological condition or disorder in a mammal, including a human. The effect may be prophylactic in terms of completely or partially preventing a disorder or symptom thereof and/or may be therapeutic in terms of a partial or complete cure for a disorder and/or adverse effect attributable to the disorder. That is, "treatment" includes (1) preventing the disorder from occurring or recurring in a subject, (2) inhibiting the disorder, such as arresting its development, (3) stopping or terminating the disorder or at least symptoms associated therewith, so that the host no longer suffers from the disorder or its symptoms, such as causing regression of the disorder or its symptoms, for example, by restoring or repairing a lost, missing or defective function, or stimulating an inefficient process, or (4) relieving, alleviating, or ameliorating the disorder, or symptoms associated therewith, where ameliorating is used in a broad sense to refer to at least a reduction in the magnitude of a parameter. "Treatment" can also mean prolonging survival as compared to expected survival if not receiving treatment. Those in need of treatment include those already with the condition or disorder as well as those prone to have the condition or disorder or those in which the condition or disorder is to be prevented.

The term "cancer" or "tumour" or "tumour disease", as used herein, refers to a broad group of diseases involving unregulated cell growth and which are also referred to as malignant neoplasms. The term is usually applied to a disease characterized by uncontrolled cell division (or by an increase of survival or apoptosis resistance) and by the ability of said cells to invade other neighboring tissues (invasion) and spread to other areas of the body where the cells are not normally located (metastasis) through the lymphatic and blood vessels, circulate through the bloodstream, and then invade normal tissues elsewhere in the body. Depending on whether or not they can spread by invasion and metastasis, tumours are classified as being either benign or malignant: benign tumours are tumours that cannot spread by invasion or metastasis, i.e., they only grow locally; whereas malignant tumours are tumours that are capable of spreading by invasion and metastasis. Biological processes known to be related to cancer include angiogenesis, immune cell infiltration, cell migration and metastasis. Cancers usually share some of the following characteristics: sustaining proliferative signalling, evading growth suppressors, resisting cell death, enabling replicative immortality, inducing angiogenesis, and activating invasion and eventually metastasis. Cancers invade nearby parts of the body and may also spread to more distant parts of the body through the lymphatic system or bloodstream. Cancers are classified by the type of cell that the tumour cells resemble, which is therefore presumed to be the origin of the tumour.

Examples of cancer or tumor include without limitation, breast, heart, lung, small intestine, colon, spleen, kidney, bladder, head, neck, ovarian, prostate, brain, rectum, pancreas, skin, bone, bone marrow, blood, thymus, uterus, testicles, hepatobiliary and liver tumors. In particular, the tumor/cancer can be selected from the group of adenoma, angiosarcoma, astrocytoma, epithelial carcinoma, germinoma, glioblastoma, glioma, hemangioendothelioma, hepatoblastoma, leukaemia, lymphoma, medulloblastoma, melanoma, neuroblastoma, hepatobiliary cancer, osteosarcoma, retinoblastoma, rhabdomyosarcoma, sarcoma, teratoma, acrallentiginous melanoma, actinic keratosis adenocarcinoma, adenoid cystic carcinoma, adenosarcoma, adenosquamous carcinoma, astrocytictumors, bartholin gland carcinoma, basal cell carcinoma, bronchial gland carcinoma, carcinosarcoma, cholangiocarcinoma, cystadenoma, endodermal sinus tumor, endometrial hyperplasia, endometrial stromal sarcoma, endometrioid adenocarcinoma, ependymal sarcoma, Swing's sarcoma, focal nodular hyperplasia, germ cell tumors, glucagonoma, hemangioblastoma, hemangioma, hepatic adenoma, hepatic adenomatosis, hepatocellular carcinoma, insulinoma, intraepithelial neoplasia, interepithelial squamous cell neoplasia, invasive squamous cell carcinoma, large cell carcinoma, leiomyosarcoma, malignant melanoma, malignant mesothelialtumor, medulloepithelioma, mucoepidermoid carcinoma, neuroepithelial adenocarcinoma, nodular melanoma, papillary serous adenocarcinoma, pituitary tumors, plasmacytoma, pseudosarcoma, pulmonary blastoma, renal cell carcinoma, serous carcinoma, small cell carcinoma, soft tissue carcinoma, somatostatin-secreting tumor, squamous carcinoma, squamous cell carcinoma, undifferentiated carcinoma, uveal melanoma, verrucous carcinoma, vipoma, Wilm's tumor.

In a particular embodiment the invention relates to the micropeptide, polynucleotide, expression vector, host cell, composition or pharmaceutical composition of the invention for use in the treatment of cancer, wherein the cancer is a primary tumor or cancer metastasis.

The term "primary tumor", as used herein, refers to a tumor that originated in the location or organ in which it is present and did not metastasize to that location from another location In the context of the present invention, "metastasis" is understood as the propagation of a cancer from the organ where it started to a different organ. It generally occurs through the blood or lymphatic system. When the cancer cells spread and form a new tumor, the latter is called a secondary or metastatic tumor. The cancer cells forming the secondary tumor are like those of the original tumor. If a breast cancer, for example, spreads (metastasizes) to the lung, the secondary tumor is formed of malignant breast cancer cells. The disease in the lung is metastatic breast cancer and not lung cancer.

In another embodiment, the micropeptide, polynucleotide, expression vector, host cell, composition or pharmaceutical composition, wherein the micropeptide is the micropeptide of sequence SEQ ID NO: 1 or SEQ ID NO: 3, are used for the treatment of a cancer characterized in that it comprises an inactivating mutation in the p53 gene.

Thus, in a particular embodiment, the cancer cells carry an inactivating mutation in at least one allele of the p53 gene.

The term "inactivating mutation", as used herein, refers to mutations that partially or completely abrogate the activity of the polypeptide encoded by the mutated polynucleotide. In the particular case of p53, inactivating mutations are those which result in a partial or total deficiency in its ability to initiate a DNA-repair response.

Suitable mutations leading to inactivation of p53 are usually missense mutations such as those known in the art (Michalovitz et al., J. Cell. Biochem., 1991, 45(1):22-9; Vogelstein and Kinzler, Cell, 1992, 70(4):523-6; Donehower and Bradley, Biochim. Biophys. Acta., 1993, 1155(2): 181-205; Levine, Cell, 1997, 88(3):323-31). These mutations affect almost exclusively the core DNA-binding domain of p53 that is responsible for making contacts with p53 DNA-binding sites, although some inactivating mutations have been described in the N-terminal transactivation domain or the C-terminal tetramerization domain (Beroud and Soussi, Nucleic Acids Res., 1998, 26(1):200-4; Cariello et al., Nucleic Acids Res., 1998, 26(1): 198-9; Hainaut et al., P., Nucleic Acids Res. 1998; 26:205-213).

In another particular embodiment, the transgenic non-human animal of the invention is homozygous for a totally defective p53 gene (p53−/−).

In a particular embodiment the micropeptide, the polynucleotide, the expression vector, the host cell, the composition or the pharmaceutical composition of the invention are used in the treatment of a carcinoma cancer.

As used herein, the term "carcinoma" refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas.

In another particular embodiment the micropeptide, the polynucleotide, the expression vector, the host cell, the composition or the pharmaceutical composition of the invention are used in the treatment or carcinoma selected from squamous cell carcinoma, adenocarcinoma, transitional cell carcinoma or basal cell carcinoma.

In a further particular embodiment the micropeptide, the polynucleotide, the expression vector, the host cell, the composition or the pharmaceutical composition of the invention are used in the treatment of carcinoma selected from lung carcinoma, breast carcinoma, bladder carcinoma, prostate carcinoma, colon and rectum carcinoma, skin carcinoma, pancreas carcinoma, ovarian carcinoma, cervix carcinoma, hepatocellular carcinoma or renal cell carcinoma.

Types of carcinoma include without limitation include: Acinic cell carcinoma, Actinic keratosis adenocarcinoma, Adenocarcinoma, Adenoid cystic carcinoma, Adenosquamous carcinoma, Adrenocortical carcinoma, Anaplastic carcinoma, Anaplastic carcinoma of pancreas, Anaplastic carcinoma of thyroid, Bartholin gland carcinoma, Basal cell carcinoma, Basaloid carcinoma, Bronchial gland carcinoma, Carcinoma in situ, CASTLE, Chromophobe cell carcinoma, Clear cell carcinoma, Collecting duct carcinoma, Colloid carcinoma, Ductal carcinoma in situ, Duct cell carcinoma, Embryonal carcinoma, Endometrial carcinoma, Epithelial carcinoma, Epithelial-myoepithelial carcinoma, Fibrolamellar carcinoma, Follicular carcinoma, Giant cell carcinoma, Glassy cell carcinoma, Hepatocellular carcinoma, Hürthle cell carcinoma, Inflammatory carcinoma, In situ carcinoma, Intraductal carcinoma, Intramucosal carcinoma, Juvenile carcinoma, Krebs' carcinoma, Large cell undifferentiated carcinoma of lung, Laryngeal carcinoma, Lobular carcinoma in situ, Medullary carcinoma, Merkel cell carcinoma, Microinvasive carcinoma, Minimal deviation adenocarcinoma of cervix, Mucoepidermoid carcinoma, 'Murky cell' carcinoma, Nasopharyngeal carcinoma, Neuroepithelial adenocarcinoma, Non-small cell carcinoma of lung, Oat cell carcinoma, Ovarian small cell carcinoma-hypercalcemic type, Pleomorphic carcinoma, Pleomorphic lobular carcinoma, Renal cell carcinoma, Sarcomatoid carcinoma, Scirrhous carcinoma, Secretory carcinoma, Serous carcinoma, Soft tissue carcinoma, Spindle cell carcinoma, Squamous carcinoma, Squamous cell carcinoma, Stump carcinoma, Superficial spreading carcinoma, Terminal duct carcinoma, Transglottic carcinoma, Transitional cell carcinoma, Tubular carcinoma and Undifferentiated carcinoma.

In a particular embodiment, the micropeptide of SEQ ID NO: 1, or the polynucleotide, the expression vector, the host cell, the composition or the pharmaceutical composition of the invention encoding or comprising the micropeptide of SEQ ID NO: 1 or comprising the polynucleotide encoding the micropeptide of SEQ ID NO: 1, are used in the treatment of pancreatic, breast, lung, colon or skin cancer. More particular, in the treatment of pancreatic, breast, lung or colon carcinoma, or squamous cell carcinoma.

In another embodiment, the micropeptide of SEQ ID NO: 2 or the polynucleotide, the expression vector, the host cell, the composition or the pharmaceutical composition of the invention encoding or comprising the micropeptide of SEQ ID NO: 2 or comprising the polynucleotide encoding the micropeptide of SEQ ID NO: 2, are used in the treatment of pancreatic and breast cancer. More particular, the cancers are triple negative breast cancer and pancreatic adenocarcinoma.

In another particular embodiment, the micropeptide of SEQ ID NO: 2 or the polynucleotide, the expression vector, the host cell, the composition or the pharmaceutical composition of the invention encoding or comprising the micropeptide of SEQ ID NO: 2 or comprising the polynucleotide encoding the micropeptide of SEQ ID NO: 2 targets both tumour and stromal compartment (cancer associated fibroblasts) in the tumour In another particular embodiment, the micropeptide of SEQ ID NO: 3 or the polynucleotide, the expression vector, the host cell, the composition or the pharmaceutical composition of the invention encoding or comprising the micropeptide of SEQ ID NO: 3 or comprising the polynucleotide encoding the micropeptide of SEQ ID NO: 3, are used in the treatment of colon and lung cancer. More particular, in the treatment of colon and lung carcinoma.

Uses in the Treatment of Fibrosis

As shown in the examples of the application, it is proved that micropeptide of sequence SEQ ID NO: 2 induces downregulation of adhesion factors, such as COLLAGEN I, COLLAGEN IV, FIBRONECTIN and CD44. The upregulation of these factors is related to the development of fibrosis, a pathological feature associated with chronic inflammatory diseases, defined by the overgrowth, hardening, and/or scarring of tissues attributed to excess deposition of extracellular matrix components, such as collagen (Wynn T A et al., 2012, Nat. Med. 18:1028-40). In addition CD44, the receptor of hyaluronic acid and other ligands related with cell adhesion such as collagen and metalloproteinases, has been shown to be required for extracellular matrix adhesion and fibrosis (Li Y, et al, 2011; J Exp Med. 208, 1459-71 and Yang L W et al, 2018, doi: 10.1097/SHK.0000000000001132).

Thus, in another aspect, the invention relates to the micropeptide of SEQ ID NO:2, the polynucleotide encoding said micropeptide, the expression vector, the host cell, the composition or the pharmaceutical composition of the invention for use in the treatment of fibrosis.

As used herein the term "fibrosis" refers to a condition characterized by an excess deposition of fibrous tissue, and it is an underlying manifestation of many disease states. Fibrosis is similar to the process of scarring, in that both involve stimulated cells laying down connective tissue, including collagen and glycosaminoglycans. This can be a reactive, benign, or pathological state. The deposition of connective tissue in the organ and/or tissue can obliterate the architecture and function of the underlying organ or tissue.

Fibrosis can occur in a variety of tissues or organs. These fibrotic conditions include dermal fibrosis (e.g., associated with scleroderma). Dermal fibrosis is fibrosis that manifests itself in the skin (or dermis). Fibrotic conditions also include hypertrophic scars, keloids, burns, Peyronie's disease, and Dupuytren's contractures. Fibrotic conditions also include non-dermal fibrosis. Non-dermal fibrosis is fibrosis that manifests itself in an organ other than the skin (or dermis). As important example of non-dermal fibrosis is lung (or pulmonary) fibrosis. Lung fibrosis can be associated with interstitial lung disease and diffuse proliferative lung disease. An example of lung fibrosis is idiopathic pulmonary fibrosis (JPF), including IPF with severe airway restriction (referred to herein as severe IPF).

Other examples of non-dermal fibrosis include liver/hepatic fibrosis, ocular fibrosis, fibrosis of the gut, kidney/renal fibrosis, pancreatic fibrosis, vascular fibrosis, cardiac fibrosis, myelofibrosis, and the like. Some forms of fibrosis are referred to as interstitial fibrosis, and they include dermal or non-dermal interstitial fibrosis.

Fibrosis may be further categorized by its etiology, to the extent such etiology is known. For example, the fibrosis may be associated with or resulting from an infection (e.g., a viral infection or a parasitic infection), or it may be drug-induced fibrosis (e.g., chemotherapy), or it may be associated with or resulting from substance abuse (e.g., alcohol-induced fibrosis), or it may be associated with or resulting from surgery or other invasive procedure, or it may be associated with or resulting from an underlying condition or event (e.g., a myocardial infarction or diabetes), or it may be associated with or resulting from radiation exposure (e.g., radiation treatment for cancer). Examples include liver/hepatic fibrosis associated with alcohol consumption, viral hepatitis and/or schistosomiasis; post-myocardial infarction cardiac fibrosis; kidney/renal fibrosis associated with diabetes; and post-inflammatory kidney/renal fibrosis. Fibrosis may be transplant-induced, or it may occur independently of transplant (i.e., in a subject that has not undergone a transplant and who is not in need of a transplant)

The term "collagen I", "type I collagen", "alpha 1" or "alpha-1 type I collagen" are used indistinctly in the present application. They refer to a triple helix protein comprising two alpha1 chains and one alpha2 chain (coded by COL1A1 and COL1A2 genes respectively).

The term CD44 as used herein makes reference to a cell-surface glycoprotein involved in cell-cell interactions, cell adhesion and migration. In humans, the CD44 antigen is encoded by the CD44 gene on Chromosome 11. CD44 is also referred to as HCAM (homing cell adhesion molecule), Pgp-1 (phagocytic glycoprotein-1), Hermes antigen, lymphocyte homing receptor, ECM-Ill, and HUTCH-1.

In a particular embodiment the invention relates to the micropeptide, polynucleotide, expression vector, host cell, composition or pharmaceutical composition of the invention for use in the treatment of fibrosis, wherein the fibrosis is associated with loss of function in an organ or tissue, and surgical and/or esthetic complications In another particular embodiment the invention relates to the micropeptide, polynucleotide, expression vector, host cell, composition or pharmaceutical composition of the invention for use in the treatment of fibrosis, wherein the fibrosis is selected from among pulmonary fibrosis, hepatic fibrosis (cirrhosis), renal fibrosis, corneal fibrosis, fibrosis associated with skin and peritoneal surgery, fibrosis associated with burns, osteoarticular fibrosis or keloids.

The invention will be described by way of the following examples which are to be considered as merely illustrative and not limitative of the scope of the invention.

EXAMPLES

Methodology

Chemical Treatments

Doxorubicin, Actinomycin D and Nutlin-3a were purchased from Sigma-Aldrich. Doxorubicin was used at 1 μM, Actinomycin D was used at 5 nM and Nutlin-3a was used at 10 μM in drug treatment experiments.

Cloning Procedures

SEQ ID NO: 1, SEQ ID NO: 2 and SEQ ID NO:3 coding sequence (ORFs) were synthesized (IDT technologies) fused with a flexible linker of amino acidic sequence GGGGSGGGGSGGGGS and a HA-Tag at the C-terminal, and flanked by EcoRI and XhoI enzyme restrictions sites. After digestion by EcoRI and XhoI, the constructs were ligated into pMSCV-Puro retroviral vector. SEQ ID NO: 1 was cloned in the pINDUCER20 vector (Invitrogen) using the Gateway@ Cloning Technology following manufacturer's instructions.

Cell Culture

BxPC-3 and A549 cell lines were cultured in RPMI supplemented with 10% of FBS and penicillin-streptomycin. Patient derived-H10 skin squamous cell carcinoma cell line was cultured in DMEM-F12 supplemented with B27 and penicillin-streptomycin. Cancer associated fibroblasts (CAFs) and PDAC cell lines were derived from $LSL^{-KrasG12D/+;LSL-Trp53R172H/+;Pdx-1-Cre}$ mice and cultured in DMEM-F12 supplemented with 10% FBS and penicillin-streptomycin. All the other cell lines were cultured in DMEM supplemented with 10% of FBS and penicillin streptomycin. Cultures were routinely tested for *mycoplasma* and were always negative.

Retroviral and Lentiviral Transduction $5 \times 10^6$ HEK293T cells were transfected with retroviral or lentiviral vectors and the packaging vectors (pCL-Ampho for retroviral transduction, pLP1 pLP2 and pLP-VSVG for lentiviral transduction) using Fugene HD (Roche). Viral supernatants were collected twice a day on two consecutive days starting 36 h after transfection and were used to infect IMR90 as well as cancer cell lines, previously plated at a density of $8 \times 10^5$ cells per 10 cm plates. Before infection, polybrene was added to the viral supernatants at a concentration of 8 mg/ml.

Analysis of mRNA Levels

Total RNA was extracted with Trizol® and treated with TURBO™ DNase following provider's recommendations. 1 μg of RNA was retrotranscribed using iScript™ cDNA Synthesis Kit (BioRad). Gene expression was analysed by quantitative real time PCR using PowerUp SYBR Green Master Mix (Thermo Fisher Scientific) in the 7900HT Fast Real-Time PCR System (Applied Biosystems). Cycle threshold (Ct) values were normalized to GAPDH.

Western Blot

Cells pellets (4-5*$10^6$ cells) were homogenized in medium-salt lysis buffer (150 mM NaCl, 50 mM Tris pH 8, 1% NP40 and protein inhibitors cocktail). 50 μg of protein was loaded per lane in a 12% acrylamide gel and electrophoresed in Tris-Glycine SDS Running Buffer. The following antibodies were used: Anti-HA-Tag (Abcam, 1:5000), Anti-p53 (Santa Cruz, 1:1000), Anti-p21 (Thermo Fisher, 1:1000), Anti-GAPDH (Thermo Fisher, 1:5000).

Immunofluorescence

Cells were seeded in glass coverslips coated with fibronectin at a cell density of 5×$10^4$ cells/ml. Then, cells were fixed in 4% paraformaldehyde 15 min, washed twice with PBS and then permeabilized with 0.2% (v/v) Triton X-100 for 15 min at room temperature. Blocking step was made in 3% BSA for 1 hour. Cells were incubated in the same blocking buffer containing primary antibody HA Tag Monoclonal Antibody 5B1D10 (1:150, Thermo Scientific) and a custom antibody generated by Abyntek (1:150) at 4° C. overnight. Next day, cells were washed three times with PBS and secondary antibody Alexa-Fluor488 goat anti-mouse and Alexa-Fluor 488 goat anti-rabbit was added at 1:500 dilution and incubated for 1 hour at room temperature in the dark. Finally, cells were washed three times with PBS, mounted in VECTASHIELD® Mounting Medium with DAPI (PALEX MEDICAL, S.A.) and observed at 488-500 nm excitation using a Nikon Eclipse Ti-E inverted microscope system (Nikon, Melville, NY).

Annexin V Assay

After lentiviral infection and puromycin selection for 72 h, infected cells were washed twice with cold PBS and resuspended in Binding Buffer at a cell density of 1×$10^6$ cells/mL. Following manufacturer's instructions (BD Pharmingen™) 100 μL of cells were treated with 5 μL of Annexin V-FITC. After incubation for 15 min in the dark at room temperature, 400 ul of Binding Buffer was added and each sample was supplemented with 10 μL of Propidium Iodide. Flow cytometry analysis was performed on a LSR Fortessa cytometer.

Cell Cycle Analysis and Cell Viability Assays

Micropeptide of SEQ ID NO: 1 expression was induced in BxPC3 cells by treatment with doxycycline (2 μg/ml) for 4 days. Cells were fixed using 100% ethanol at 4° C., stained with Propidium Iodide, and cell cycle was analysed by flow cytometry (LSR-Fortessa cytometer). Cell viability in micropeptide of SEQ ID NO: 1-expressing cells was evaluated using CellTiter-Glo 2.0 (Promega) following manufacturer's instructions.

For drug sensitivity assays, doxycycline induction was coupled with Doxorubicin (1.5 mM) or Actinomycin D (5 nM) (from days 2 to 4), and cell viability was measured by staining with crystal violet.

SA-β-G Staining Assay

For SA-β-gal staining, cells were fixed and stained using a commercial senescence β-galactosidase staining kit (Cell Signalling) following manufacture's protocol.

Cell Proliferation Assay

A549 and H10 cell lines were dissociated by trypsin digestion and seeded into 24-well cell culture plates at density 5×$10^3$ cells/well. Every two days, cells were dissociated from wells and counted using a Neubauer chamber. Cell growth curves were monitored for 14 days.

Wound Healing Assay

MIA PaCa-2 and BxPC-3 cells were trypsinized, counted, and 400,000 cells/well were seeded in 6-well plates. Next day, a pipette tip was used to scratch the surface of cell monolayer, forming a wound. An Olympus CeIIR microscope equipped with a Hamamatsu C9100 camera was used to follow the closure of the wound.

Invasion Assay

BxPC-3, MDA-MB-231, A549 and H10 cell lines were trypsinized, counted, and 20.000 cells/well were seeded in triplicate in a Corning® cell culture insert (Boyden chamber) in which the porous membrane is coated with a layer of Matrigel® to mimic an extra cellular matrix (ECM). Cells were allowed to invade through the coated membrane for 24 hours in the cell incubator at 37° C. After the incubation time, culture inserts were fixed in methanol 5 minutes at RT and stained using Crystal Violet 20 minutes at RT. The excess of Crystal Violet staining was removed washing with PBS and pictures of the chambers were taken using an Olympus CeIIR microscope. Invading cells were counted using ImageJ and fold change was calculated normalizing to the control.

In order to test CAFs pro-invasive activity, 40.000 CAFs/well were seeded in 24-well plates. 48 h later, PDAC cells were trypsinized, counted, and 20.000 cells were seeded in the upper compartment of Matrigel® coated inserts that were placed over CAFs containing wells. CAFs and PDAC cells were this way co-cultured for 24 h, and stained as described above.

Example 1: Micropeptides Identification

The authors of the invention have identified 3 micropeptides corresponding to sequences SEQ ID NO: 1, 2 and 3.

The micropeptide of SEQ ID NO 1 is a highly conserved 87 aa micropeptide whose sequence is:

(FIG. 1A)
MEGLRRGLSRWKRYHIKVHLADEALLLPLTVRPRDTLSDLRAQLVGQGVSS

WKRAFYYNARRLDDHQTVRDARLQDGSVLLLVSDPR.

In silico analysis of the amino acid sequence predicts a 3D structure resembling the protein UBIQUITIN (FIG. 1B). SEQ ID NO 1 micropeptide is coded by the lncRNA TINCR (LINC00036 in humans and Gm20219 in mice).

The micropeptide of SEQ ID NO: 2 is a 64-amino acid micropeptide whose sequence is:

(FIG. 2A)
MVRRKSMKKPRSVGEKKVEAKKQLPEQTVQKPRQECREAGPLFLQSRRETR

DPETRATYLCGEG.

It is encoded by ZEB2 antisense 1 (ZEB2AS1) long non-coding RNA (lncRNA). ZEB2AS1 is a natural antisense transcript corresponding to the 5' untranslated region (UTR) of zinc finger E-box binding homeobox 2 (ZEB2). The ORF encoding the micropeptide spams part of the second and third exons of the lncRNA. I-Tasser, a 3D protein structure predictor, has been used in order to build a model of SEQ ID NO: 2 micropeptide 3D structure (FIG. 2B). Further in-silico analysis has revealed high amino acidic sequence conservation across the species and a potential cytoplasmatic localization of the micropeptide of SEQ ID NO: 2.

The micropeptide of SEQ ID NO: 3 is a 78-amino acid micropeptide encoded by the first exon of LINC0086 lncRNA. Its sequence, highly conserved across evolution is:

(FIG. 3A)
MAASAALSAAAAAAALSGLAVRLSRSAAARGSYGAFCKGLTRTLLTFFDLA

WRLRMNFPYFYIVASVMLNVRLQVRIE.

Figure 3:
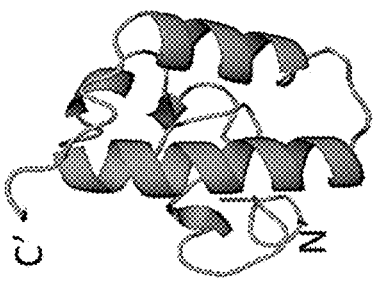
FIG. 3. In silico analysis of the micropeptide of SEQ ID NO: 3. (A) SEQ ID NO: 3 amino acid conservation across mammals. (B) Three-dimensional structure prediction of SEQ ID NO: 3 micropeptide (iTasser software).

In silico analysis of this sequence predicted a tertiary structure (FIG. 3B) with a transmembrane domain at C-terminal of the protein and a signal peptide in the first 25 amino acids.

Figure 4:
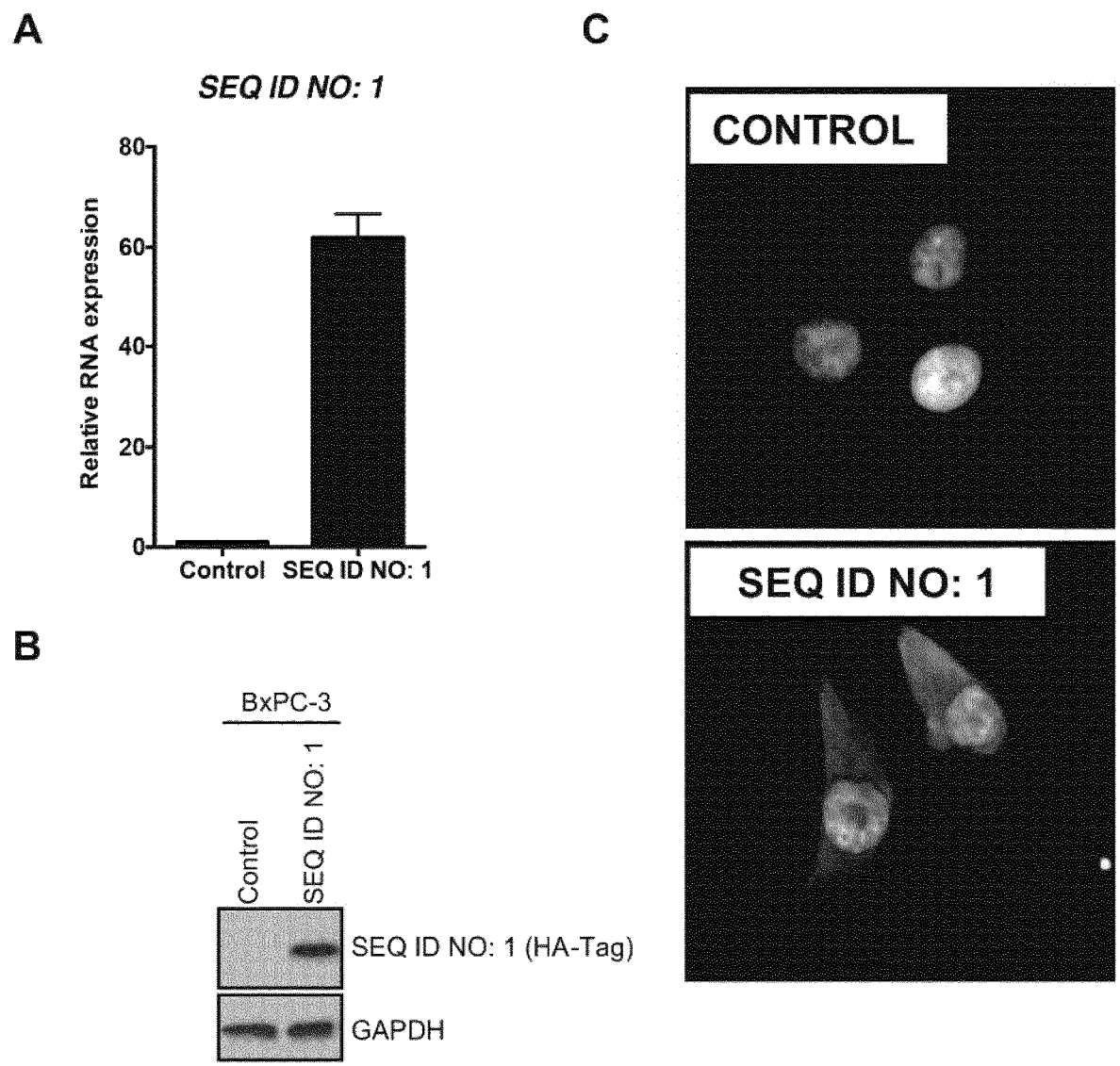
FIG. 4. Detection of the micropeptide of sequence SEQ ID NO: 1 in infected BxPC-3 cells. (A) Analysis of the micropeptide of sequence SEQ ID NO: 1 expression upon doxycycline treatment in BxPC-3, measured by qPCR. mRNA expression is shown relative to the not treated control. (B) Western Blot analysis of the micropeptide of sequence SEQ ID NO: 1 overexpression using an antibody against HA-tag. (C) Immunostaining showing the cytoplasmic localization of the micropeptide SEQ ID NO: 1 in BxPC-3 infected cells using a custom-made anti-SEQ ID NO:1 antibody.
Figure 5:
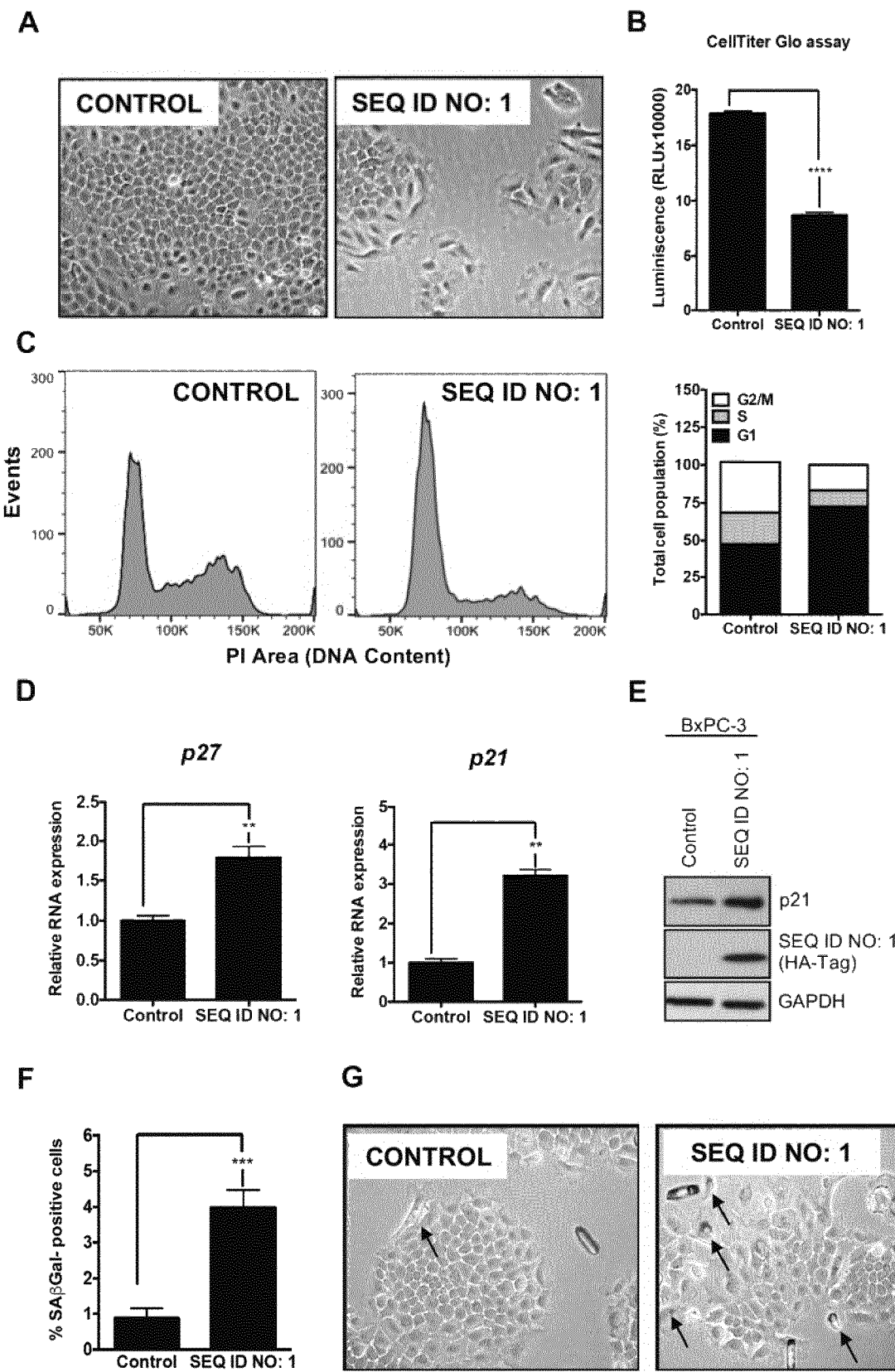
FIG. 5. Micropeptide of sequence SEQ ID NO: 1 overexpression induces cell cycle arrest and cellular senescence. BxPC-3 cells were transduced with an inducible lentivirus coding HA-SEQ ID NO: 1. Micropeptide of sequence SEQ ID NO: 1 expression was induced by doxycycline treatment for 4 days. (A) Phase contrast images of SEQ ID NO:1-expressing cells and control cells. (B) Cell viability analysis by CellTiter-Glo assay. (C) Cell cycle analysis by flow cytometry. Left, histogram plots. Right, quantification of the number of cells in every cell cycle phase (D) Analysis of p27 and p21 expression by qPCR. (E) Western Blot of the indicated cells using anti-HA and anti-p21 antibodies. (F) Quantification of the number of SA-β-Gal positive cells in doxycycline-treated and untreated cells. (G) Representative pictures of the cell quantified in (F). Graphs show the mean±SEM, using at least 3 technical replicates. P<0.01 *P<0,001 **** P<0.0001, two-tailed t-test.

Example 2: Overexpression of the Micropeptide of SEQ ID NO: 1 Induces Cell Cycle Arrest, Cellular Senescence, and Sensitizes Cancer Cells to Stress in Pancreatic and Breast Cancer Cells To determine the biological function of the micropeptide, the ORF encoding for SEQ ID NO: 1 was cloned in frame with the HA epitope tag in both, a retroviral expression vector (pMSCV) and in a doxycycline-inducible lentiviral vector (pINDUCER20). BxPC-3 pancreatic cancer cell line was transduced with the pINDUCER20-SEQ ID NO: 1-HA vector, and infected cells were selected with Neomycin. Upon treatment with doxycycline, SEQ ID NO: 1 expression was detected by qPCR (FIG. 4A) and by Western Blot (FIG. 4B), demonstrating that the micropeptide is expressed and stable in cells. Immunostaining using a custom-made antibody against SEQ ID NO: 1 revealed a cytoplasmic cellular localization (FIG. 4C). The micropeptide of SEQ ID NO: 1 expression significantly reduces cell proliferation (FIGS. 5A and 5B) and induces cell cycle arrest in G1 phase (FIG. 5C), together with the upregulation of the CDK inhibitors p27 and p21 (FIGS. 5D and 5E), and an increase in the number of senescent cells (SA-β-Gal-positive cells) (FIGS. 5F and 5G). Remarkably, the micropeptide of SEQ ID NO: 1 expression induces an extensive cell death when coupled with cellular stress, such as the one produced by Puromycin during selection of infected cells (when using pMSCV non-inducible vector), as shown in several pancreatic and breast cancer cell lines (FIG. 6C). Annexin V/PI assay revealed a substantial increase in the percentage of early apoptotic (22.4%) and late apoptotic cells (58.6%) in SEQ ID NO: 1-Puromycin conditions compared with the controls (FIG. 6D). In agreement with these results, the micropeptide of SEQ ID NO: 1 expression sensitizes to cell death induced by drugs as Doxorubicin and Actinomycin D (FIG. 6E).

Figure 7:
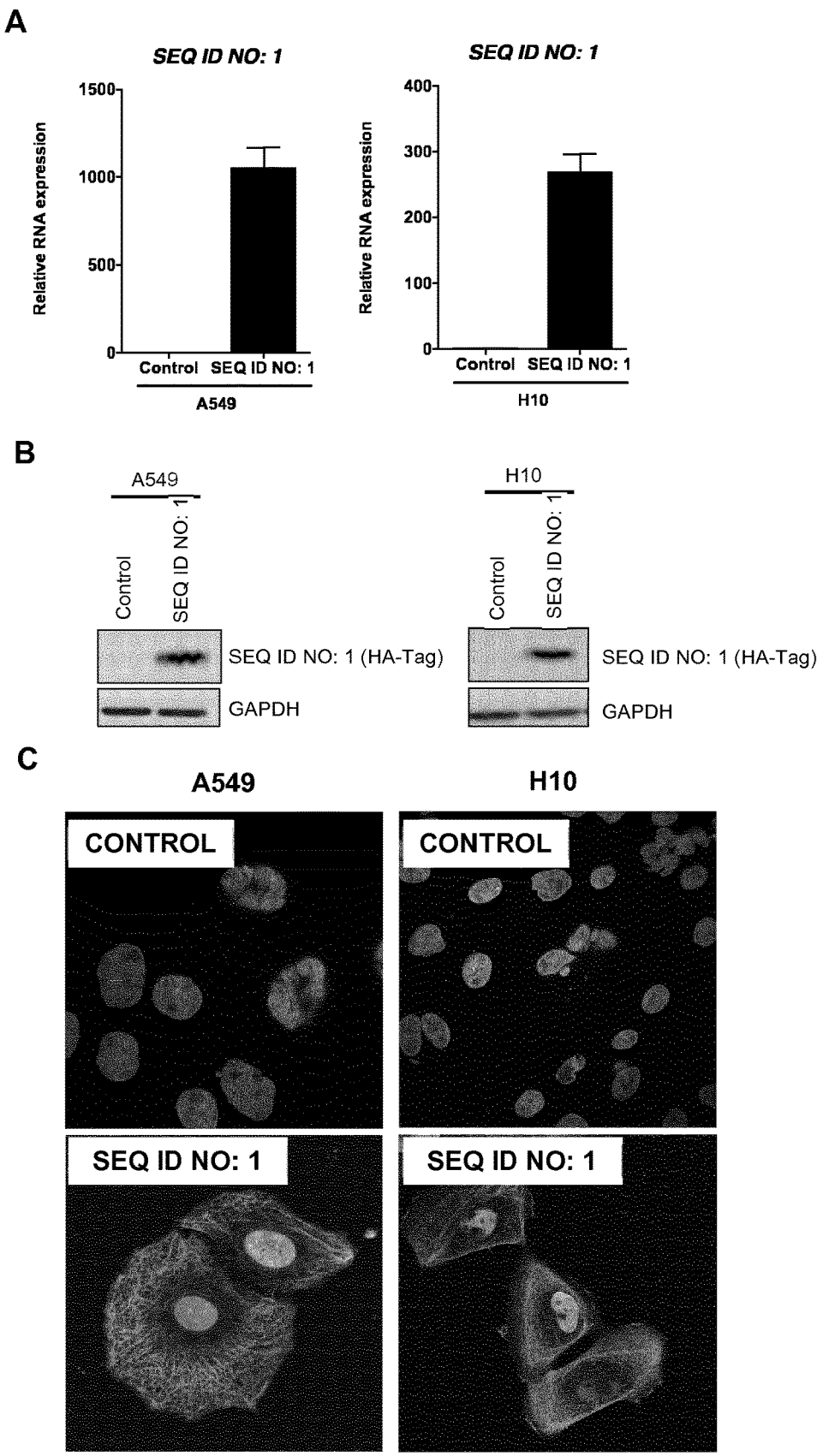
FIG. 7. Detection of the overexpressed SEQ ID NO: 1 micropeptide in A549 and H10 cells. (A) Analysis of SEQ ID NO: 1 expression upon doxycycline treatment in A549 and H10, measured by qPCR. mRNA expression is shown relative to the control. (B) Western Blot analysis of SEQ ID NO: 1 overexpression using an antibody against HA-tag. (C) Immunostaining showing the cytoplasmic localization of SEQ ID NO: 1 in A549 and H10 infected cells using a custom-made anti-SEQ ID NO: 1 antibody.

Example 3: Overexpression of the Micropeptide of SEQ ID NO: 1 Decreases Cell Proliferation and Induces Cell Cycle Arrest in Lung Adenocarcinoma Cells and Squamous Cell Carcinoma Cells Lung cancer cell line A549 and squamous cell carcinoma cell line H10 expressing inducible SEQ ID NO: 1-HA vector were established as described previously. SEQ ID NO: 1 expression was detected by qPCR (FIG. 7A) and by Western Blot (FIG. 7B). Immunostaining using a custom-made antibody against SEQ ID NO: 1 reveals a predominant cytoplasmic localization with a filamentous pattern. This data demonstrates that the micropeptide can also be expressed and detectable in these cell lines.

To evaluate the effects of SEQ ID NO: 1 on proliferation, A549 and H10 cells transduced with SEQ ID NO: 1-HA vector or control vector were monitored for 14 days. Growth curves show that cells overexpressing micropeptide SEQ ID NO: 1 have a consistently lower growth rate compared to the control (FIG. 8A). This effect in proliferation is also accompanied by an increase in cells arrested in G1 phase (FIG. 8B). Collectively with the data shown before in the pancreatic cell line BxPC-3, there is a strong evidence of the role of the micropeptide of SEQ ID NO: 1 in decreasing cell proliferation in several cancer types (pancreas, lung and squamous cell carcinoma).

Example 4: The Micropeptide of SEQ ID NO:1 Impairs Cell Invasion Capability and Downregulates the Mesenchymal Program Given the effect of the overexpression of the SEQ ID NO:1, further experiments were performed to study its effect in cell invasion, another key oncogenic trait. Boyden chamber assay was used to determine invasiveness of A549 and H10 cancer cells after 4 days of doxycycline induction of SEQ ID NO:1, showing that the expression of the micropeptide induces a significant decrease in invasion (FIGS. 9A and B). In line with this observation, overexpression of the micropeptide of SEQ ID NO: 1 represses the expression of the EMT regulators VIMENTIN, SLUG, SNAIL, N-CADHERIN, TWIST1, TWIST2, ZEB1 and ZEB2 in H10 SCC cell line (FIG. 9C). This downregulation of the mesenchymal program further validates the role of the micropeptide of SEQ ID NO: 1 as a tumor suppressor.

Figure 10:
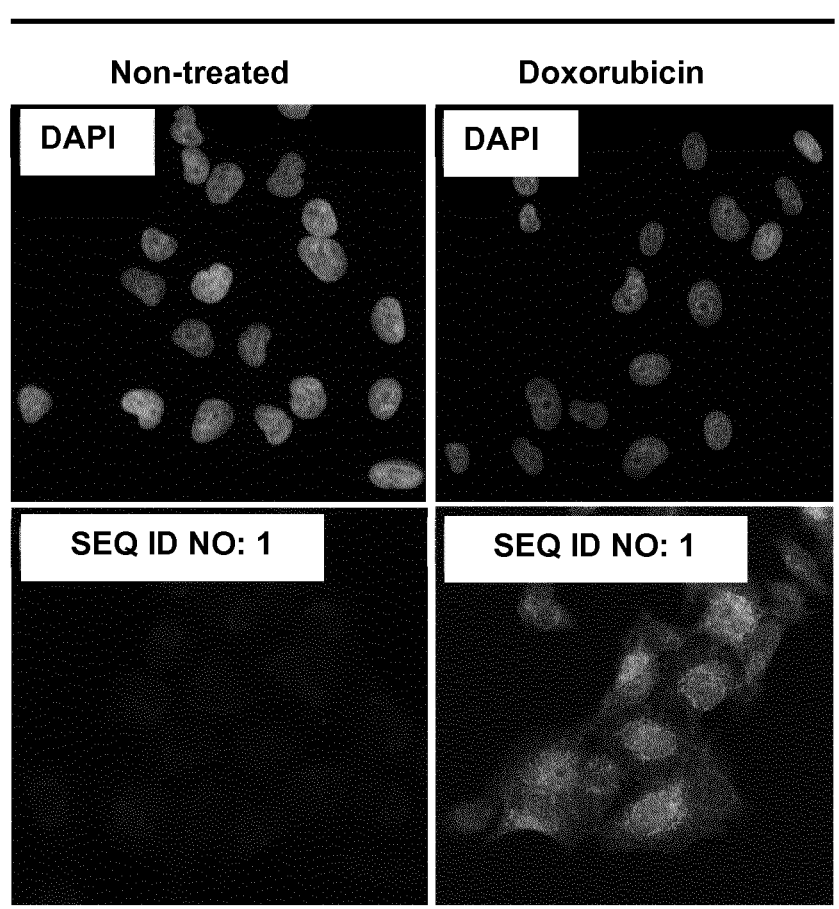
FIG. 10. SEQ ID NO: 1 is induced by genotoxic stress in a p53-dependent manner. HCT116, HCT116 p53KO, A549 and BxPC3 were treated with Doxorubicin (1 µM) or Actinomycin D (1 nM) and Nutlin-3a (10 µM). SEQ ID NO: 1 transcriptional levels were measured by qPCR in A549 and HCT116 (A) and in HCT116 p53KO and BxPC-3 (B). mRNA expression is shown relative to the not treated control. SEQ ID NO: 1 protein was measured by Western Blot analysis using a custom-made anti-SEQ ID NO: 1 antibody in A549 and HCT116 (A) and in HCT116 p53KO and BxPC-3 (B). (C) Immunostaining showing the upregulation of SEQ ID NO: 1 in A549 cells using a custom-made anti-SEQ ID NO: 1 antibody upon Doxorubicin treatment.

Example 5: Transcription and Translation of Micropeptide of SEQ ID NO:1 is Increased Upon Genotoxic Stress in a p53-Dependent Manner The tumor suppressor gene p53 is well known to have a role in controlling apoptosis, cell cycle arrest, senescence and cell migration and invasion upon activation when DNA is damaged. Due to the potential tumor suppressor function of micropeptide of SEQ ID NO:1 further studies were performed to study how both proteins could be connected. Different cell lines (A549, BxPC-3 and HCT116) were treated with different DNA-damaging agents commonly used in cancer treatment (Doxorubicin and Actinomycin D) and one p53 stabilizer (Nutlin-3a) to promote p53 activation. Then, the expression of SEQ ID NO:1 were measured, and it was observed that SEQ ID NO:1 is induced (mRNA and protein levels) upon genotoxic stress (FIGS. 10A, B and C). Importantly, only the cells with wild-type p53 (HCT116 and A549) show a transcriptional and translational upregulation of SEQ ID NO:1 (FIG. 10A). On the other hand, cells with a p53 status altered, protein knock-out (HCT116 p53KO) or pathogenic mutant p53 (BxPC-3), do not shown the same response (FIG. 10B).

As a tumor suppressor, p53 is responsible for protecting cells from oncogenic alterations. Activation of p53 can promote apoptosis of tumor cells and is considered a key mechanism of action of some antitumor drugs, as Doxorubicin. Inactivating mutations of p53 are frequently observed in various human cancers and are known to confer tumor resistance. These results suggest that SEQ ID NO:1 is regulated in a p53-dependent manner and thereby, possibly downregulated in all cancers with mutational inactivation of p53. Therefore, its tumor suppressor activity can be related with p53 function, supporting the use of the micropeptide as a therapeutic agent in cancer.

Example 6: The Micropeptide of SEQ ID NO: 1 Encodes a Ubiquitin-Like Protein that Changes Cell Ubiquitylation Pattern Structural modelling by in silico tools predicted the micropeptide of sequence SEQ ID NO: 1 as an ubiquitin-like protein (FIG. 1B). Ubiquitin is a highly conserved small protein widely present in all eukaryotic cells, which can exist either not anchorage or covalently attached to another protein. When conjugated to its target proteins it orchestrates important biological processes, as protein degradation via the proteasome, DNA repair, cell-cycle regulation, signalling cascades and DNA-damage responses. Recently, it has been demonstrated that ubiquitin-like proteins (ULPs), which have structural similarity to ubiquitin, are also present in cells and have protein-conjugation capability that can resemble ubiquitylation (Hochstrasser, 2009). Given the structural features of the micropeptide of sequence SEQ ID NO: 1, ubiquitin-related functions of this micropeptide were tested. Immunoprecipitation experiments have shown that the micropeptide of sequence SEQ ID NO: 1 binds to ubiquitylated proteins (FIG. 11A). Moreover, micropeptide of sequence SEQ ID NO: 1 overexpression alters protein ubiquitylation pattern in BxPC-3 infected cells (FIG. 11B).

Altogether, our results suggest that micropeptide of SEQ ID NO:1 induces cell cycle arrest, cellular senescence, sensitizes cancer cells to stress and reduces cell invasion and mesenchymal traits, possibly by changing cell ubiquitylation pattern. This opens the possibility of using micropeptide of SEQ ID NO:1 as a therapy to reduce tumour growth and invasiveness and make them more sensitive to chemo/radiotherapy in combined therapies.

Figure 13:
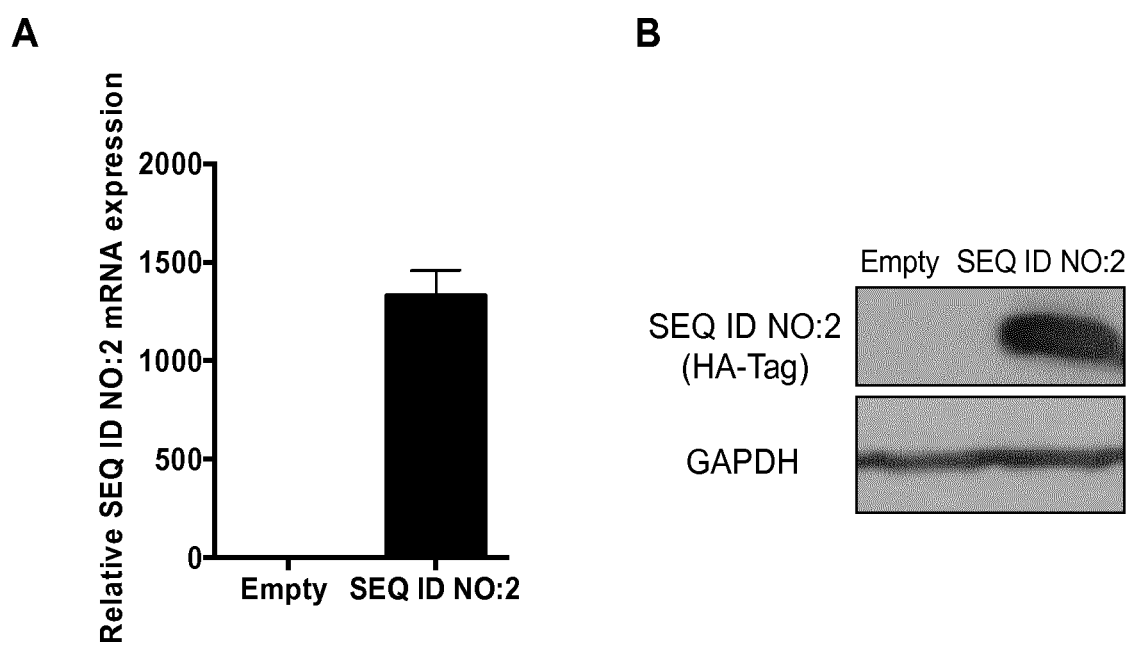
FIG. 13. Detection of SEQ ID NO: 2 micropeptide in transduced mCAFs cells. (A) Micropeptide of SEQ ID NO:2 mRNA expression in mCAFs cells infected with the micropeptide of SEQ ID NO: 2 or empty vector, analyzed by qPCR. Values are relative to cells expressing the empty vector as a control. Bars correspond to average±SD. (B) Western Blot against HA-tag mCAFs cells infected with the micropeptide of SEQ ID NO: 2 or empty vector.

Example 7: Overexpression of the Micropeptide of SEQ ID NO: 2 Downregulates EMT Factors and Reduces Migration and Invasion in Pancreatic Adenocarcinoma The ORF encoding the micropeptide of SEQ ID NO: 2 was cloned into pMSCV retroviral vector fused to a HA-tag. The construct thus obtained was used to retrovirally transduce human primary fibroblasts (IMR90), pancreatic cancer cell lines (MIA PaCa-2 and BxPC-3) and murine pancreatic cancer associated fibroblasts (mCAFs). The overexpression of the micropeptide of SEQ ID NO: 2 was confirmed in all the cell lines by quantitative PCR and Western Blot analysis using a HA-tag antibody (FIGS. 12 and 13). Immunostaining using a custom polyclonal antibody specific for the micropeptide of SEQ ID NO: 2 showed that the micropeptide of SEQ ID NO: 2 was expressed and located in the cytoplasm (FIG. 14).

Figure 15:
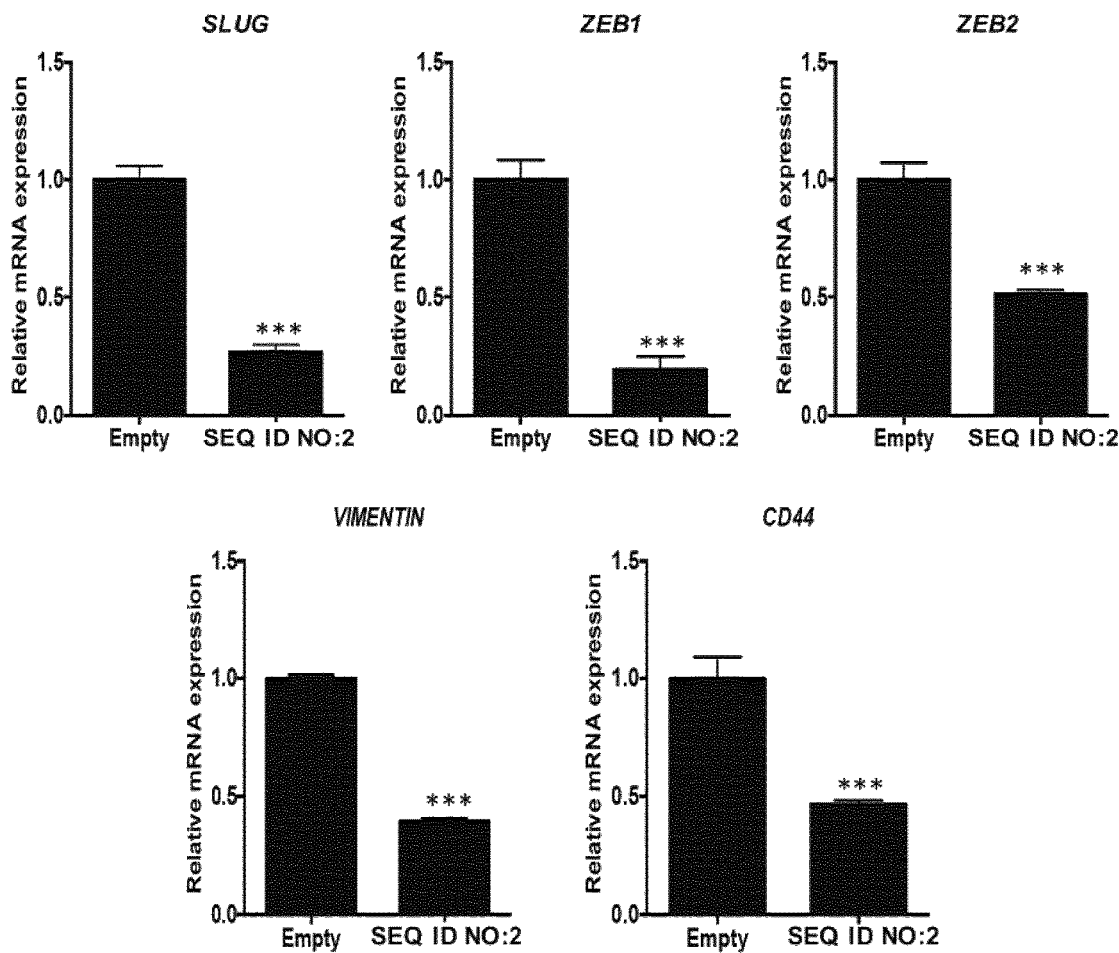
FIG. 15. Expression of the micropeptide of SEQ ID NO: 2 induces loss of mesenchymal identity in IMR90 (A), MIA PaCa-2 (B) and BxPC-3 (C) cell lines. mRNA levels of the indicated genes measured by qPCR. Values are relative to cells expressing the empty vector as a control. *P<0.05, P<0.01, *P<0.001 using Student's t-test for statistics. Error bars represent standard error of n=3 technical replicates.
Figure 15:
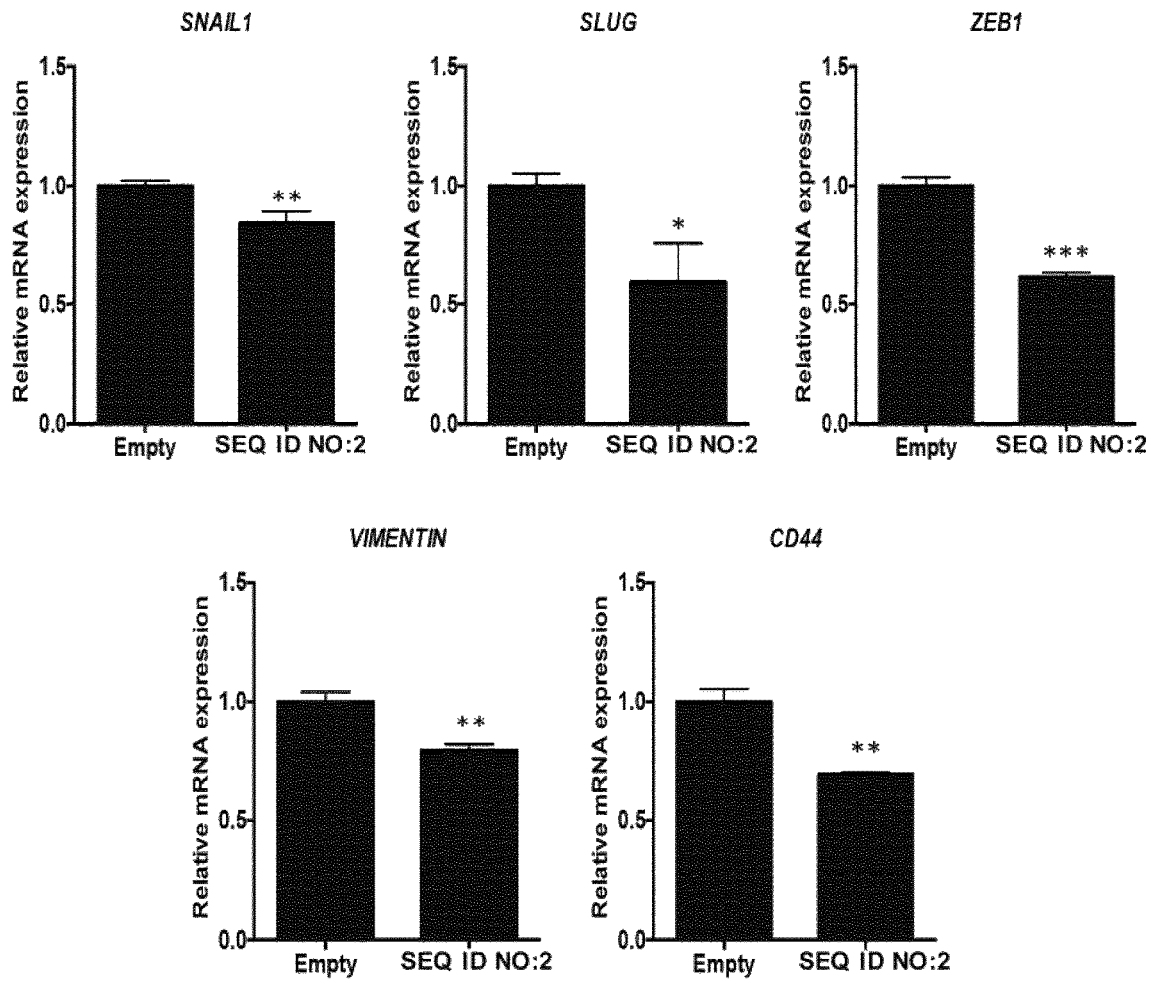
Figure 15:
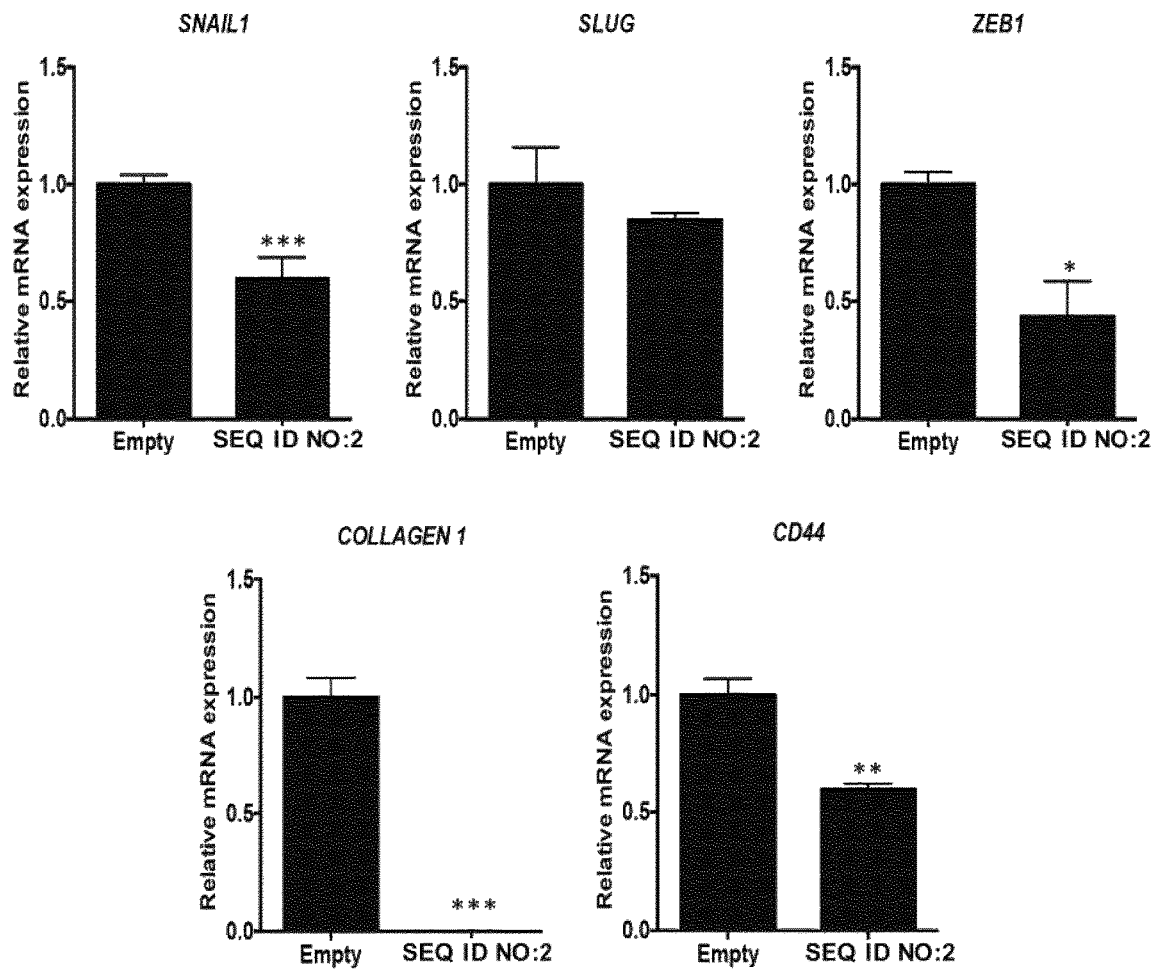
Figure 16:
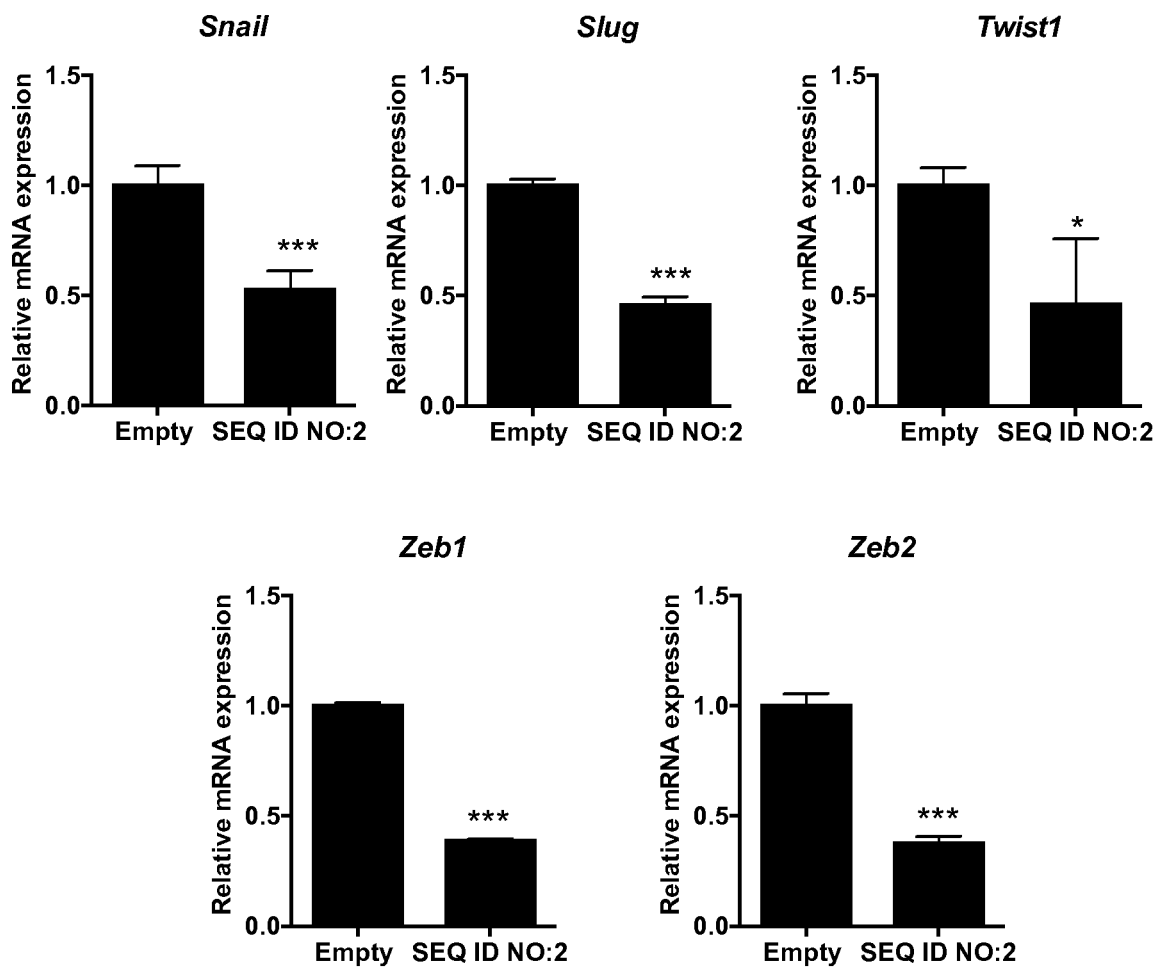
FIG. 16. Overexpression of the micropeptide of SEQ ID NO: 2 induces loss of mesenchymal identity. mRNA levels of the indicated genes were measured by qPCR in mCAFs (A-B) cells. Values are relative to cells expressing the empty vector as a control. *P<0.05; P<0.01; *P<0.001 using Student's t-test for statistics. Error bars represent standard error of n=3 technical replicates.
Figure 16:
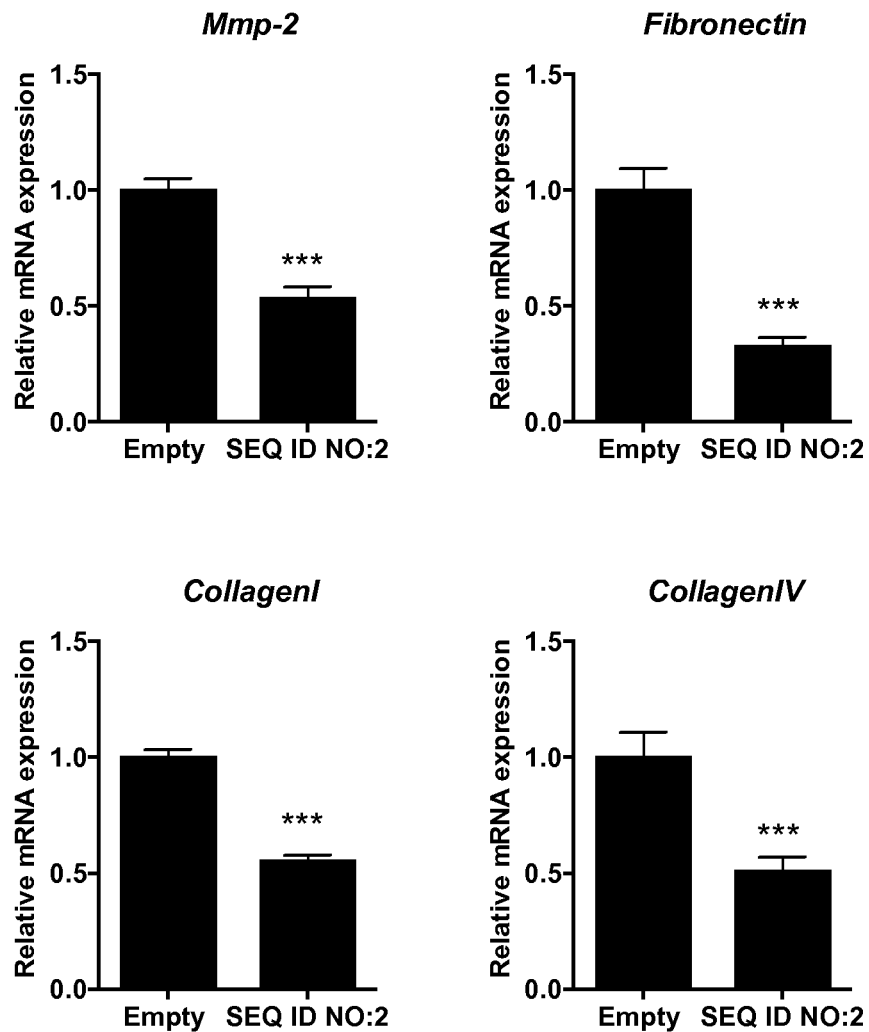

Then, the inventors tested the effect of the overexpression of the SEQ ID NO: 2 micropeptide in epithelial-to-mesenchymal transition (EMT) related genes expression. Of note, the micropeptide of SEQ ID NO: 2 induces the loss of mesenchymal identity in primary fibroblasts and pancreatic cancer cell lines as well as in pancreatic cancer associated fibroblasts, as shown by the downregulation of the EMT regulators SNAIL, SLUG, ZEB1, ZEB2, TWIST1 and VIMENTIN (if expressed), and adhesion factors such as COLLAGEN I, COLLAGEN IV, CD44 and FIBRONECTIN (FIGS. 15 and 16). Remarkably, the decreased expression of adhesion molecules in mCAFs is also accompanied by a downregulation of METALLOPROTEINASE-2 (FIG. 16). Adhesion molecules, as well as metalloproteinases, are factors secreted by cancer associated fibroblasts that are required in order to create a pro-metastatic environment (Hwang R F et al., Cancer Res. 2008; 68:918-26 and Vonlaufen A et al., Cancer Res. 2008; 68:2085-93).

Figure 17:
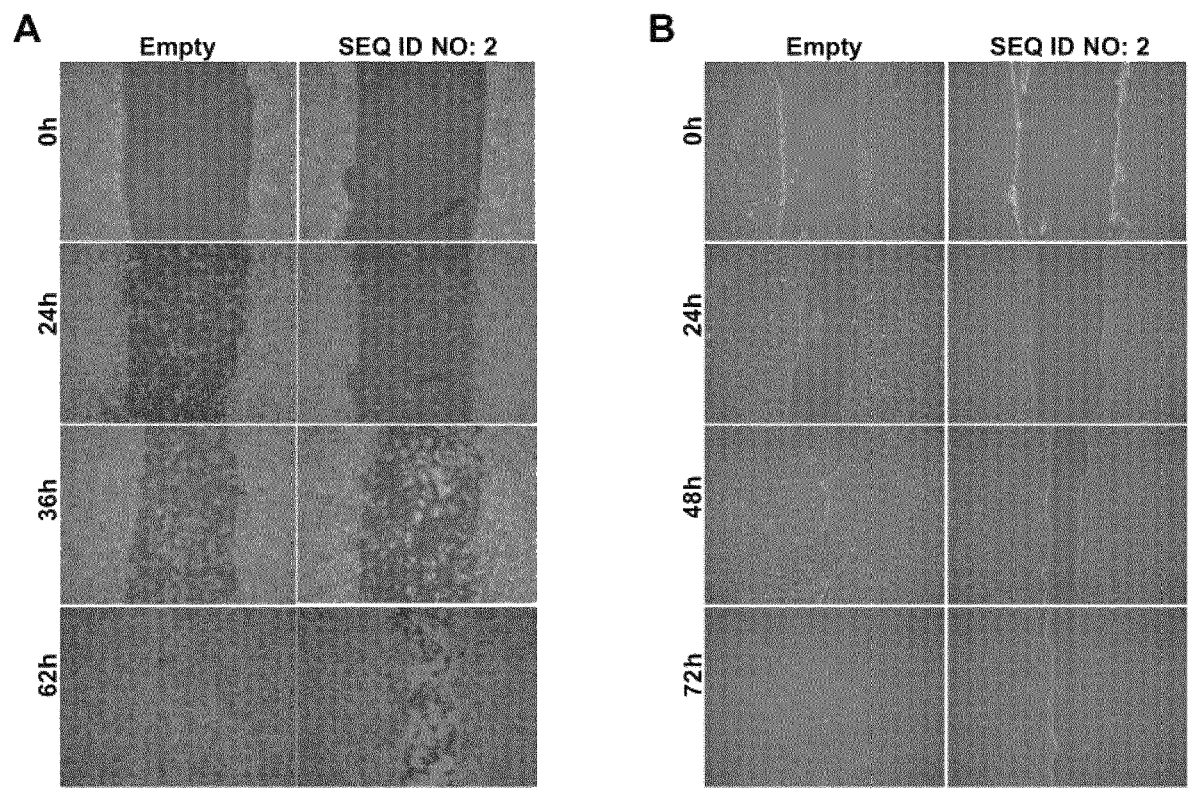
FIG. 17. The micropeptide of SEQ ID NO: 2 impairs migration capability of pancreatic cancer cell lines. Wound healing assay was performed in MIA PaCa-2 (A) and BxPC-3 (B) cells infected with MIDORI or empty vector. Phase contrast images show the wound at the indicated time points after the scratch was performed.

Consistent with these results, overexpression of the micropeptide of SEQ ID NO: 2 leads to a decreased migration capability in wound healing assays in MIA PaCa-2 and BxPC-3 cell lines (FIGS. 17A and B) and a decreased invasion of BxPC-3 cell line (FIGS. 18A and B).

Moreover, the downregulation of extracellular matrix factors such as COLLAGEN I, COLLAGEN IV and FIBRONECTIN togetherwith the secreted METALLOPROTEINASE-2 in cancer associated fibroblasts addresses the possibility of using the micropeptide of SEQ ID NO: 2 as an antifibrotic agent to target the pro-tumoral activity of this particular cell group within tumours, and in general in pathological fibrotic conditions. In order to test CAFs pro-invasive activity, CAFs were co-cultured with PDAC cells that were seeded in the upper compartment of Matrigel® coated inserts and allowed to invade through the matrigel layer. FIGS. 19A and B show that the micropeptide of SEQ ID NO:2 expression in CAFs reduces pancreatic cancer cell invasion in a non-cell autonomous manner, supporting the use of the micropeptide of SEQ ID NO:2 as a therapeutic agent that could potentially target both cancer cells and the stromal counterpart.

Example 8: Overexpression of the Micropeptide of SEQ ID NO: 2 Downregulates EMT Factors and Impairs Invasion in Triple Negative Breast Cancer The construct containing the micropeptide of SEQ ID NO: 2 (explained in Example 7) was also used to retrovirally transduce a human triple negative breast cancer cell line (MDA-MB-231).

Figure 20:
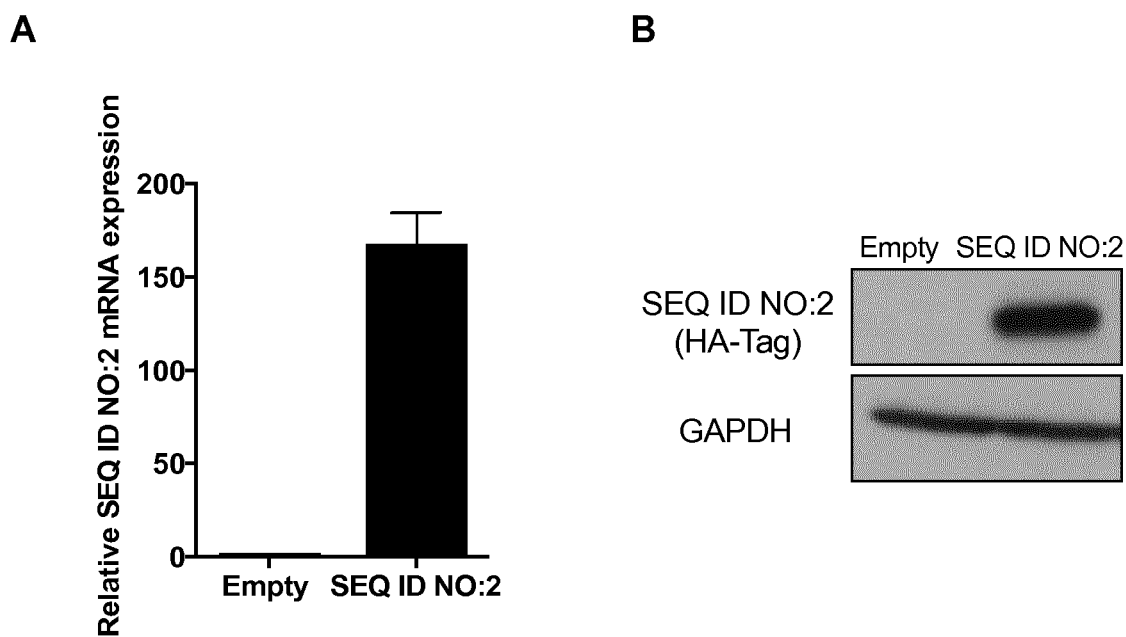
FIG. 20. Detection of SEQ ID NO: 2 micropeptide in transduced MDA-MB-231 cells. (A) Micropeptide of SEQ ID NO:2 mRNA expression in MDA-MB-231 cell line infected with the micropeptide of SEQ ID NO: 2 or empty vector, analyzed by qPCR. Values are relative to cells expressing the empty vector as a control. Bars correspond to average±SD. (B) Western Blot against HA-tag in MDA-MB-231 cells infected with the micropeptide of SEQ ID NO: 2 or empty vector.

The overexpression of the micropeptide of SEQ ID NO: 2 was confirmed in MDA-MB-231 cells by quantitative PCR and Western Blot analysis using a HA-tag antibody (FIGS. 20A and B).

Figure 21:
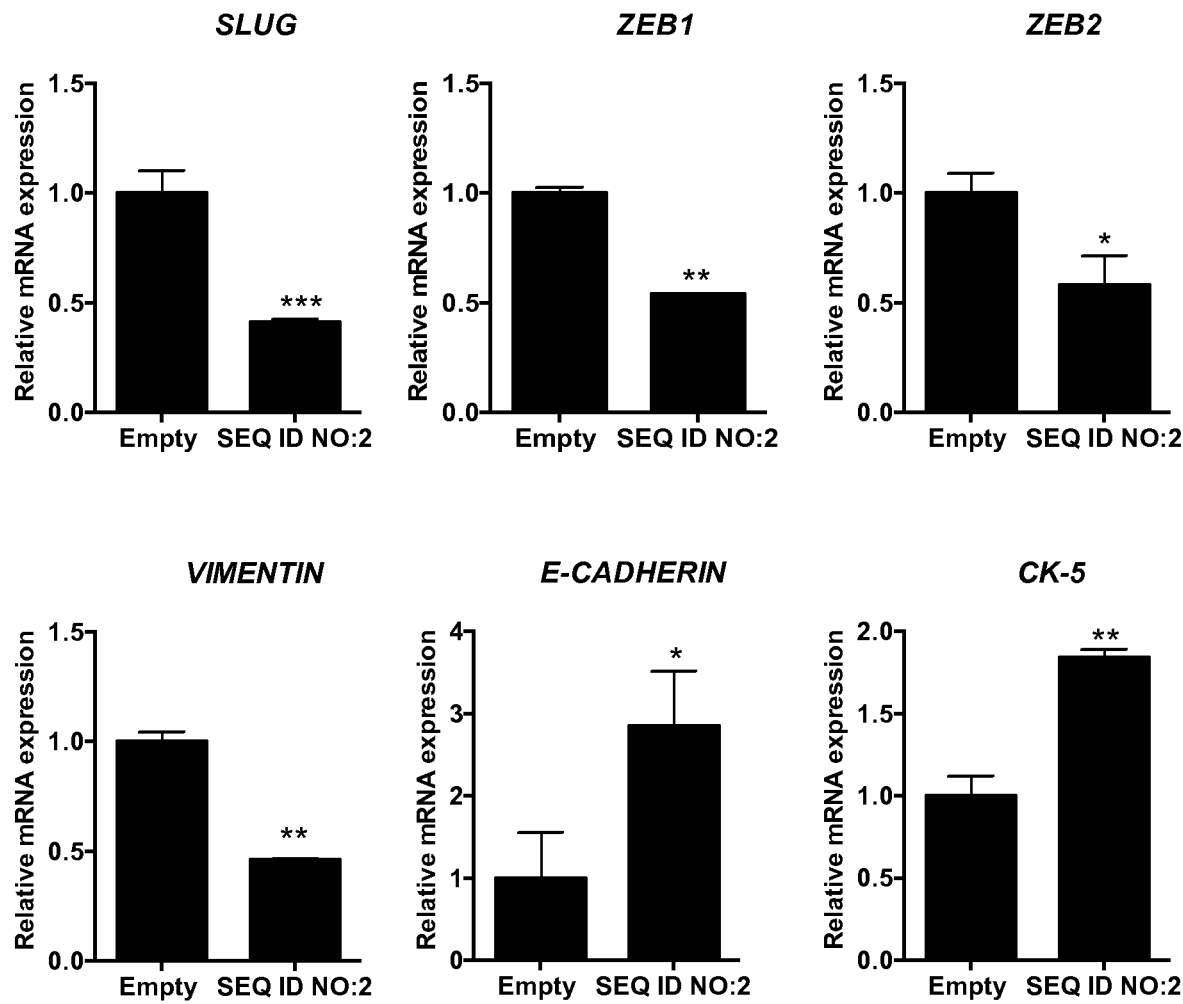
FIG. 21. Overexpression of the micropeptide of SEQ ID NO: 2 induces loss of mesenchymal identity. mRNA levels of the indicated genes were measured by qPCR in MDA-MB-231 cell line. Values are relative to cells expressing the empty vector as a control. *P<0.05; P<0.01; *P<0.001 using Student's t-test for statistics. Error bars represent standard error of n=3 technical replicates.

The overexpression of the micropeptide of SEQ ID NO: 2 induces the loss of mesenchymal identity in human triple negative breast cancer cell line. Of note, the downregulation of the EMT regulators SLUG, ZEB1, ZEB2 and VIMENTIN in MDA-MB-231 is followed by the upregulation of epithelial markers such as E-CADHERIN and CYTOKERATIN-5 (FIG. 21), further validating the role of the micropeptide of SEQ ID NO: 2 in promoting an epithelial phenotype.

Consistent with these results, the overexpression of the micropeptide of SEQ ID NO: 2 leads to a decreased invasion capability in invasion assays of MDA-MB-231 breast cancer cell line (FIG. 22), altogether indicating that the micropeptide of SEQ ID NO:2 could act as an EMT negative regulator, contributing to decrease cancer malignant features such as invasion, metastasis and resistance to chemotherapeutic drugs.

Example 9: Overexpression of the Micropeptide of SEQ ID NO: 3 Induces Cell Death The ORF encoding the micropeptide of SEQ ID NO: 3 was cloned in frame with the HA epitope tag in the pMSCV retroviral vector. Western blot and qPCR analysis demonstrated that the micropeptide of SEQ ID NO: 3 was successfully expressed after retroviral transduction, and that the protein product was stable (FIG. 23A y 23B).

Importantly, overexpression of the micropeptide of SEQ ID NO: 3 induces massive cell death in cancer cell lines (A549, human lung cancer and HCT116, human colorectal cancer) (FIG. 23C).

Example 10: Overexpression of the Micropeptide of SEQ ID NO: 3 Induces p21 and a Pro-Apoptotic Program The impact of the overexpression of the micropeptide of SEQ ID NO: 3 on the expression of the CDK inhibitor (and tumor suppressor) p21 was tested. Interestingly, overexpression of the micropeptide of SEQ ID NO: 3 resulted in a substantial p21 upregulation in A459 and HCT116 cells (FIG. 24A). This correlated with increased p21 protein levels upon SEQ ID NO: 3 micropeptide overexpression, as shown in FIG. 24B.

Figure 24:
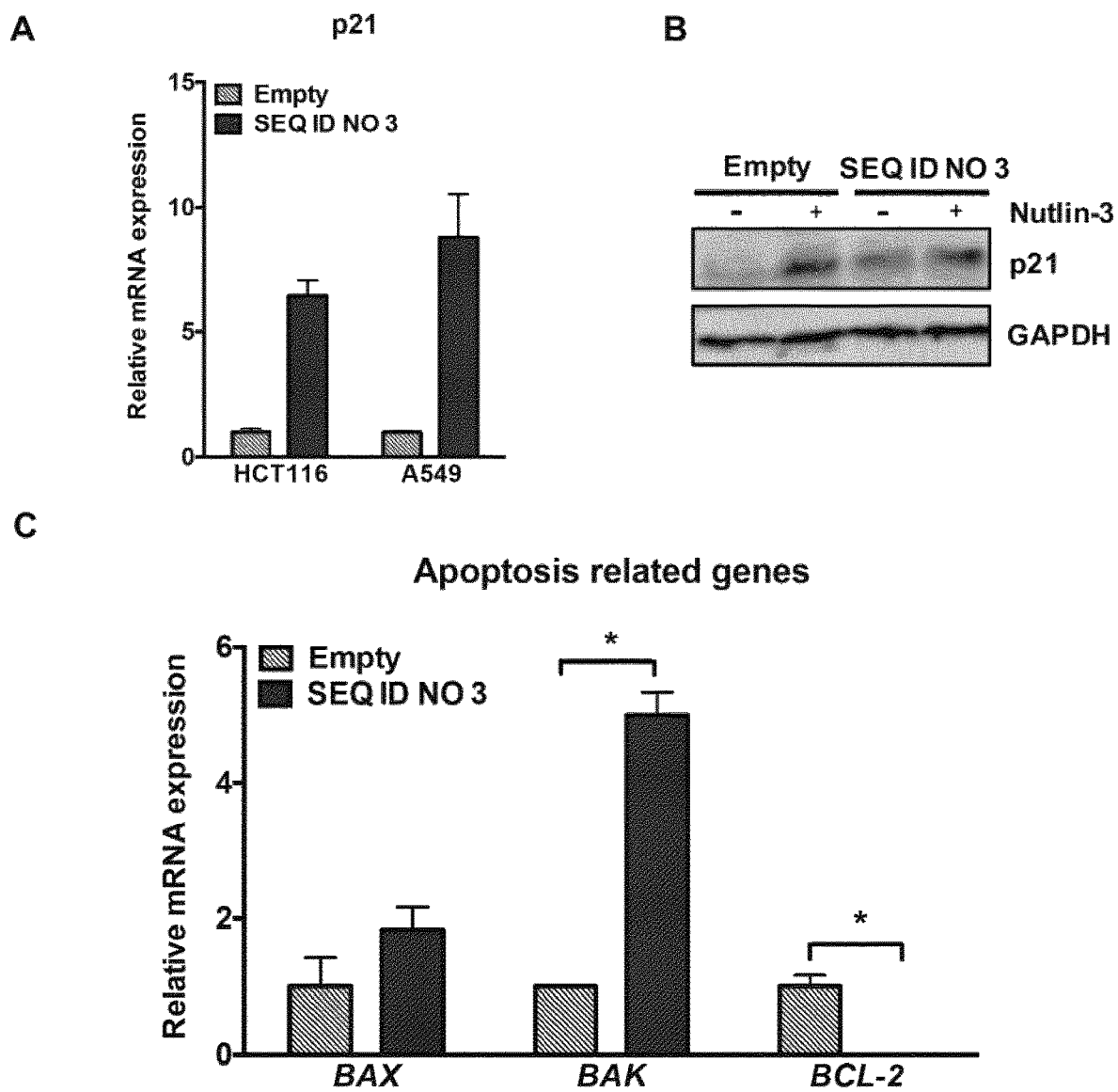
FIG. 24. Overexpression of the micropeptide of SEQ ID NO: 3 induces p21 upregulation and a pro-apoptotic program (A) qPCR analysis of p21 expression in HCT116 and A549 cancer cell lines upon SEQ ID NO: 3 overexpression. (B) Western blot analysis of p21 protein in A549 SEQ ID NO: 3-overexpressing cells. Cells treated with Nutlin-3 (10 μM) were used as positive control for p21 upregulation. (C) qPCR analysis of the indicated apoptosis-related genes in SEQ ID NO: 3-overexpressing HCT116 cells.

Given the induction of cell death by the micropeptide of SEQ ID NO: 3 and the role of p21 in apoptosis, the authors of the invention tested the expression of apoptosis-related genes. Overexpression of the micropeptide of SEQ ID NO: 3 induces the upregulation of the pro-apoptotic genes BAX and BAK and the downregulation of the antiapoptotic gene BCL-2 in HCT116 colorectal cancer cell line (FIG. 24 C).

Example 11: SEQ ID NO:3 is Upregulated Upon Genotoxic Stress in a p53-Dependent Manner As previously indicated, p53 is an important tumour suppressor. Given the potential role of micropeptide SEQ ID NO:3 in tumor suppression, the authors of the invention tested the potential regulation of SEQ ID NO:3 by stress and by p53 protein. The authors of the invention treated the isogenic cell lines HCT116 and HCT116 p53 knock-out with the p53 activator Nutlin3a (10 μM) and with the genotoxic chemotherapeutic agent Doxorubicin (1 μM). Interestingly, SEQ ID NO 3 was upregulated with genotoxic stress in HCT116, but the upregulation was impaired in HCT116 p53 KO (FIG. 25). These results suggest that SEQ ID NO:3 regulated by stress/damage in a p53-dependent manner and thereby, possibly downregulated in all cancers with mutational inactivation of p53. Therefore, its tumor suppressor activity can be related with p53 function, supporting the use of the micropeptide as a therapeutic agent in cancer.

---

The invention claimed is:

1. A method for the treatment of cancer in a subject in need thereof, comprising the administration of a micropeptide to said subject, wherein the micropeptide comprises an amino acid sequence selected from the group consisting of SEQ ID NO: 1, 2, and 3, or a functionally equivalent variant thereof of SEQ ID NO: 2 or 3, wherein the functionally equivalent variant includes an amino acid sequences with a sequence identity of at least 70% with SEQ ID NO: 2 or 3 over the full length of the sequence being compared and wherein the functionally equivalent variant has anti-proliferative activity.

2. The method according to claim 1, wherein the cancer is a primary tumor or cancer metastasis.

3. The method according to claim 1, wherein the cancer is a carcinoma.

4. The method according to claim 3, wherein the carcinoma is selected from squamous cell carcinoma, adenocarcinoma, transitional cell carcinoma, or basal cell carcinoma.

5. The method according to claim 3, wherein the carcinoma is selected from lung carcinoma, breast carcinoma, bladder carcinoma, prostate carcinoma, colon and rectum carcinoma, skin carcinoma, pancreas carcinoma, ovarian carcinoma, cervix carcinoma, hepatocellular carcinoma, or renal cell carcinoma.

6. The method according to claim 3, wherein the functionally equivalent variant has a sequence which shows at least 80% identity with the sequence of SEQ ID NO: 2 or 3.

7. A method for the treatment of cancer in a subject in need thereof, comprising the administration of a micropeptide to said subject, wherein the micropeptide comprises an amino acid sequence selected from the group consisting of SEQ ID NO: 1, 2, and 3, wherein the micropeptide is the micropeptide of sequence SEQ ID NO: 1 or 3, and wherein the cancer is characterized in that it comprises an inactivating mutation in the p53 gene.

* * * * *